(12) United States Patent
Honda et al.

(10) Patent No.: US 7,371,849 B2
(45) Date of Patent: May 13, 2008

(54) METHODS OF CONSTRUCTING CAMEL ANTIBODY LIBRARIES

(75) Inventors: Toshio Honda, Ina (JP); Yasushi Akahori, Nagoya (JP); Yoshikazu Kurosawa, Nagoya (JP)

(73) Assignee: Institute For Antibodies Co., Ltd., Nagoya-shi (JP)

( * ) Notice: Subject to any disclaimer, the term of this patent is extended or adjusted under 35 U.S.C. 154(b) by 0 days.

(21) Appl. No.: 10/489,477

(22) PCT Filed: Sep. 13, 2002

(86) PCT No.: PCT/JP02/09448

§ 371 (c)(1),
(2), (4) Date: Oct. 1, 2004

(87) PCT Pub. No.: WO03/025020

PCT Pub. Date: Mar. 27, 2003

(65) Prior Publication Data

US 2005/0037421 A1 Feb. 17, 2005

(30) Foreign Application Priority Data

Sep. 13, 2001 (JP) ............................. 2001-277765

(51) Int. Cl.
*C07H 21/04* (2006.01)
*C12P 19/34* (2006.01)
*C12Q 1/68* (2006.01)

(52) U.S. Cl. ...................... 536/24.33; 435/91.2; 435/6

(58) Field of Classification Search ............. 536/24.33; 435/91.2, 6
See application file for complete search history.

(56) References Cited

U.S. PATENT DOCUMENTS 5,962,255 A * 10/1999 Griffiths et al. ............ 435/69.1
6,005,079 A * 12/1999 Casterman et al. ...... 530/387.1
6,399,763 B1 * 6/2002 Frenken et al. .......... 536/23.53

FOREIGN PATENT DOCUMENTS

| EP | 1 024 191 A2 | 8/2000 |
| EP | 1 024 191 A3 | 8/2000 |
| EP | 1 264 885 A1 | 12/2002 |
| WO | WO 97/49805 A2 | 12/1997 |
| WO | WO 99/42077 * | 8/1999 |
| WO | WO 00/43507 A1 | 7/2000 |
| WO | WO 01/90190 A2 | 11/2001 |
| WO | WO 01/90190 A3 | 11/2001 |
| WO | WO 02/48193 A2 | 6/2002 |

OTHER PUBLICATIONS

Nguyen et al., 2000, Camel heavy-chain antibodies: diverse germline VHH and specific mechanisms enlarge the antigen-binding repertoire, The Embo Journal, 19(5): 921-930.*
Muyldermans, 2002, Nomenclature for dromedary heavy chains, website—medicine.uiowa.edu/cigw/camel.htm, 2 pages.*
Tanha, Jamshid et al.; "Selection by phage display of llama conventional $V_H$ fragments with heavy chain antibody $V_HH$ properties"; *Journal of Immunological Methods*; 2002; pp. 97-109; vol. 263.
van der Linden, Richard H. J. et al.; "Improved production and function of llama heavy chain antibody fragments by molecular evolution"; *Journal of Biotechnology*; 2000; pp. 261-270; vol. 80.
Arbabi Ghahroudi, M. et al.; "Selecteion and identification of single domain antibody fragments from camel heavy-chain antibodies"; *FEBS Letters* 414:521-526 (1997).
Bieche, Ivan et al.; "Novel approach to quantitative polymerase chain reaction using real-time detection: application to the detection of gene amplification in breast cancer"; *Int. J. Cancer* 78:661-666 (1998).
Hoogenboom, Hennie R. et al.; "Antibody phage display technology and its applications"; *Immunotechnology* 4:1-20 (1998).
Lauwereys, Marc et al.; "Potent enzyme inhibitors derived from dromedary heavy-chain antibodies"; *The Embo Journal* 17(13):3512-3520 (1998).
Little, Melvyn et al.; "Generation of a large complex antibody library from multiple donors"; *Journal of Immunological Methods* 231:3-9 (1999).

* cited by examiner

*Primary Examiner*—Jon D. Epperson
*Assistant Examiner*—Amber D. Steele
(74) *Attorney, Agent, or Firm*—Townsend and Townsend and Crew LLP

(57) ABSTRACT

The present invention provides camel antibody libraries that maintain in vivo diversity of camelid antibody variable region genes. The in vivo diversity of antibody variable region genes can be accomplished by, for example, mixing genes derived from a plurality of animals or modifying gene amplification conditions. Conventional methods yield only VHHs with limited repertoire diversity. However, the present invention provides libraries comprising genes encoding functional VHHs with sufficient repertoire size. According to the present invention, libraries that enable to freely obtain VHHs against arbitrary antigens are provided. VHHs have excellent solubility and stability, and show a reactivity that usually cannot be expected from tetrameric IgGs.

17 Claims, 20 Drawing Sheets

FIG. 2

```
                                              M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII
 L  L  L  L  A  A  Q  P  A  M  A  E  V  Q  L  Q  Q  S  G  A  E  L  V  K
TTGTTATTACTCGCGGCCCAGCCGGCCATGGCCGAGGTTCAGCTGCAGCAGTCTGGGGCAGAGCTTGTGAAG
          SfiI              PstI
 P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG
 K  Q  R  P  E  K  G ---------- L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                      XbaI EcoRI
 D  Y  G  N  F  D  Y  W  G  Q  G  T  T  V  R  V  S  R  G  A  R  Q  S  T
TGATTACGGCAACTTTGACTACTGGGGCCAAGGCACCACGGTCAGGGTCTCGAGAGGGGCGCGCCAGTCGAC
                                              XhoI       AscI     SalI
 P  F  V  C  E  Y  Q  G  Q  S  S  D
TCCATTCGTTTGTGAATATCAAGGCCAATCGTCTG
   L  P  Q  P  P  V  N  A  G  G  G  S  G  G  G  S  G  G  G  S  E  G  G  G
ACCTGCCTCAACCTCCTGTCAATGCTGGCGGCGGCTCTGGTGGTGGTTCTGGTGGCGGCTCTGAGGGTGGTG
   S  E  G  G  G  S  E  G  G  G  S  E  G  G  G  S  G  G  G  S  G  S  G  D
GCTCTGAGGGTGGCGGTTCTGAGGGTGGCGGCTCTGAGGGAGGCGGTTCCGGTGGTGGCTCTGGTTCCGGTG
   F  D  Y  E  K  M  A  N  A  N  K  G  A  M  T  E  N  A  D  E  N  A  L  Q
ATTTTGATTATGAAAAGATGGCAAACGCTAATAAGGGGGCTATGACCGAAAATGCCGATGAAAACGCGCTAC
   S  D  A  K  G  K  L  D  S  V  A  T  D  Y  G  A  A  I  D  G  F  I  G  D
AGTCAGACGCTAAAGGCAAACTTGATTCTGTCGCTACTGATTACGGTGCTGCTATCGATGGTTTCATTGGTG
   V  S  G  L  A  N  G  N  G  A  T  G  D  F  A  G  S  N  S  Q  M  A  Q  V
ACGTTTCCGGCCTTGCTAATGGTAATGGTGCTACTGGTGATTTTGCTGGCTCTAATTCCCAAATGGCTCAAG
   G  D  G  D  N  S  P  L  M  N  N  F  R  Q  Y  L  P  S  L  P  Q  S  V  E
TCGGTGACGGTGATAATTCACCTTTAATGAATAATTTCCGTCAATATTTACCTTCCCTCCCTCAATCGGTTG
   C  R  P  F  V  F  G  A  G  K  P  Y  E  F  S  I  D  C  D  K  I  N  L  F
AATGTCGCCCTTTTGTCTTTGGCGCTGGTAAACCATATGAATTTTCTATTGATTGTGACAAAATAAACTTAT
   R  G  V  F  A  F  L  L  Y  V  A  T  F  M  Y  V  F  S  T  F  A  N  I  L
TCCGTGGTGTCTTTGCGTTTCTTTTATATGTTGCCACCTTTATGTATGTATTTTCTACGTTTGCTAACATAC
   R  N  K  E  S  *                              S  T  A  Q  H  D  E  A
TGCCGTAATAAGGAGTCTTAATCATGCCAGTTCTTTTGGGTGCTAGCTGTCGACTGCGCAACACGATGAAGCC
                                         NheI      SalI
 V  D  N  K  F  N  K  E  Q  Q  N  A  F  Y  E  I  L  H  L  P  N  L  N  E
GTAGACAACAAATTCAACAAAGAACAACAAAACGCGTTCTATGAGATCTTACATTTACCTAACTTAAACGAA
 E  Q  R  N  A  F  I  Q  S  L  K  D  D  P  S  Q  S  A  N  L  L  A  E  A
GAACAACGAAACGCCTTCATCCAAAGTTTAAAAGATGACCCAAGCCAAAGCGCTAACCTTTTAGCAGAAGCT
 K  K  L  N  D  A  Q  A  P  K  V  D  N  K  F  N  K  E  Q  Q  N  A  F  Y
AAAAAGCTAAATGATGCTCAGGCGCCCGAAAGTAGACAACAAATTCAACAAAGAACAACAAAACGCGTTCTAT
 E  I  L  H  L  P  N  L  N  E  E  Q  R  N  A  F  I  Q  S  L  K  D  D  P
GAGATCTTACATTTACCTAACTTAAACGAAGAACAACGAAACGCCTTCATCCAAAGTTTAAAAGATGACCCA
 S  Q  S  A  N  L  L  A  E  A  K  K  L  N  D  A  Q  A  P  K  V  D  A  N
AGCCAAAGCGCTAACCTTTTAGCAGAAGCTAAAAAGCTAAATGATGCTCAGGCGCCCGAAAGTAGACGCGAAT
* (SEQ ID NO:44)
TAGCTGGGAATTAATTC (SEQ ID NO:43)
```

FIG. 16

```
                                              M  K  Y  L  L  P  T  A  A  A  G
AAGCTTGCATGCAAATTCTATTTCAAGGAGACAGTCATAATGAAATACCTATTGCCTACGGCAGCCGCTGG
HindIII L  L  L  L  A  A  Q  P  A  M  A  Q  V  Q  L  Q  Q  S  G  A  E  L  V  K
TTGTTATTACTCGCTGCCCAACCAGCGATGGCCCAGGTGCAGCTGCAGCAGTCTGGGGCAGAGCTTGTGAA
                                    PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGT K  Q  R  P  E  K  G ---------- L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTT
                   XbaI EcoRI D  Y  G  N  F  D  Y  W  G  Q  G  T  T  V  T  V  S  S  G  G  G  G  S  G
TGATTACGGCAACTTTGACTACTGGGGCCAAGGCACCACGGTCACCGTCTCGAGAGGCGGTGGCGGATCAG
                                           BstPI  XhoI G  G  G  S  G  G  G  G  S  M  A
TGGCGGTGGAAGTGGCGGTGGTGGGTCCATGGCC
                              NcoI D  I  E  L  T  Q  S  P  A  S  L  S  A  S  V  G  E  T  V  T  I  T
         GACATCGAGCTCACCCAGTCTCCAGCCTCCCTTTCTGCGTCTGTGGGAGAAACTGTCACCATCA
              SacI C  R  A  S  G  N  I  H  N  Y  L  A ------- K  L  E  I  K  R  A  D  A
ATGTCGAGCAAGTGGGAATATTCACAATTATTTAGCATGGTACCAAGCTCGAGATCAAACGGGCTGATGCT
                                     KpnI     XhoI P  T  V  S  I  F  P  P  S  S  E  Q  L  T  S  G  G  A  S  V  V  C  F
CACCAACTGTATCCATCTTCCCACCATCCAGTGAGCAGTTAACATCTGGAGGTGCCTCAGTCGTGTGCTTC N  S  F  Y  P  K  D  I  N  V  K  W  K  I  D  G  S  E  R  Q  N  G  V
TGAACAGCTTCTACCCCAAAGACATCAATGTCAAGTGGAAGATTGATGGCAGTGAACGACAAAATGGCGTC N  S  W  T  D  Q  D  S  K  D  S  T  Y  S  M  S  S  T  L  T  L  T  K
TGAACAGTTGGACTGATCAGGACAGCAAAGACAGCACCTACAGCATGAGCAGCACCCTCACGTTGACCAAG E  Y  E  R  H  N  S  Y  T  C  E  A  T  H  K  T  S  T  S  P  I  V  K       (SEQ ID NO:46)
ACGAGTATGAACGACATAACAGCTATACCTGTGAGGCCACTCACAAGACATCAACTTCACCCATTGTCAAG (SEQ ID NO:45)
```

FIG. 17

```
  F  N  R  N  E  C  S  A  R  Q  S  T  P  F  V  C  E  Y  Q  G  Q  S  S
GCTTCAACAGGAATGAGTGTTCGGCGCGCCAGTCGACTCCATTCGTTTGTGAATATCAAGGCCAATCGTCT
                           AscI   SalI
  L  P  Q  P  P  V  N  A  G  G  S  G  G  G  S  G  G  G  S  E  G  G
ACCTGCCTCAACCTCCTGTCAATGCTGGCGGCGGCTCTGGTGGTGGTTCTGGTGGCGGCTCTGAGGGTGGT

S  E  G  G  G  S  E  G  G  G  S  E  G  G  G  S  G  G  G  S  G  S  G
GCTCTGAGGGTGGCGGTTCTGAGGGTGGCGGCTCTGAGGGAGGCGGTTCCGGTGGTGGCTCTGGTTCCGGT

F  D  Y  E  K  M  A  N  A  N  K  G  A  M  T  E  N  A  D  E  N  A  L
ATTTTGATTATGAAAAGATGGCAAACGCTAATAAGGGGGCTATGACCGAAAATGCCGATGAAAACGCGCTA

S  D  A  K  G  K  L  D  S  V  A  T  D  Y  G  A  A  I  D  G  F  I  G
AGTCAGACGCTAAAGGCAAACTTGATTCTGTCGCTACTGATTACGGTGCTGCTATCGATGGTTTCATTGGT

V  S  G  L  A  N  G  N  G  A  T  G  D  F  A  G  S  N  S  Q  M  A  Q
ACGTTTCCGGCCTTGCTAATGGTAATGGTGCTACTGGTGATTTTGCTGGCTCTAATTCCCAAATGGCTCAA

G  D  G  D  N  S  P  L  M  N  N  F  R  Q  Y  L  P  S  L  P  Q  S  V
TCGGTGACGGTGATAATTCACCTTTAATGAATAATTTCCGTCAATATTTACCTTCCCTCCCTCAATCGGTT

C  R  P  F  V  F  G  A  G  K  P  Y  E  F  S  I  D  C  D  K  I  N  L
AATGTCGCCCTTTTGTCTTTGGCGCTGGTAAACCATATGAATTTTCTATTGATTGTGACAAAATAAACTTA

R  G  V  F  A  F  L  L  Y  V  A  T  F  M  Y  V  F  S  T  F  A  N  I
TCCGTGGTGTCTTTGCGTTTCTTTTATATGTTGCCACCTTTATGTATGTATTTTCTACGTTTGCTAACATA

R  N  K  E  S  *                          S  T  A  Q  H  D  E  A
TGCGTAATAAGGAGTCTTAATCATGCCAGTTCTTTTGGGTGCTAGCTGTCGACTGCGCAACACGATGAAGC
                                              NheI   SalI
  V  D  N  K  F  N  K  E  Q  Q  N  A  F  Y  E  I  L  H  L  P  N  L  N  E
GTAGACAACAAATTCAACAAAGAACAACAAAACGCGTTCTATGAGATCTTACATTTACCTAACTTAAACGA

E  Q  R  N  A  F  I  Q  S  L  K  D  D  P  S  Q  S  A  N  L  L  A  E  A
GAACAACGAAACGCCTTCATCCAAAGTTTAAAAGATGACCCAAGCCAAAGCGCTAACCTTTTAGCAGAAGC

K  K  L  N  D  A  Q  A  P  K  V  D  N  K  F  N  K  E  Q  Q  N  A  F  Y
AAAAAGCTAAATGATGCTCAGGCGCCGAAAGTAGACAACAAATTCAACAAAGAACAACAAAACGCGTTCTA

E  I  L  H  L  P  N  L  N  E  E  Q  R  N  A  F  I  Q  S  L  K  D  D  P
GAGATCTTACATTTACCTAACTTAAACGAAGAACAACGAAACGCCTTCATCCAAAGTTTAAAAGATGACCC

S  Q  S  A  N  L  L  A  E  A  K  K  L  N  D  A  Q  A  P  K  V  D  A  N
AGCCAAAGCGCTAACCTTTTAGCAGAAGCTAAAAAGCTAAATGATGCTCAGGCGCCGAAAGTAGACGCGAA

*(SEQ ID NO:46)
TAGCTGGGAATTAATTC (SEQ ID NO:45)
```

FIG. 19

```
                                          M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCGGCCCAGCCGGCCATGGCCCAGGTGCAGCTGCAGCAGTCTGGGGCAGAGCTTGTGAAG
          SfiI        NcoI          PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ---------- L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                    XbaI EcoRI D  Y  G  N  F  D  Y  W  G  Q  G  T  T  V  T  V  S  S  G  G  G  G  S  G
TGATTACGGCAACTTTGACTACTGGGGCCAAGGCACCACGGTCACCGTCTCCTCAGGCGGTGGCGGATCAGG
                                     BstPI G  G  G  S  G  G  G  G  S  T  S  D  I  E  L  T  Q  S  P  A  S  L  S  A
TGGCGGTGGAAGTGGCGGTGGTGGGTCTACTAGTGACATCGAGCTCACCCAGTCTCCAGCCTCCCTTTCTGC
                             SpeI       SacI S  V  G  E  T  V  T  I  T  C  R  A  S  G  N  I  H  N  Y  L  A  W  Y  Q
GTCTGTGGGAGAAACTGTCACCATCACATGTCGAGCAAGTGGGAATATTCACAATTATTTAGCATGGTACCA
                                                                    KpnI Q  K  P  G  K  S  P  Q  L  L  V  Y  N  A  K  T  L  A  D  G  V  P  S  R
GCAGAAACCAGGGAAATCTCCTCAGCTCCTGGTCTATAATGCAAAAACCTTAGCAGATGGTGTGCCATCAAG F  S  G  S  G  S  G  T  Q  Y  S  L  K  I  N  S  L  Q  P  E  D  F  G  S
GTTCAGTGGCAGTGGATCCGGAACACAATATTCTCTCAAGATCAACAGCCTGCAGCCTGAAGATTTTGGGAG
              BamHI Y  Y  C  Q  H  F  W  S  T  P  W  T  F  G  G  G  T  K  I  E  S  T  P  F
TTATTACTGTCAACATTTTTGGAGTACTCCGTGGACGTTCGGTGGAGGTACCAAGCTCGAGTCGACTCCATT
                                              KpnI    XhoI SalI V  C  E  Y  Q  G  Q  S  S  D  L  P  Q  P  P  V  N  A  G  G  G  S  G  G
CGTTTGTGAATATCAAGGCCAATCGTCTGACCTGCCTCAACCTCCTGTCAATGCTGGCGGCGGCTCTGGTGG G  S  G  G  G  S  E  G  G  G  S  E  G  G  G  S  E  G  G  G  S  E  G  G  (SEQ ID NO:48)
TGGTTCTGGTGGCGGCTCTGAGGGTGGTGGCTCTGAGGGTGGCGGTTCTGAGGGTGGCGGCTCTGAGGGAGG  (SEQ ID NO:47)
```

FIG. 20

```
  G   S   G   G   S   G   S   G   D   F   D   Y   E   K   M   A   N   A   N   K   G   A   M
CGGTTCCGGTGGTGGCTCTGGTTCCGGTGATTTTGATTATGAAAAGATGGCAAACGCTAATAAGGGGGCTAT

T   E   N   A   D   E   N   A   L   Q   S   D   A   K   G   K   L   D   S   V   A   T   D   Y
GACCGAAAATGCCGATGAAAACGCGCTACAGTCAGACGCTAAAGGCAAACTTGATTCTGTCGCTACTGATTA

G   A   A   I   D   G   F   I   G   D   V   S   G   L   A   N   G   N   G   A   T   G   D   F
CGGTGCTGCTATCGATGGTTTCATTGGTGACGTTTCCGGCCTTGCTAATGGTAATGGTGCTACTGGTGATTT

A   G   S   N   S   Q   M   A   Q   V   G   D   G   D   N   S   P   L   M   N   N   F   R   Q
TGCTGGCTCTAATTCCCAAATGGCTCAAGTCGGTGACGGTGATAATTCACCTTTAATGAATAATTTCCGTCA

Y   L   P   S   L   P   Q   S   V   E   C   R   P   F   V   F   G   A   G   K   P   Y   E   F
ATATTTACCTTCCCTCCCTCAATCGGTTGAATGTCGCCCTTTTGTCTTTGGCGCTGGTAAACCATATGAATT

S   I   D   C   D   K   I   N   L   F   R   G   V   F   A   F   L   L   Y   V   A   T   F   M
TTCTATTGATTGTGACAAAATAAACTTATTCCGTGGTGTCTTTGCGTTTCTTTTATATGTTGCCACCTTTAT

Y   V   F   S   T   F   A   N   I   L   R   N   K   E   S   *
GTATGTATTTTCTACGTTTGCTAACATACTGCGTAATAAGGAGTCTTAATCATGCCAGTTCTTTTGGGTGCT
                                                                                          NheI

S   T   A   Q   H   D   E   A   V   D   N   K   F   N   K   E   Q   Q   N   A   F   Y   E
AGCTGTCGACTGCGCAACACGATGAAGCCGTAGACAACAAATTCAACAAAGAACAACAAAACGCGTTCTATG
      SalI

I   L   H   L   P   N   L   N   E   E   Q   R   N   A   F   I   Q   S   L   K   D   D   P   S
AGATCTTACATTTACCTAACTTAAACGAAGAACAACGAAACGCCTTCATCCAAAGTTTAAAAGATGACCCAA

Q   S   A   N   L   L   A   E   A   K   K   L   N   D   A   Q   A   P   K   V   D   N   K   F
GCCAAAGCGCTAACCTTTTAGCAGAAGCTAAAAAGCTAAATGATGCTCAGGCGCCGAAAGTAGACAACAAAT

N   K   E   Q   Q   N   A   F   Y   E   I   L   H   L   P   N   L   N   E   E   Q   R   N   A
GAGATCTTACATTTACCTAACTTAAACGAAGAACAACGAAACGCCTTCATCCAAAGTTTAAAAGATGACCCA

F   I   Q   S   L   K   D   D   P   S   Q   S   A   N   L   L   A   E   A   K   K   L   N   D
TCAACAAAGAACAACAAAACGCGTTCTATAGCCAAAGCGCTAACCTTTTAGCAGAAGCTAAAAAGCTAAATG

A   Q   A   P   K   V   D   A   N   *  (SEQ ID NO:48)
ATGCTCAGGCGCCGAAAGTAGACGCGAATTAGCTGGGAATTAATT (SEQ ID NO:47)
```

METHODS OF CONSTRUCTING CAMEL ANTIBODY LIBRARIES

TECHNICAL FIELD

The present invention relates to methods of constructing camel antibody libraries.

BACKGROUND ART

Two structures of IgGs constituting the immunoglobulins (antibody molecules) of camelids are known to exist: one a heterotetramer having heavy chains and light chains, and the other consisting of a heavy-chain dimer (Isr. J. Vet. Med. 43(3), 198 (1987); Hamers-Casterman et al., Nature, 363, 446 (1993)). The tetrameric structure is a common characteristic of IgGs among humans and most animals. On the other hand, the latter IgG having a heavy-chain dimer structure is considered characteristic of camelids. The IgGs consisting of a heavy chain dimer of camelids does not accidentally result from pathologic conditions.

Immunoglobulins lacking light chains have been found in *Camelus bactrianus* and *Camelus dromedarius*, which are Asian and African camelids, as well as in all species of South American camelids. South American camelids include *Lama pacos, Lama glama*, and *Lama vicugna*. The molecular weight of dimeric IgG differs depending on the animal species. The molecular weight of heavy chains constituting these immunoglobulins is approximately 43 kDa to approximately 47 kDa, and normally are 45 kDa.

Another characteristic of the heavy-chain dimer IgG is that this antibody lacks the first domain of the constant region called CH1 according to the definition by Roitt et al. Furthermore, the hinge region has an amino acid sequence different from that of a normal heterotetrameric antibody (heavy chains+light chains). Based on the differences in the amino acid sequences, the IgGs of dromedaries are classified as follows (Hamers-Casterman et al., Nature 363, 446 (1993)):

IgG2: comprising a long hinge sequence (SEQ ID NO: 8);
IgG3: comprising a short hinge sequence (SEQ ID NO: 9); and
IgG1: heterotetrameric antibody.

Since the VH region of a heavy chain dimer IgG does not have to make hydrophobic interactions with a light chain, the region in the heavy chain that normally contacts a light chain is mutated to hydrophilic amino acid residues. Due to structural differences compared to VHs of normal heterotetrameric IgGs, VH domains of the heavy-chain dimer IgGs are called Variable domain of the heavy-chain of heavy-chain antibody (VHH).

VHH has excellent solubility due to its hydrophilic amino acid residues. Amino acid substitutions are scattered throughout the primary structure (amino acid sequence) of VHH. Additionally, these hydrophilic amino acid residues form a cluster in the space of the tertiary structure of VH corresponding to the site that interacts with the VL domain. Herein, the aforementioned space of the tertiary structure is specifically called former VL side. These amino acid substitutions are, for example, V37F or V37Y, G44E, L45R or L45C, and W47 are also mostly substituted with Gly. Such substitutions increase the hydrophilicity of the former VL side of VHH.

Therefore, the solubility of VHH is much higher than that of VH isolated and purified from humans or mice (single domain antibody; Ward et al., Nature, 341, 544 (1989)). VHH can be easily concentrated to 10 mg/mL in ordinary buffer solutions without any signs of aggregation. This concentration corresponds to, for example, approximately 100 times the solubility of mouse VH.

Furthermore, VHHs derived from camels and llamas have very high thermostability compared to mouse heterotetrameric antibodies. The use of VHH derived from these species can provide, for example, molecules that maintain their antigen binding ability even at 90° C. (van der Linden et al., Biochim. Biophys. Acta 1431 (1), 37 (1999))

The diversity of antibody repertoire of camelids is determined by the complementary determining regions (CDR) 1, 2, and 3 in the VH or VHH regions. Possession of three CDRs is in common with the IgGs of other animal species. However, the CDR3 in the camel VHH region is characterized by its relatively long length averaging 16 amino acids (Muyldermans et al., Protein Engineering 7(9), 1129 (1994)). For example, compared to the CDR3 of mouse VH having an average of 9 amino acids, the CDR3 of camel IgG is very long.

Most antigen binding sites of structurally known heavy chains+light chains heterotetrameric antibodies are known to form antigen-binding surfaces such as grooves, cavities, and flat areas (Webster et al., Current Opinion in Structural Biology 4, 23 (1994)). Therefore, when an epitope of a substance to be bound also forms a groove or a cavity, the antigen-binding site of the antibody may not bind well. For example, in proteins including enzymes, catalytic or functional residue, or toxic region is often located at the interior of a cleft. This structure facilitates extremely specific interactions of enzyme substrates and receptors with proteins. However, structures such as cavities and clefts are difficult for heterotetrameric antibodies to recognize, and therefore, they do not have high immunogenicity.

In contrast, there are reports that VHHs of camelids can specifically recognize clefts and cavities due to their characteristic structure described above. For example, in an experiment where antibodies were isolated from peripheral blood of camels immunized with an enzyme as the antigen, antibodies that seal the enzyme active center existed only among the camel IgG2 and IgG3, and not in IgG1 (Lauwereys et al., EMBO J. 17(13), 3512 (1998)). Furthermore, VHH having lysozyme activity inhibitory effect was isolated by the phage display method from a library derived from camels immunized with lysozyme (Arbabi Ghahroudi et al., FEBS Letters 414, 521 (1997)). The structure of the isolated VHH in complex with lysozyme was elucidated by X-ray crystallographic analysis (Desmyter et al., Nature Structural Biology 9, 803 (1996)). The results showed that in IgG2 or IgG3 of the camel antibody, the CDR3 region having a long protrusion is inserted and bound to the substrate-binding site of the enzyme such that the active center is sealed to cause competitive inhibition.

Industrially useful characteristics can be found in VHHs derived from camelids such as high solubility and the possible existence of novel activity that cannot be expected from tetrameric IgGs. To obtain an antibody variable region, an animal must be immunized with an antigen of interest to separate an antibody. However, such a classical method involves problems such as the need to purify large amounts of antigens and generation of non-specific antibodies. Accordingly, as a method for more easily obtaining an antibody variable region, a screening method using an rgdp library has been proposed. The phrase "rgdp library" refers to a library consisting of a genetic display package wherein genes encoding substances with binding affinity, such as antibody variable regions, display their expression products.

A representative example of an rgdp library includes a phage library that displays antibody variable regions.

The method of obtaining antibodies using a phage library displaying antibody variable regions is being noticed as a novel method for obtaining antibodies that succeed to labor-intensive, classical methods of antibody production. The present inventors have also constructed novel antibody libraries that allow efficient acquisition of antibody variable regions, and have already filed a patent application (WO 01/62907). It would also be useful for VHHs to construct a library that allows to freely select a VHH with a binding affinity towards an arbitrary antigen from the library. However, several problems have been pointed out in the construction of camelid VHH libraries.

Another characteristic of the structure of camelid VHH is that it often contains a cysteine residue in the CDR3 in addition to cysteines normally existing at positions 22 and 92 of the variable region. The cysteine residues in CDR3 are considered to form disulfide bonds with other cysteines in the vicinity of CDR1 or CDR2 (Muyldermans et al., Protein Engineering 7(9), 1129 (1994); Muyldermans et al., J. Mol. Recognit. 12, 131 (1999)). CDR1 and CDR2 are determined by the germline V gene. They play important roles together with CDR3 in antigen binding (Desmyter et al., Nature Structural Biology, 9, 803 (1996); Structure 7(4), 361-370 (1999); Spinelli et al., J. Mol. Biol. 311(1), 123 (2001)). In general, the term "germline" refers to chromosomal genes maintained in germ cells, i.e., chromosomal genes that have not undergone rearrangement. Herein, among the chromosomal genes, particularly the region that constitutes the antibody gene is referred to as germline.

Recently, germlines of dromedaries and llamas belonging to *Camelidiae* were studied. As a result, IgGs of dromedaries and llamas were classified according to the length of CDR2 and cysteine positions in the V region (Nguyen et al., EMBO J. 19(5), 921 (2000); Harmsen et al., Mol. Immunol. 37, 579 (2000)).

However, it has been noted that the antibody genes of the entire germline of a dromedary cannot be considered as sufficiently covered by hitherto obtained antibody genes. For example, the concentration of the classification of cDNA nucleotide sequences of the antibodies obtained so far on particular classes reveal that the germlines from which these antibodies were derived had been biased (Nguyen et al., EMBO J. 19 (5), 921 (2000)). Furthermore, methodologically, they were considered to imply problems as follows. Specifically, known libraries were constructed using only one type of primer as the N-terminal primer. Therefore, due to problems of specificity, some germlines from which the VHH genes are derived might have leaked, or the amplification products might have been biased (Arbabi Ghahroudi et al., FEBS Letters 414, 521 (1997)).

A library having biased constituent genes is poor in repertoire. Therefore, screening of such a library may not yield antibodies against an antigen of interest. This may be the reason why antibodies inhibiting or promoting an enzyme activity could not be obtained from phage libraries derived from non-immunized camels.

Prior art proposes methods to immunize camels or llamas in advance with a sufficient amount of antigen in order to obtain the variable region of immunoglobulin heavy chains of camels or llamas (Published Japanese Translation of International Publication No. Hei 11-503918; Lauwereys et al., EMBO J. 17(13), 3512 (1998); Arbabi Ghahroudi et al., FEBS Letters 414, 521 (1997)). This method utilizes the phenomenon that the immune systems of camels and llamas mature their own heavy chain antibodies in vivo (Published Japanese Translation of International Publication No. 2000-515002; J. Immuno. Methods 240, 185 (2000)). Based on this method, antibodies that recognize lysozyme, tetanus toxoid, carbonic anhydrase, amylase, RNaseA, azo dye and such have been obtained.

However, the need of immunological sensitization in this method imposes various restrictions such as those described below:

necessity of immunological sensitization period;
toxic influence of immunogens on camelids;
difficulty in obtaining antibodies against substances with low immunogenicity; and
necessity of relatively large amounts of antigens for immunological sensitization.

Furthermore, to avoid the problems of immunological sensitization, a method comprising the following steps was proposed (Published Japanese Translation of International Publication No. 2000-515002):

1) randomly selecting camelid heavy-chain antibodies;
2) isolating coding sequences and cloning them into phage display vectors;
3) modifying those coding sequences in at least one codon by random substitution;
4) constructing a library of the randomly mutated coding sequences in the phage display vectors;
5) expressing the coding sequences in phages transfected with those vectors; and
6) subsequently, sorting the phages with immobilized antigen to select recognition molecules specific to the antigen.

As an alternate solution, a method using the framework of camel antibody has also been suggested. According to this method, camel antibodies are reconstructed by incorporating CDR1, CDR2, and CDR3 of VHH and VH into the camel antibody framework. This method applies the method developed for humanizing mouse VH. The loops of each CDR can be mutated randomly to enlarge the repertoire size. As a result, the affinity and specificity of the antibodies can be controlled (Published Japanese Translation of International Publication No. 2000-515002).

All of these solutions are based on the principle of aiming to attain diversity by introducing artificial mutations into the coding sequences. However, most of these attempts require a great deal of effort and complicated procedures to introduce the mutations, and takes a long time. Furthermore, many of such attempts accompanied inefficiency of producing overhigh inactive antibodies along with the production of active antibodies.

A conceivable alternative method involves constructing a phage library by incorporating VHH genes obtained from tissues and blood of non-immunized camels into phage display vectors, and selecting recognition molecules specific to an antigen by selecting phages that have binding ability from the phage library using the immobilized antigen. However, this method had been contemplated to only yield VHHs against substances with sufficient immunogenicity. Therefore, methods using phage libraries incorporating VHH genes had not been sufficiently studied (Published Japanese Translation of International Publication No. 2000-515002). Accordingly, non-immunized camel-derived VHH antibody phage libraries comprising a repertoire diverse enough to yield antibodies inhibiting or promoting enzyme activities had not existed.

DISCLOSURE OF THE INVENTION

An objective of the present invention is to provide VHH libraries having a sufficient repertoire size. Furthermore, another objective of the present invention is to provide VHH libraries that do not accompany production of inactive VHH.

The present invention provides VHH libraries having a very large diversified repertoire by improving the conventional process of isolating VHH variable regions. More specifically, by devising primers for amplifying genes, germline VHH genes could be amplified that much faithfully reproduce the in vivo diversity.

Furthermore, the present inventors showed that VHHs are antibody molecules developed in camelids having mainly supplementary importance, and are a group whose antibody maturation process completely differs from that of VH genes. Therefore, to maximize the diversity of VHH genes, the present inventors aimed to ensure diversity by increasing the number of animals, which had not been emphasized in previous libraries. As a result, a library with rich diversity was successfully constructed using camel genes from more than one animal.

Moreover, to minimize the loss of diversity during amplification of genes by PCR, the present inventors collected the genes amplified by PCR in the exponential phase, and avoided saturation of some of the genes. In addition, the present inventors also obtained the variable region genes of the IgM class. Generally, it is suggested that naive repertoires are included in the immunoglobulins of the IgM class. IgGs may accompany bias of clones due to natural immunological sensitization of camels in vivo. Meanwhile, such bias is considered not to occur in IgM.

According to such processes, non-immunized antibody variable region libraries that ensure extremely large diversity can be constructed. Thus, the present invention relates to antibody variable region libraries, methods for constructing them, and uses thereof as follows:

[1] a library of camelid-derived VHHs, which maintains the in vivo diversity of variable regions in a camelid;

[2] the library of [1], wherein 33 arbitrary clones selected from clones constituting the library comprise genes belonging to at least 8 or more classes;

[3] the library of [2], wherein a sufficient amount of clones randomly selected from clones constituting the library comprise genes of at least 6 VHH subfamilies, and at the same time genes belonging to 15 or more classes;

[4] the library of [1] comprising at least $10^5$ or more VHH gene clones;

[5] the library of [1] consisting of VHH gene clones derived from immunoglobulin genes of IgG2 and/or IgG3;

[6] the library of [5], wherein the VHH gene rate in the library is 60% or more;

[7] the library of [1], which is an rgdp library;

[8] a method of obtaining a gene encoding a VHH that has an affinity for a substance of interest, which comprises the steps of:
(1) contacting the library of [7] with the substance of interest, and
(2) selecting a clone encoding a VHH that binds to the substance of interest;

[9] the method of [8], wherein the substance of interest is an enzyme molecule or a fragment thereof;

[10] a method of obtaining a VHH that has a function to regulate an enzyme activity, which comprises the steps of:
(1) obtaining a VHH that binds to an enzyme by the method of [9],
(2) contacting the VHH obtained in step (1) with the enzyme, and
(3) selecting the VHH that has a function to modify the enzyme activity of said enzyme compared to that in the absence of the VHH;

[11] a gene encoding the VHH selected by the method of [8] or [10];

[12] a method of producing an immunoglobulin comprising a camelid-derived VHH as a variable region, or a fragment thereof, which comprises the steps of:
(1) obtaining a gene encoding a VHH that has an binding activity for a substance of interest by the method of [8],
(2) preparing a VHH expression vector by incorporating the obtained VHH-encoding gene into a vector expressible in a host cell, and
(3) introducing the VHH expression vector into the host cell to collect proteins comprising the VHH from the culture;

[13] a method of constructing a VHH library, which comprises the steps of:
(1) obtaining VHH genes from a plurality of animals belonging to *Camelidae*, and
(2) preparing a library by mixing the VHH genes obtained in step (1);

[14] the method of [13], which comprises the step of amplifying the VHH genes obtained in step (1);

[15] the method of [14], wherein the amplification is performed by PCR;

[16] the method of [15], which comprises the step of collecting amplification products of the PCR during the exponential phase;

[17] the method of [15], wherein the animals of *Camelidae* are dromedaries and the PCR is performed using primer sets consisting of a 5' primer selected from any one of the oligonucleotides having the nucleotide sequences of SEQ ID NOs: 1 to 6, and a 3' primer consisting of an oligonucleotide having the nucleotide sequence of SEQ ID NO: 10, and which comprises the step of mixing the amplification products from each of the primer sets;

[18] the method of [15], wherein the animals of *Camelidae* are dromedaries, and the PCR is performed using primer sets consisting of a 5' primer selected from any one of the oligonucleotides having the nucleotide sequences of SEQ ID NOs: 1 to 6, and a 3' primer consisting of an oligonucleotide having the nucleotide sequence of SEQ ID NO: 11, and which comprises the step of mixing amplification products from each of the primer sets;

[19] the method of [17] or [18] comprising the step of digesting the amplification products with restriction enzymes SfiI and AscI, and ligating the digested products into vectors having features (i) and (ii) as follows:
(i) comprising a SfiI site and an AscI site; and
(ii) upon transformation of the vector into an appropriate host, expressing a protein encoded by an exogenous gene inserted into the site of (i) as a fusion protein with a protein constituting a phage;

[20] a VHH library, which can be constructed by the method of [17] or [18];

[21] a primer set for camel VHH gene amplification consisting of a 5' primer selected from oligonucleotides having the nucleotide sequences of SEQ ID NOs: 1 to 6, and a 3' primer selected from oligonucleotides having the nucleotide sequences of SEQ ID NOs: 10 and 11, respectively;

[22] a method of constructing a VH library, which comprises the steps of:
(1) obtaining VH genes from a plurality of animals of *Camelidae*, and
(2) preparing a library by mixing the VH genes obtained in step (1);

[23] the method of [22] comprising the step of amplifying the VH genes obtained in step (1);

[24] the method of [23], wherein the amplification is performed by PCR;

[25] the method of [24] comprising the step of collecting the amplification products of the PCR during the exponential phase;

[26] the method of [24], wherein the animals of *Camelidae* are dromedaries, and the PCR is performed using primer sets consisting of a 5' primer selected from any one of the oligonucleotides having the nucleotide sequences of SEQ ID NOs: 1 to 6 and a 3' primer consisting of an oligonucleotide having the nucleotide sequence of SEQ ID NO: 41, and which comprises the step of mixing the amplification products from each of the primer sets;

[27] the method of [26] comprising the step of digesting the amplification products with restriction enzymes SfiI and AscI and ligating the digested products to a vector having features (i) and (ii) as follows:

(i) comprising a SfiI site and an AscI site, and (ii) upon transformation of the vector into an appropriate host, expressing a protein encoded by an exogenous gene inserted into the site of (i) as a fusion protein with a protein constituting a phage;

[28] a VH library derived from camelid IgM;

[29] a VH library obtainable by the method of [22];

[30] the library of [28] or [29], which is an rgdp library;

[31] a method of obtaining a gene encoding a VH that has an affinity for a substance of interest, which comprises the steps of:

(1) contacting the library of [30] with the substance of interest, and (2) selecting a clone comprising a VH that binds to the substance of interest;

[32] the method of [31], wherein the substance of interest is an enzyme molecule or a fragment thereof;

[33] a method of obtaining a VH comprising a function to regulate an enzyme activity, which comprises the steps of:

(1) obtaining a VH that binds to an enzyme by the method of [31], (2) contacting the VH obtained in step (1) with the enzyme, and (3) selecting the VH that has a function to modify the enzyme activity of the enzyme compared to that in the absence of the VH;

[34] a gene encoding a VH selected by the method of [31];

[35] a method of producing an immunoglobulin comprising a dromedary-derived VH as a variable region, or a fragment thereof, which comprises the steps of:

(1) obtaining a gene encoding a VH having a binding activity for a substance of interest by the method of [31], (2) preparing a VH expression vector by incorporating the obtained VH-encoding gene into a vector expressible in a host cell, and (3) introducing the VH expression vector into the host cell to collect proteins comprising the VH from the culture; and

[36] a primer set for dromedary VH gene amplification that consists of a 5' primer selected from any one of the oligonucleotides having the nucleotide sequences of SEQ ID NOs:1 to 6, and a 3' primer consisting of an oligonucleotide having the nucleotide sequence of SEQ ID NO: 41.

The present invention relates to libraries of camelid-derived antibody variable regions, which maintain the in vivo diversity of the variable regions of a camelid. A VHH library comprising VHH genes as variable region genes can be confirmed to maintain the in vivo diversity as follows. Specifically, 33 arbitrary clones may be selected from clones constituting a library, and when the selected clones are determined to comprise genes belonging to at least 8 or more classes, this library can be assumed to maintain the in vivo diversity. More specifically, sufficient amount of clones may be randomly selected from clones constituting a library, and when the selected clones are determined to comprise genes of preferably 6 VHH subfamilies and at the same time genes belonging to 15 or more classes, this library can be assumed to maintain the in vivo VHH diversity.

In the present invention, the VHH subfamilies are classified based on the positions of cysteine residues. On the other hand, the classes are grouped based on the position of cysteine residues, the length of CDR2, and the length of CDR1. In Table 1 shown in Example 2, each frame corresponds to one class.

The conventional subfamily classification of VHHs (Nguyen et al., EMBO J. 19(5), 921 (2000); Harmsem M M et al., Mol. Immunol. 37(10), 579-590 (2000)) is based on the positions of cysteine residues and the length of CDR2. However, according to the analysis by the present inventors, cysteine residues and CDR2 lengths that could not be covered by the conventional classification were found. Furthermore, though the number of amino acid residues constituting CDR1 had been considered to be restricted to one value, CDR1 with different numbers were found according to the analysis of the present inventors. Therefore, VHHs cannot be virtually classified based on the conventional classification.

Applying the method of classification of subfamilies and classes of this invention to a known library analysis result (Nguyen et al., EMBO J. 19(5), 921 (2000)), 5 subfamilies and 7 classes (from 72 clones) were found. On the other hand, following results were obtained for the VHH libraries of the present invention, for example, when the classification method of this invention was applied to the analysis result of clones constituting VHH libraries constructed in the Examples described later. Results of analyzing 89 arbitrary clones from IgG2-derived VHH library:

number of subfamilies: 7 number of classes: 31 Results of analyzing 59 arbitrary clones from IgG3-derived VHH library:

number of subfamilies: 7 number of classes: 20

Based on these findings, the present inventors deemed that a library could be judged to maintain a sufficient diversity when 50 or more arbitrary clones constituting the library are determined to contain genes of 6 or more subfamilies and 15 or more classes, based on the classification of the present invention.

Specifically, a VHH library of the present invention preferably comprises, for example, $10^5$ or more clones. Therefore, a non-immunized camel antibody library preferably comprises at least $10^5$ or more clones. More preferably, the antibody libraries of the present invention can be prepared as practical libraries by comprising $10^6$ or more, normally $10^7$ or more, or $10^8$ or more, even more preferably $10^9$ or more, and ideally $10^{10}$ or more clones.

For example, a camel antibody library of the present invention obtainable by methods such as those mentioned later comprises $10^{10}$ or more clones. A VHH gene library with such a rich variety has not been reported so far. More importantly, the percentage of normal genes in the VHH genes constituting the libraries of this invention is extremely high. Whether the VHH genes are normal or not can be confirmed by determining their nucleotide sequence and by analyzing following qualities:

presence of a framework with a nucleotide sequence highly homologous to known camel antibody framework;

absence of frame shift in the amino acid sequence to be translated; and no generation of a stop codon.

More preferably, it is also an important factor for normal VHH genes to encode a protein having hydrophilic amino acid residues at the position of the hinge region where the VHH-characteristic hydrophilic amino acids are located.

Preferably, 80% or more, more preferably 85% or more, even more preferably 90% or more, and particularly preferably 95% or more of the VHH genes constituting the libraries of the present invention are normal. More specifically, the present invention relates to VHH libraries comprising 90% or more normal IgG2-derived VHH genes. Alternatively, the present invention relates to VHH libraries comprising 95% or more normal IgG3-derived VHH genes. A library with the aforementioned high diversity and comprising normal VHH genes in such high proportions cannot be obtained according to conventional methods.

In the present invention, "VHH" refers to the variable region constituting an immunoglobulin having a dimeric structure that is found in the blood of camelids. VHH genes constituting the libraries of the present invention may carry a constant region in addition to the variable region. Therefore, the VHH genes may accompany the nucleotide sequence of a hinge region. Since VHHs and VHs often show structural differences in the hinge regions, VHH genes can be specifically collected by setting primers at the hinge region in order to obtain VHH genes carrying the hinge region.

Accordingly, in the Examples described below, 3' (C-terminal) primers were set in the hinge region. As a result, VHH of the desired class was present at a high percentage as shown below in each group of VHH genes amplified by primers used in the Examples.

IgG2 (SEQ ID NO: 10) VH:VHH=7:91 (93% VHH)
IgG3 (SEQ ID NO: 11) VH:VHH=1:167 (99% VHH)
IgM (SEQ ID NO: 41) VH:VHH=189:3 (1.6% VHH)

The VHH libraries of the present invention can be constructed using techniques, for example, as below. These techniques are all useful for supplementing the lack in repertoire size of VHHs.

(1) Utilizing VHH genes derived from a plurality of individuals.
(2) Amplifying VHH genes using primers that allow amplification of a wide variety of genes.
(3) In the interest of amplifying VHH genes, collecting amplification products during the progress of exponential amplification.

In the following, these techniques will be described more specifically.

(1) Utilizing VHH genes derived from a plurality of individuals

According to the findings of the present inventors, the repertoire size of camelid VHH genes is often limited and biased. Therefore, construction of a library with a repertoire size allowing optional acquisition of an antibody against an arbitrary antigen is difficult using VHH genes from one individual alone. Thus, the use of VHH genes from more than one individual to construct a library allows effective enlargement of the repertoire size.

The phrase "VHH genes of more than one individual" indicates that it comprises VHH genes obtained from a plurality of genetically different individuals. The phrase "a plurality of genetically different individuals" refers to individuals with genetic differences at the genomic level. Therefore, even if the individuals are littermates, they are genetically different individuals when they are not monozygotic. However, for the purpose of increasing the repertoire size of a library, it is advantageous to combine individuals with more distant genetic relationships.

In the present invention, VHH genes of more than one individual can be obtained by adding VHH genes from one individual to VHH genes derived from another individual. There are no limitations on the VHH genes to be added. Therefore, for example, even when a partial group of VHH genes derived from another individual is added, such collection of VHH genes are also encompassed by the present invention.

VHH genes to be added are preferably collected from $10^5$ or more cells per individual, and it is desirable to add the entire group of VHH genes obtained from each individual. By utilizing the entire group of genes, bias of genes can be prevented. Since the bias of genes causes decrease in the repertoire size, it is effective to add, if possible, the entire group of VHH genes. The phrase "entire group of VHH genes" refers to all of the obtained VHH genes. Specifically, the present invention encompasses libraries wherein not only all VHH genes from a certain individual are added, but also those wherein all obtainable VHH genes are added.

Furthermore, in the present invention, VHH genes derived from another individual that are added to VHH genes derived from a certain individual are preferably added evenly to avoid bias between the individuals. The purpose of mixing the VHH genes is to enlarge the repertoire size. When the VHH genes are biased between individuals in a library, the possibility increases that the VHH genes derived from a particular individual are preferentially selected in the screening using the library. Under such a circumstance, the effect of enlarging the repertoire size will be diminished. Therefore, it is important to decrease the bias between individuals. Thus, when adding VHH genes from another individual to VHH genes derived from a certain individual, they are preferably added at an equal amount to the VHH genes derived from the certain individual. Furthermore, when mixing VHH genes derived from a plurality of individuals, it is preferred to use equal amounts of VHH genes from each individual.

(2) Amplifying VHH genes using primers that allow amplification of wider variety of genes When an amount of mRNAs required for constructing a library can be obtained from an individual, a library can be constructed as it is. However, since the amount of mRNAs obtainable from an individual is normally very small, the mRNAs are amplified to construct a VHH gene library. At this time, unless every single VHH gene is amplified, the repertoire size of the library cannot be enlarged.

In the present invention, there are no limitations on the methods of gene amplification. Any method may be used as long as it allows amplification of the group of VHH genes as thoroughly as possible. When using PCR as the method of gene amplification, primers expected to amplify a wide variety of VHH genes are used. Primers for obtaining VHH genes of camels and llamas are well known in the art. However, according to the knowledge of the present inventors, amplification of VHH genes without bias is difficult when known primers are used alone.

Therefore, the present inventors newly designed primers that allow amplification of VHH genes with less bias. The nucleotide sequences of N-terminal (5'-side) primers for amplifying dromedary VHH genes designed by the present inventors are described in SEQ ID NOs: 1 to 6. Furthermore, primers that can anneald between the hinge region and CH3 can be used as C-terminal (3'-side) primers. Such primers are well known in the art. For example, the present inventors analyzed the amino acid sequences of the hinge regions of IgG2 and IgG3, and designed primers consisting of the nucleotide sequences of SEQ ID NOs: 10 and 11, for IgG2 and IgG3, respectively. These primers can be used in 12 different combinations as primer sets, where each of the 6 kinds of 5' primers is combined with either of the 2 kinds of 3' primers.

Apart from dromedary, to amplify VHH genes of *Camelidae*, the nucleotide sequences of VHH genes of interest may be analyzed by the analysis methods described in the Examples to design primers.

Some antibodies with VH structures that regulate the activity of an enzyme have been obtained. Therefore, the present inventors featured on the antigen recognition repertoire of IgM. IgM can be considered to be a prototype of the variable region at the stage without antigenic stimulation, when complementing the antigen recognition repertoire of VHHs of IgG with the variable regions of IgM. During the in vivo maturation of heavy chains upon immunization, IgM retains the prototypes of variable regions against all kinds of antigens. Therefore, the present inventors considered that IgM maintains the blueprint for producing IgG variable regions optimized for an antigen by class change. Accordingly, the present inventors newly utilized a camel μ-chain recognition sequence (SEQ ID NO: 41) to successfully isolate the variable region of IgM. This IgM-derived heavy chain variable region library can further enlarge the diversity of the repertoire and is useful for isolating recognition molecules and enzyme activity regulating molecules. In the present invention, the use of mRNAs derived from a plurality of individuals is also effective in constructing a library consisting of IgM-derived VHs to maintain a highly diverse repertoire.

IgM-derived VH libraries have a complementary meaning to the VHH repertoire derived from IgG2 or IgG3. "Complementary" means that they supplement antibody variable regions having functions that cannot be selected from VHHs or are difficult to select due to small population among VHHs. Antibody variable regions that can recognize a wider variety of molecules can be obtained by combining these libraries. More specifically, antibody variable regions having functions to regulate enzyme activities of a greater variety of enzymes can be isolated.

Combining these primers and using mRNAs obtained from camel antibody-producing cells as templates, VHH genes (mainly comprising VH genes for IgM) are amplified by PCR. Splenocytes, peripheral blood B cells, and such can be used as the antibody-producing cells. The amplified VHH genes are collected to construct a VHH library of the present invention.

In the present invention, a large repertoire size is achieved by adding VHH genes of another individual to VHH genes derived from a certain individual. For this purpose, amplification products may be mixed, or alternatively, pre-mixed mRNAs derived from a plurality of individuals may be used as templates to amplify the genes. Collecting a fixed amount of mRNAs from a plurality of individuals and amplifying genes using mixtures of the mRNAs as templates, the bias of genes among individuals can be diminished. Furthermore, this method is reasonable since the operations of amplifying and collecting genes only need to be performed once.

More specifically, mRNAs are collected from a plurality of camels and equal amounts of the mRNAs are mixed to produce an mRNA pool. cDNAs are synthesized from this mRNApool using random primers, oligo-dT primers, primers homologous to a constant region, or such, and used as templates for PCR. In the PCR, as described in (3), amplification products are collected at the exponential phase.

The VHH libraries of the present invention can be separated into IgG2 and IgG3 libraries, or each of the libraries can be mixed to form a single library. Furthermore, when combining VH libraries of IgM, each of the libraries can be prepared as separate libraries, or each of the libraries can be mixed to form a single library. When forming the libraries separately, libraries of IgG2, IgG3, and IgM can be prepared by mixing amplification products of the same 3' primers among the aforementioned primers.

Constructing a library for each of the respective classes of VHHs derived from IgG2 or IgG3, or VHs derived from IgM allows screening of VHHs (or VHs) unaffected by other classes. For example, the present inventors found that when IgG2 and IgG3 were mixed for the screening, IgG2 tended to be preferentially selected in certain cases. This may occur due to the differences in the expression level of each of the classes, the differences in the number of constituent clones, and such. Separating the libraries by class increases the possibility to obtain unbiased antibodies from each of the classes that has the function of interest without such interference of VHHs between classes.

Alternatively, when amplified VHH gene products are mixed after amplification from each of the individuals, the bias of genes is prevented by maintaining a constant ratio of genes among individuals. More specifically, conditions for gene amplification such as the amount of templates, the combination of primers, and the number of PCR reactions are strictly matched among the individuals. Furthermore, by evenly mixing the amplification products, the bias of genes can be prevented. The absence of bias in a library signifies that the in vivo germline ratio of VHH gene expression products is maintained in the library.

VHH genes are formed by the rearrangement of VH-D-JH genes in the germline. Theoretically, by investigating clones constituting a VHH gene expression product, it is possible to determine from which gene segment within the germline the VH, D, and JH of the VHH gene are derived. Furthermore, the investigation of a plurality of clones allows to estimate the in vivo frequency of each gene segment with respect to all of the expression products. Herein, thus determined frequency estimated for each gene segment in all of the expression products is referred to as "germline ratio".

In practice, since the genetic sequence of each of the gene segments have not been completely elucidated, germline ratios were analyzed based on the classifications of "subfamily" or "class" described later. Each of the gene segments can be classified into a "subfamily" or a "class" according to characteristics such as the length of CDR sequences, and Cys positions. In a biased library, the expression frequency of clones derived from a certain gene segment may be different from that in vivo. Therefore, the germline ratio can be used for evaluating libraries.

Twelve primer sets used by the present inventors can amplify any germline gene that may constitute a VHH gene. Specifically, using the above-mentioned primers, construction of libraries maintaining the in vivo ratio of germlines from which VHHs are derived is possible.

The diversity of VHH is considered to come from the combination of three gene segments, VH-D-JH, constituting the antibody gene, addition and deletion of nucleotides during the rearrangement process of these gene segments, and mutations in antibody producing cells. These mechanisms are believed to be the same as the general mechanism for obtaining antibody diversity in mammals.

Among the mechanisms supporting the diversity of VHHs, the step of selecting and rearranging each segment of VH-D-JH is a genetic change that occurs in the chromosome along with the maturation of B cells. The rearrangement of heavy chain VH-D-JH genes at the antibody gene loci during B cell differentiation occurs regardless of the presence of antigens. One B-cell expresses one set of VH-D-JH genes. Derivation from the same germline does not mean for the cells to produce the same VHH.

Antibody producing cells are a population of cells each comprising a different combination of VH-D-JH genes. When constructing a library of VHH genes, loss of a portion of the germline-derived antibody genes (i.e., the combinations of VH-D-JH genes) causes a bias in the library. The diversity of VHH genes is not only supported by the mechanism of rearrangement of VH-D-JH genes. However, since it is extremely difficult to regenerate a lost portion of germline-derived antibody genes via mutations, the importance of constructing a library maintaining the ratio of germline-derived antibody genes can be understood easily. Therefore, it is questionable whether the lost part of the germline-derived genes can be supplemented by attempts to enlarge the repertoire size by artificially introducing mutations to VHH genes.

In the present invention, whether a library maintains the in vivo diversity can be confirmed as follows. Specifically, when a sufficient amount of clones randomly selected from clones constituting a library are determined to comprise genes of, desirably 6 VHH subfamilies and at the same time 15 or more classes, the library is considered to maintain the in vivo diversity. A sufficient amount of clones used for the analysis is, for example, 50 clones or more.

The VHH libraries of the present invention allow contamination of genes other than VHH genes. Such contamination is unlikely to become an obstacle for obtaining VHHs, particularly when VH is contaminated and VHHs that bind to difficultly recognized antigenic determinants are obtained. This is because even if VHs coexist in the library, their possibility to occupy antigens is low. However, considering that VHH libraries are screened with the expectation of benefits intrinsic to VHHs, it is preferred to avoid the contamination of genes other than VHH genes. Normally, 60% or more, preferably 70% or more, and more preferably 90% or more of the genes of a VHH library of the present invention is VHH genes. When the rate of genes other than VHH genes such as VH increases in the library, under some circumstances, it may decrease the screening efficiency of VHH genes.

VHH genes can be selectively obtained, for example, through amplification of the VHH genes by PCR using the aforementioned primers for VHH gene amplification found by the present inventors. Thus constructed VHH libraries of this invention has a remarkably high component percentage of VHH genes. A preferable VHH library of the present invention comprises VHHs at a rate of, for example, 70% or more, preferably 80% or more, and more preferably 90% or more. More specifically, the present invention relates to a VHH library that comprises IgG2-derived VHHs at a rate of 90% or more, such as 93% or more. Furthermore, the present invention also relates to VHH libraries comprising IgG3-derived VHHs at a rate of 95% or more, preferably 95% or more, and more preferably 99% or more.

(3) In the interest of amplifying VHH genes, collecting amplification products during the progress of exponential amplification Normally, there is an upper limit to the amount of products obtainable by gene amplification reactions as represented by PCR. That is, when the reaction reaches a certain level, amplification reaction stops proceeding. This means that, regardless of the amount of template, the amount of amplification products that are obtainable as a result of an amplification reaction is constant. Antibody genes exist in vivo as a complex assembly of a variety of genes. When such an assembly is used as a template for artificial amplification, the products are often occupied by genes that are dominant in number. This is because the amplification reaction stops at the point where the amplification reaction of the dominant genes reaches the upper limit. When such a phenomenon arises, many of the repertoires will be lost by gene amplification.

The present inventors found that by collecting amplification products during the progress of exponential amplification in the gene amplification reaction, the danger of losing the repertoire through gene amplification could be diminished. While exponential amplification is taking place, all templates can be considered as being amplified at nearly the same probability. Therefore, when amplification products are collected during that phase, the loss of repertoire during the amplification reaction can be kept down to minimum.

Whether exponential amplification is taking place can be confirmed by monitoring the amount of gene amplification products. Particularly, when the progress of reaction is controlled by the number of reaction cycles as in PCR, the amount of amplification products is monitored for each reaction cycle, and the number of cycles necessary for the reaction to reach the upper limit can be elucidated. By performing the amplification reaction in the presence of intercalators such as SYBR green, the amount of amplification products can be monitored according to the changes in fluorescence intensity. Alternatively, an aliquot may be obtained from the reaction solution and subjected to electrophoresis to visually confirm the amplification products.

For example, under the conditions indicated in the Examples, amplification products can be collected during exponential amplification by performing PCR with not more than 17 cycles. In PCR, the state of exponential amplification is determined by various conditions. They are affected by factors, for example, the amount of template genes, the amount of primers, and the kind and amount of DNA polymerase. Therefore, under conditions different from the Examples, exponential amplification may continue even at 17 cycles or more. Whether exponential amplification is taking place under a certain condition can be confirmed as described above.

When VHH genes are amplified under such conditions, the balance among genes in the amplification products reflects the numerical balance among each gene in the template. As a result, the possibility of obtaining numerically dominant genes as well as minor genes increases.

VHH genes obtained under such conditions can be formed into a library according to any method. To use a library of the present invention in the screening based on binding affinity, it is advantageous to construct them as an rgdp library. An rgdp library refers to a replicable genetic display package library. More specifically, it refers to a library that maintains genes, and at the same time presents expression products of the genes on the surface (genetic display package). A representative rgdp library includes a phage library that utilizes the method of phage display. Examples of rgdp libraries include, in addition to the phage library, libraries consisting of transfected cells or ribosomes that express exogenous proteins on their surface.

The phage display method was devised by Smith in 1985 (Smith GP, Science 228(4075), 1315-7 (1985)) using a filamentous bacteriophage having single-stranded circular DNA, such as M13 phage. A phage particle consists of a protein called cp8 and 5 proteins called cp3, both surrounding the DNA of the phage; cp8 constitutes the majority of the phage particle and cp3 functions when the phage infects *E.*

*coli.* A phage display system is a system wherein a gene is constructed so that they encode a polypeptide in the form fused with cp3 or cp8, and the fused protein is expressed on the surface of the phage particle. Phage particles carrying binding proteins on their surfaces can be concentrated using the binding activity with their ligands. Such a method of concentrating the DNA of interest is called "panning". DNA encoding a protein having required binding activity is packaged in the concentrated phage particles. Utilizing a filamentous phage as described above, a system allowing very efficient screening based on binding activity and cloning of DNA was realized (Published Japanese Translation of International Publication No. Hei 5-508076). In the interest of the filamentous phage libraries, a method allowing expression as Fab molecules has been reported (Published Japanese Translation of International Publication No. Hei 6-506836). In this report, the fusion of the variable regions was attempted via a method deleting the N-terminus of cp3 and such.

VHH genes obtained as described above can be made into a phage library, for example, as follows. First, amplification products of VHH genes are treated with restriction enzymes. 5' primers, oligonucleotides having the nucleotide sequences of SEQ ID NOs: 1 to 6, indicated in the Examples comprise a SfiI site. The obtained fragments are inserted into expression vectors for VHH gene transfer that enables expression of fusion proteins with a phage protein. cp3 or cp8 is used as the phage protein, the fusion partner with the VHH genes. In the expression vectors, restriction enzyme sites are prepared to introduce the VHH gene fragments. For example, SfiI-AscI treated fragments of the VHH gene amplification products can be introduced into the SfiI-AscI site of the vectors used in the Examples.

To incorporate VHH genes, Cre recombinase can also be used. Specifically, using primers attached with LoxP sequence, VHH gene amplification products carrying LoxP sequences on both ends are obtained. Then, when LoxP sequence is also placed at the integration site on the expression vector, the amplification products and the vector can be recombined by the action of Cre recombinase.

A vector comprising a gene encoding a phage surface protein such as cp3 and cp8, and a site for VHH gene integration located so as to express the VHH gene as a fusion protein with the phage surface protein is used as the expression vector for VHH gene transfer. For example, a SfiI/AscI site indicated in the Examples can be used as the site for VHH gene integration. According to the analysis by the present inventors, recognition sequences of these restriction enzymes could not be found in camel VHH genes. Therefore, the combination of restriction enzymes, SfiI/AscI, is useful to construct camel VHH gene libraries.

Furthermore, to use a culture supernatant of a host microorganism infected with a phagemid as a sample for screening, an expression vector comprising a promoter and a signal sequence that function in the host microorganism is used. For example, when using *E. coli* as a host, a phagemid vector for filamentous phage inserted with a signal sequence, such as pelB sequence, can be used. Examples of expression vectors useful for constructing the libraries of the present invention include expression vector pFCA-10 indicated in the Examples.

Phage particles expressing a VHH on their surface can be produced by transfecting a VHH gene-integrated expression vector along with a helper phage into a host, and expressing both of them. By collecting these phage particles, a phage library of the present invention can be obtained.

The phrase "helper phage" refers to a phage that infects bacteria transfected with the aforementioned expression vector to provide phage components and produces a phage having a phage surface protein encoded by the expression vector. VHHs will exist on the surface of the phage particle due to the use of a fusion protein derived from the expression vector.

The VHH phage libraries of the present invention find use in screening VHHs by the panning method. The panning method utilizes the binding affinity of VHHs for a substance of interest to select phages that express the VHHs. More specifically, first, a phage library expressing VHHs is contacted with a substance of interest, and phages that bind to this substance are collected. The collected phages are amplified as needed, and are repeatedly contacted with the substance of interest and collected. Using the panning method, phages expressing VHHs having binding affinity for the substance can be obtained. Genes encoding VHHs are packaged in the phages. Therefore, obtaining phages means nothing but simultaneously obtaining genes encoding VHHs.

The VHH libraries of the present invention are libraries with extremely large repertoire sizes that exceed the in vivo diversity of VHHs. Therefore, the use of a VHH library of this invention allows to readily select VHHs with functions that are difficult to obtain by conventional immunological manipulations. For example, as already mentioned, obtaining tetrameric IgG-type antibodies that regulate the activity of an enzyme is often difficult. However, antibodies of VHH constituting dimeric immunoglobulins that regulate enzyme activity may be easily obtained. For example, the Examples successfully employ the VHH libraries of the present invention to yield a plurality of VHHs having the function to regulate the activity of a given enzyme. Thus, the possibility of a non-immunized camel-derived VHH or VH library to provide a plurality of VHH genes having the function to regulate the activity of a given enzyme serves as an index to evaluate the diversity of the library.

As described above, the VHH libraries or VH libraries of the present invention are useful for obtaining VHHs having the function to regulate enzyme activity. Specifically, VHHs or VHs that have the function to regulate enzyme activity can be obtained via the use of an enzyme molecule or a fragment thereof as the aforementioned substance of interest. The fragment of the enzyme molecule can be obtained by fragmenting the enzyme. The enzyme molecule or fragment thereof used for this purpose may be a fusion protein with another protein. Alternatively, a partial sequence of the gene encoding the enzyme can be expressed to use its expression product as the fragment. When the objective is to obtain VHHs or VHs having the function to regulate enzyme activity, the use of a fragment comprising the active site of the enzyme is advantageous. Methods for identifying enzyme active site are well known in the art. Through further confirmation of the action on enzyme molecules, VHHs or VHs selected by the panning method can be ultimately evaluated for their function to regulate the enzyme activity. More specifically, VHHs or VHs to be evaluated are contacted with the enzyme molecule, and when the enzyme activity changes compared to that without this contact, those VHHs or VHs are confirmed to have the function to regulate the enzyme activity. In the present invention, the function to regulate enzyme activity includes inhibition and promotion of enzyme activity.

Genes encoding VHHs or VHs obtained based on the present invention can be translated into immunoglobulins or immunoglobulin fragments using appropriate expression systems. Specifically, the present invention relates to a method for producing an immunoglobulin that comprise camelid-derived VHH as the variable region, or fragments thereof, which comprises the steps of following (1) to (3). Alternatively, using VH instead of VHH, an immunoglobulin comprising VH can be similarly produced.

(1) Obtaining a gene encoding VHH that has the binding activity towards a substance of interest by the above-mentioned method;
(2) producing a VHH expression vector by integrating the obtained gene encoding VHH to a vector that is expressible in a host cell; and
(3) introducing the VHH expression vector into the host cell, and collecting VHH-comprising proteins from the culture.

Genes encoding VHHs obtained from an rgdp library based on the present invention can be collected from VHH expression vectors. For example, the VHH genes of interest can be amplified via PCR using primers used for library construction and expression vectors as templates. Alternatively, when the objective VHH clones can be yielded in large quantities, VHH gene fragments can be excised by restriction enzyme treatment.

The selected VHH genes can be made into complete dimeric immunoglobulins by linking them with a gene encoding the constant region. For example, when utilizing the impairment effect of IgGs on cells and viruses, IgGs comprising the constant region are more advantageous. A safe pharmaceutical formulation is provided by forming a chimeric antibody through the combination of the human constant region. On the other hand, for in vitro diagnostic agents and industrial applications, VHHs can be used as they are. Alternatively, appropriate tags can be attached to VHHs to form fusion proteins. His tags may be used as the tags. His tagged VHHs can be easily purified using nickel column and such. Furthermore, VHHs can be expressed as fusion proteins with a heterogeneous protein, such as GFP or RFP (Morino et al., J. Immunol. Methods 257, 175-184 (2001)).

To express VHH genes as VHHs, or as fusion proteins comprising VHHs, any vector may be used as the expression vector. For example, vectors such as pCANTAB 5E (Amasham), pTZ19R, and pTZ18R are useful for the expression of immunoglobulins. Methods for constructing these vectors are well known in the art. Expression vectors carrying VHH genes can be transformed into hosts that are appropriate for each vector. For example, the aforementioned expression vectors can be transformed into DH12s, TG1, HB2151, and such, to express VHHs. VHHs and immunoglobulins comprising VHHs that are obtained according to the present invention have a variety of uses.

For example, development of diseases due to viruses, bacteria, parasites, or other pathogenic factors can often be avoided by inhibiting enzyme activity of the pathogenic factor or recognition of target molecules by the pathogenic factors via the binding of immunoglobulins. Furthermore, through the binding of immunoglobulins to the active (toxic) site of toxic substances, deleterious effects of the substance can be avoided.

Not only a function to inhibit enzyme activity but also a function to enhance enzyme activity can be expected from camel antibody VHs and VHHs obtained by the present invention. Camel antibody VHs and VHHs having such functions are also expected to suppress exacerbation of symptoms, alleviate pathologic pains, or cure integrated dysfunction of complexed enzymatic or physiological processes due to the disorder of enzyme function or protein recognition.

Furthermore, enzyme inhibitory antibodies obtained by the present invention can be used to evaluate enzyme activity. Specifically, when an enzyme inhibitory antibody inhibits a certain enzyme activity in a sample, the existence of an enzyme that is inhibited by the enzyme inhibitory antibody can be elucidated. By correlating the added amount of the enzyme inhibitory antibody and the inhibition level, the level of enzyme activity in the sample can be quantitatively evaluated.

In addition, antibodies obtained by the present invention having the function to enhance enzymatic activity find use in detecting enzyme activity. Specifically, a detection system wherein a small amount of enzyme activity is amplified with an antibody that has the function to enhance the enzymatic activity may be constructed. The present invention provides testing and measuring kits for enzyme activity, and diagnostic techniques that use the antibodies obtained by the present invention.

Furthermore, the antibodies obtained by the present invention having the function to regulate enzyme activity can be used in industrial enzymatic reactions. For example, the yield of an objective product of an enzymatic reaction system can be increased by colocalizing antibodies that promote enzyme activity. Conversely, the yield of products can be also increased by colocalizing antibodies that suppress enzyme activity consuming the objective product of interest in the enzymatic reaction system. Moreover, the purity of products is expected to be increased via the suppression of enzyme activity generating undesirable by-products.

All references cited herein are incorporated by reference into the present application.

BRIEF DESCRIPTION OF THE DRAWINGS

FIG. 2 shows the nucleotide sequence of the expression vector pFCA-10 for camel VHH integration and the amino acid sequence encoded by its protein-coding region.

FIG. 16 shows the nucleotide sequence of the insert in scNcopFCAH9-E8VHdVLd and the amino acid sequence encoded thereby (continued to FIG. 17).

FIG. 17 shows the nucleotide sequence of the insert in scNcopFCAH9-E8VHdVLd and the amino acid sequence encoded thereby (continued from FIG. 16).

FIG. 19 shows the nucleotide sequence of the insert in pscFvCA-E8VHd and the amino acid sequence encoded thereby (continued onto FIG. 20).

FIG. 20 shows the nucleotide sequence of the insert in pscFvCA-E8VHd and the amino acid sequence encoded thereby (continued from FIG. 19).

BEST MODE FOR CARRYING OUT THE INVENTION

The present invention will be described in detail below with reference to the Examples.

EXAMPLE 1

Construction of Camel Antibody Library 1-1. Confirmation of Restriction Enzyme Sites in Camel Germline and Primer Designing In the following Examples, New England biolabs or buffers produced by this company will be indicated as NEB. The absence of sites cleavable with SfiI or AscI restriction enzyme used for subcloning into a vector was confirmed in the germlines of camel VH or VHH by referring to a reference (Nguyen et al., EMBO J. 19(5), 921 (2000)). Six kinds of primers for the N-terminus of the V region covering the germlines of VH and VHH were constructed. The nucleotide sequences of the primers are shown in SEQ ID NOs: 1 to 6.

```
(1) VHH3a (SEQ ID NO: 1)
GTCCTCGCAACT GCG GCC CAG CCG GCC ATG GCC GAG GTG

CAG CTG GTG GAG TGT GG (2) VHH-germF1 (SEQ ID NO: 2)
GTCCTCGCAACT GCG GCC CAG CCG GCC ATG GCC CAG GTR

CAG CTG GTG GAG TCT GG (3) VHH-germF2 (SEQ ID NO: 3)
GTCCTCGCAACT GCG GCC CAG CCG GCC ATG GCC CAG GTA

AAG CTG GAG GAG TCT GG (4) VHH-germF4 (SEQ ID NO: 4)
GTCCTCGCAACT GCG GCC CAG CCG GCC ATG GCC GAT GTG

CAG CTG GTG GAG TCT GG (5) VHH-germF5 (SEQ ID NO: 5)
GTCCTCGCAACT GCG GCC CAG CCG GCC ATG GCC GCC GTG

CAG CTG GTG GAT TCT GG (6) VHH-germF6 (SEQ ID NO: 6)
GTCCTCGCAACT GCG GCC CAG CCG GCC ATG GCC GCG GTG CAG CTG GTG GAG TCT GG
* Sfi I sites are underlined.
```

Next, C-terminal primers of the V region were designed.

Considering the convenience during screening, VHs (IgG1) that may cause aggregation were removed as possible from the camel library constructed herein. Therefore, IgG1 was removed and IgG2 and IgG3 were selectively included in the library. For this purpose, sequences absent in IgG1 but existing in IgG2 and/or IgG3 alone had to be used as primers.

Accordingly, the present inventors focused on the differences in the sequences of the hinge regions existing on the C-terminal side of the V region. The previously obtained hinge region of camel IgG1 gene (PCR product of 800 bp) was analyzed and compared with IgG2 and IgG3. As a result, the amino acid sequences in this region showed the following differences.

```
tetrameric camel antibody:
IgG1 hinge  EPHGG                              CPCPKCP  (SEQ ID NO: 7)

dimeric camel antibody:
IgG2 hinge  EP KI PQPQPKPQPQPQPQPKPQPKPEPE    CTCPKCP  (SEQ ID NO: 8)

IgG3 hinge  GT N EV                            CKCPKCP  (SEQ ID NO: 9)
```

Based on these results, primers that selectively amplify IgG2 and IgG3 were designed by determining the N-terminal nucleotide sequence of the hinge regions existing on the C-terminal side of the V region. The nucleotide sequences of the C-terminal (3'-side) primers that were thus determined are shown in SEQ ID NO: 10 (IgG2-LB1) and SEQ ID NO: 11 (IgG3-LB2).

```
IgG2-LB1 (SEQ ID NO: 10):
AA G GCG CGC CCC TTG GGG TAT CTT GGG TTC TG

IgG3-LB2 (SEQ ID NO: 11):
AA G GCG CGC CCC TGA TAC TTC ATT CGT TCC TGA VG AG
```

1-2. Cloning Vector for Library

Figure 1:
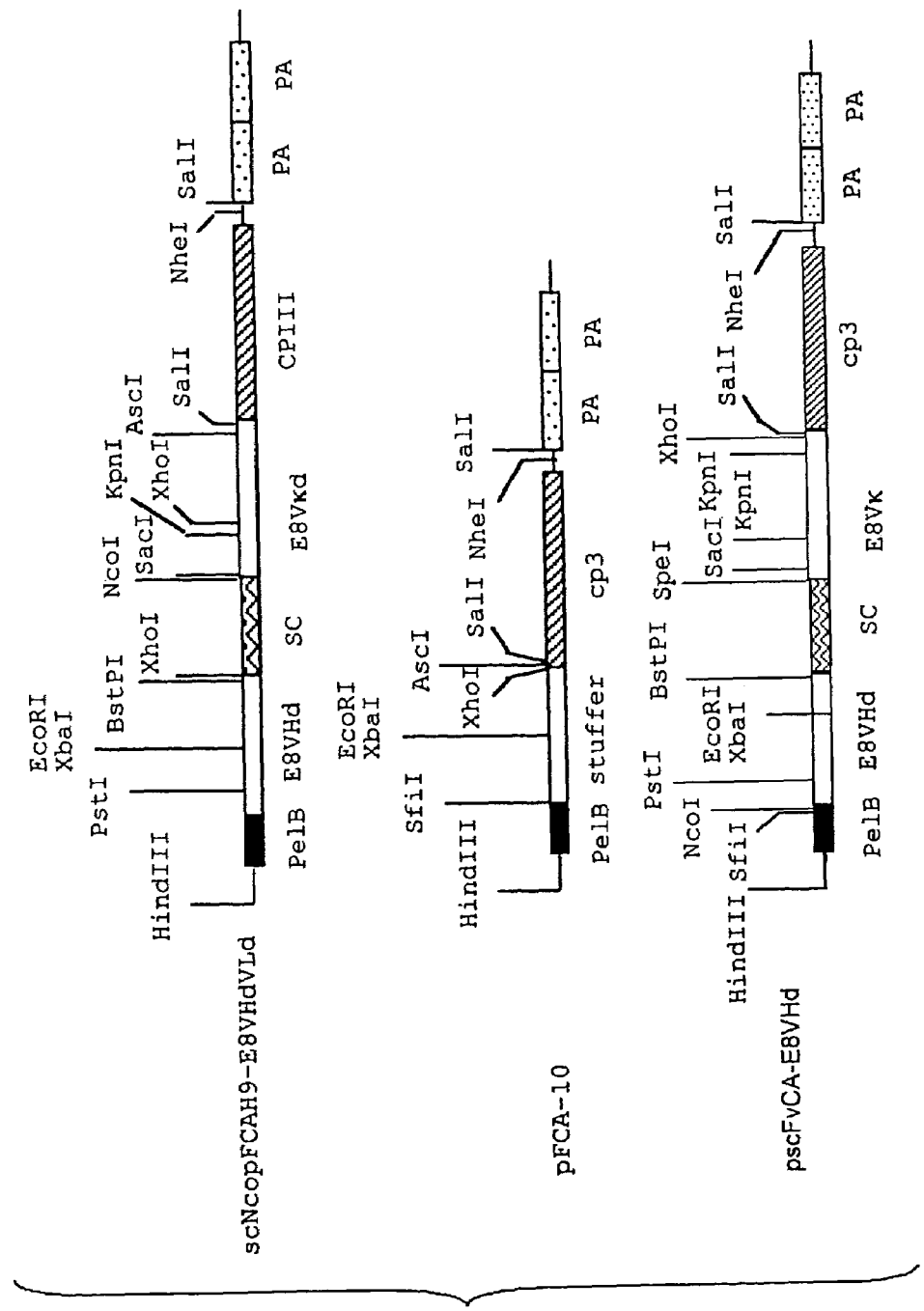
FIG. 1 shows the structures of the vector for camel antibody library (pFCA-10) and known vectors (pscFvCA-E8VHd vector and scNcopFCAH9-EBVHdVLd vector) used for its construction.

First, an expression vector inserted with a stuffer sequence into the SfiI-AscI site wherein a VHH gene is integrated was constructed. The structures of pscFvCA-E8VHd vector, scNcopFCAH9-E8VHdVLd vector, and expression vector pFCA-10 for camel VHH integration, all used for vector construction, are shown in FIG. 1. In addition, the nucleotide sequence of pFCA-10 and the amino acid sequence encoded by its protein-coding region are shown in FIG. 2. The vectors were designed so as not to express cp3, when the restriction enzyme failed to cleave the vector or the antibody gene had not been integrated. scNcopFCAH9-E8VHdVLd and pFCA-10 were constructed as described below.

1-2-1. Construction of scNcopFCAH9-E8VHdVLd

Three µg (3 µL) of pFCAH9-E8d (see WO 01/62907) was mixed with 3 µL of BstPI (3 U/µL), 5 µL of 10×H buffer, and 39 µL of distilled water (DW), and restriction enzyme treatment was performed at 37° C. for 2 hr. After the treatment, the precipitate obtained by ethanol precipitation was dissolved in 10 µL of TE buffer. One µL of SacI (10 U/µL), 5 µL of 10×L buffer, and 34 µL of DW were mixed for restriction enzyme treatment at 37° C. for 2 hr, and then a 4.7 kb fragment was collected by agarose gel electrophoresis. The collected fragment was subjected to ethanol precipitation and adjusted to 10 µL (pFCAH9-E8d BstPI-SacI fragment).

Meanwhile, 5 µL of linF primer (100 pmol/µL) and 5 µL of linR primer (100 pmol/µL) were mixed. The mixture was heated at 94° C. for 5 min, incubated at 80° C. for 5 min, 70° C. for 5 min, and then left at room temperature for 30 min to be annealed. Two µL of this solution, 1 µL of the pFCAH9-E8d BstPI-SacI fragment obtained above, 1.5 µL of 10× ligation buffer, 9.5 µL of DW, and 1 µL of T4DNA ligase were mixed and reacted at 16° C. for 16 hr. After the reaction, the mixture was concentrated to 3 µL by ethanol precipitation, and 1.5 µL thereof was used to transform 20 µL of E. Coli DH12S competent cells by electroporation. The plasmid of the obtained clone was extracted, its nucleotide sequences was confirmed, and the plasmid was dubbed scNcopFCAH9-E8VHdVLd. A schematic illustration of the structure of scNcopFCAH9-E8VHdVLd is shown in FIG. 1 (top). Furthermore, the nucleotide sequence of the insert region of scNcopFCAH9-E8VHdVLd and the amino acid sequence encoded thereby are shown in FIGS. 16 and 17. In addition, the nucleotide sequence of the insert region of pscFvCA-E8VHd and the amino acid sequence encoded thereby are shown in FIGS. 19 and 20.

```
linF primer (SEQ ID NO: 36)
GTCACCGTCTCGAGAGGCGGTGGCGGATCAGGTGGCGGTGGAAGTGGCGG

TGGTGGGTCCATGGCCGACATCGAGCT linR primer (SEQ ID NO: 37)
CGATGTCGGCCATGGACCCACCACCGCCACTTCCACCGCCACCTGATCCG

CCACCGCCTCTCGAGACG
```

1-2-2. Construction of Vector (pFCA-10) for Camel Antibody Library

Two µg of scNcopFCAH9-E8VHdVLd vector (10 µL), 10 µL of 10×M buffer, 78 µL of DW, and 2 µL of HindIII (12 U/µL; Takara) were mixed and incubated at 37° C. for 2 hr, concentrated by ethanol precipitation, and dissolved in 10 µL of TE. Subsequently, 10 µL of 10×NEB4 buffer (supplied with AscI), 78 µL of DW, and 2 µL of AscI (10 u/µL; NEB) were added thereto, incubated at 37° C. for 2 hr, concentrated by ethanol precipitation, and electrophoresed on agarose gel to collect a fragment of interest (3.7 kb). The fragment was purified using GENECLEAN II Kit (Funakoshi), concentrated by ethanol precipitation, and dissolved in 10 µL of 1/10 TE.

Next, 0.1 µg of pscFvCA-E8VHd vector (5 µL), 1 µL of M13RV primer (100 pmol/µL, 5'-AACAGCTATGAC-CATG-3'; SEQ ID NO: 12/Sawady Technology), 1 µL of XhoAsc primer (100 pmol/µL, 5'-CGACTGAAG-GCGCGCCCCTCTCGAGACCCTGACCGTGGTGCC-3'; SEQ ID NO: 13/Sawady Technology), 10 µL of 10× buffer #1 (supplied with KOD), 10 µL of dNTP mix (supplied with KOD), 4 µL of 25 mM MgCl$_2$, 68 µL of DW, and 1 µL of KOD polymerase (2.5 u/µL; TOYOBO) were mixed on ice, 2 drops of mineral oil were added and warmed at 94° C. for 2 min. Subsequently, treatment at 94° C. for 1 min, 55° C. for 2 min, and 72° C. for 1 min was repeated for 25 cycles. The obtained PCR product was confirmed by agarose gel electrophoresis. Then, a band near 400 bp was cut out, purified using GENECLEAN II Kit (Funakoshi), ethanol precipitated, and then suspended in 10 µL of TE.

10 µL of 10×M buffer, 78 µL of DW, and 2 µL of HindIII (12 U/µL; Takara) were mixed to the above DNA solution. The mixture was incubated at 37° C. for 2 hr, and concentrated by ethanol precipitation, and then dissolved in 10 µL of TE. Subsequently, 10 µL of 10×NEB4 buffer (supplied with AscI), 78 µL of DW, and 2 µL of AscI (10 U/µL; NEB) were mixed thereto, incubated at 37° C. for 2 hr, concentrated by ethanol precipitation, and then electrophoresed on agarose gel. The band near 340 bp was collected, purified using GENECLEAN II Kit (Funakoshi), concentrated by ethanol precipitation and then dissolved in 10 µL of 1/10 TE. To a half of this solution, 5 µL, 2 µL of the HindIII-AscI fragment of the scNcopFCAH9-E8VHdVLd vector, 2 µL of 10× ligation buffer, 2 μL of 10 mM ATP, 8 μL of DW, and 1 μL of T4 DNA ligase were added and mixed, and the mixture was incubated at 16° C. for 16 hr. This was ethanol precipitated and dissolved in 3 μL of 1/5 TE. Then, half thereof was suspended in 20 μL of ElectroMAX™ DH12S (Invitrogen) competent cells to achieve transformation via electroporation under following conditions:

| Electroporator BRL Cell-Porator (Cat. series 1600) | | |
|---|---|---|
| setup conditions; | voltage booster | 4 kΩ |
|  | capacitance | 330 μF |
|  | DC volts | Low Ω |
|  | charge rate | Fast |

Twelve obtained transformants were cultured in LBGA at 30° C. for 18 hr, plasmids were extracted using KURABO DNA Isolation System PI-50, and their nucleotide sequences were confirmed. The sequences were determined by the dideoxy method using M13 Reverse fluorescent primer (cat. No. LIC-4000-21B; ALOKA), Thermosequence kit (Amersham Pharmacia), and ALOKA L1-COR4200L(S)-2. As a result, all sequences were as designed. One of them (No. 1) was prepared from 400 mL of culture medium by the alkaline method, and then purified by CsCl density gradient ultracentrifugation to yield 210 μg of plasmid. It was named pFCA-10, and used as a vector for camel antibody library.

1-3. Preparation of Total RNA from Frozen Spleen (Guanidine Ultracentrifugation Method)

Approximately 9 g of frozen spleen from dromedaries (*Camelus dromedarius*) was finely crushed with a hammer. After measuring the weight, 45 ml of GTC solution (450 μL of 2-mercaptoethanol added right before use to 4.0 M guanidinethiocyanate and 0.1 M Tris-HCl (pH 4.5)) was added immediately, and was further fragmented in an ice-cold nissei Excel Auto Homogenizer at 17,000 rpm for 2 min. Next, it was completely homogenized with a Teflon homogenizer to remain connective tissue debris alone. The homogenate solution was filtered through gauze.

0.23 g of N-lauroylsarcosin sodium salt was added as a powder to the filtered solution, and was dissolved well. DNA therein was fragmented by shearing force due to passages of the solution through needles attached to a syringe, which involved 3 passages through 18G, 5 passages through 21G, and 5 passages through 22G needles.

The precipitates were removed by centrifugation at 5,000 rpm for 10 min at. room temperature. The solution was approximately 36 ml. HITACHI Centrifuge Ware 13PA tube was washed with diothylpyrocarbonate (DEPC) treated water, 4 mL of CsCl solution (5.7 M CsCl, 0.01 M EDTA) was placed therein, and 6 ml of supernatant was layered without disturbing the interface. Ultracentrifugation was performed on HITACHI HIMAC55P-72 using RP40T-740 rotor at 30,000 rpm for 20 hr. (Except TES solution (10 mM Tris-HCl, 5 mM EDTA, 1% SDS), reagents used for following steps were all treated with DEPC, and operations were carried out with utmost care to avoid contamination by ribonucleases.)

After centrifugation, the upper layer was carefully removed (Pasteur pipettes were frequently exchanged). When the remaining upper layer became approximately 0.5 mL, the tube was inverted to discard the remaining solution. Using a heated razor blade, near 1 cm from the bottom of the tube containing RNA precipitate was cut, and the precipitate was rinsed with 75% ethanol and air-dried. The precipitate was dissolved in TES solution, 1/10 volume of 3M sodium acetate (pH5.2) and 2.5 volume of ethanol were added for precipitation, and the precipitate was stored at −80° C. until use.

Total RNA was obtained by guanidine ultracentrifugation from spleens of 22 camels according to similar steps described above. mRNA was prepared from each of thess total RNAs using commercially available oligo-dT column kit (Pharmacia mRNA Purification Kit (oligo-dT column method)). The yield of mRNA was about 1% of the total RNA.

1-4. Construction of Heavy Chain Variable Region Antibody Libraries for VHH Selection 1-4-1. Preparation of cDNA One μg each of mRNA derived from each camel was mixed to form a library template. cDNA was prepared by reverse transcriptase reaction on the mRNA using a random primer (N6, Gibco BRL) and following the instructions for Superscript (Gibco BRL).

The incorporation of [α-$^{32}$P]dCTP was measured at real time to reveal a [α-$^{32}$P]dCTP incorporation of 2.4% and a transcription rate of 15.8%. Calculating from the incorporation rate, 3.3 μg of cDNA was obtained from 22 μg of mRNA.

1-4-2. PCR for Construction of Libraries, and Collection of VHH Gene Fragments

Separate libraries were constructed for IgG2 and IgG3, respectively, as heavy chain variable region antibody libraries for VHH selection. To construct libraries reflecting the germline ratio expressed in 22 camels, PCR amplification process was monitored and amplification products were collected in the exponential phase. The PCR amplification process was stopped at every few cycles to monitor the DNA level by quantification. Even for diversified fragments, a group of gene fragments accurately reflecting the repertoire before the amplification should be obtained by collecting them while exponential gene amplification is taking place.

Figure 3:
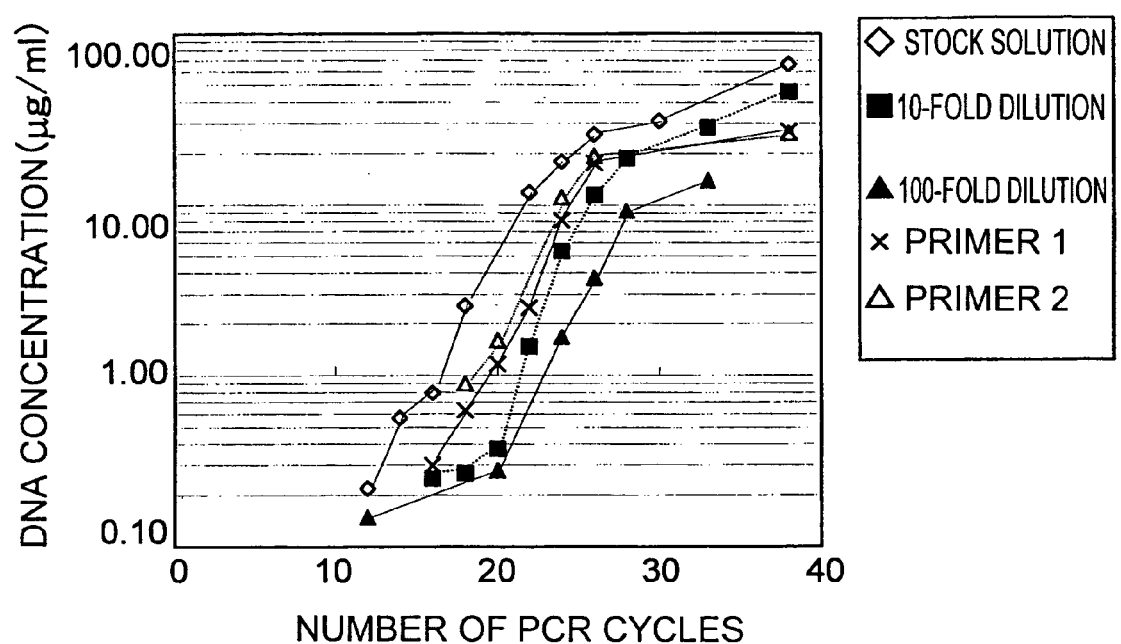
FIG. 3 shows the result of monitoring the amount of amplification products in each reaction cycle of PCR. Control DNA stock solution, its 10-fold dilution, or 100-fold dilution was used as the template. The vertical axis shows the amount of DNA (μg/mL) on a logarithmic scale and the horizontal axis shows the number of PCR cycles.

Stock solution of control DNA constructed by ligating a camel antibody gene into Bluescript vector, 10-fold diluted and 100-fold dilutions thereof were used as templates to confirm gene amplification (FIG. 3). Here, VH3a primer (SEQ ID NO: 1) was used as the N-terminal primer, and "J primer" (5'-AA GGCGCGCCCC TGA VGA GRY GGT GAC YHG-3'; mixed nucleotides as, V: ACG, R: AG, Y: CT, and H: ACT; SEQ ID NO: 42) constructed based on the J gene was used as the C-terminal primer. Similar experiments were performed, wherein the N-terminal primer was changed to VHH-germ F1 (SEQ ID NO: 2) or VHH-germF2 (SEQ ID NO: 3) and control DNA stock solution was used as a template. These results are also shown in FIG. 3 as primer l and primer 2, respectively.

The reaction was stopped at every few cycles and a portion of the reaction solution was sampled. After staining with Picogreen (Gibco BRL), DNA was quantified using a fluorophotometer. At stages where the DNA concentration is low, such as up to the 20th cycle of the 10-fold dilution or 100-fold dilution, the apparent amplification rate seemed low in certain cases due to measurement noise. However, up to approximately 27 cycles, exponential amplification could be confirmed.

Figure 4:
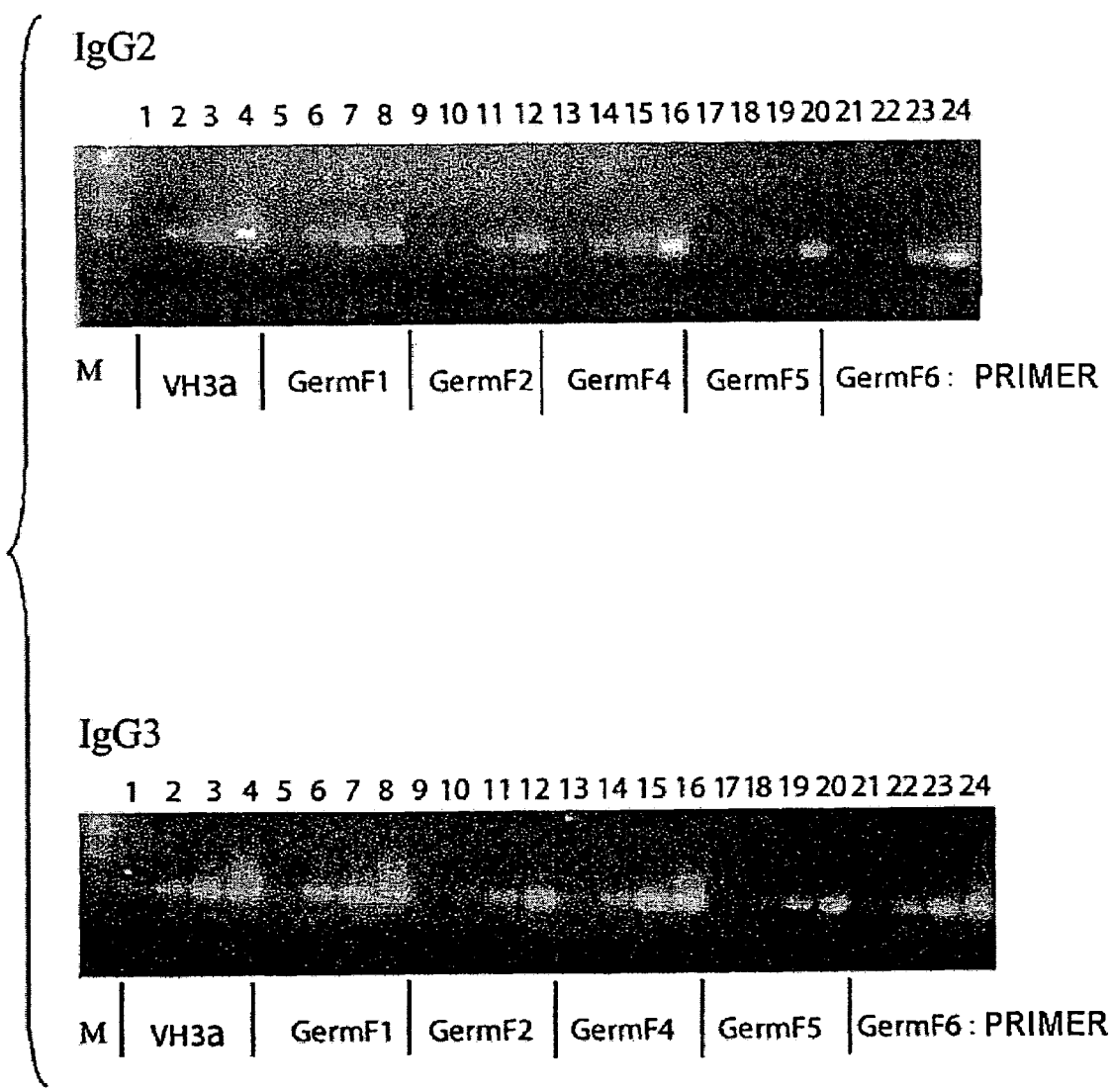
FIG. 4 is a set of photographs showing the result of electrophoresis of amplification products at each reaction cycle of PCR using camel antibody cDNA as the template. The names of the 5' primers are indicated under the photographs. From the left for each of the primers, amplification products of the 15th, 17th, 19th, and 21st cycle were eledtrophoresed. The results of using primers for IgG2 and primers for IgG3 as 3' primers are shown in the upper and lower photographs, respectively.

Next, cDNA actually obtained in 1-4-1 and primers of SEQ ID NOs: 1 to 6 were used for gene amplification. The reaction was stopped at 15th, 17th, 19th, and 21st cycles and 2 μL of each of the reaction solutions was electrophoresed. As a result, the reaction did not reach saturation at least up to the 19th cycle (FIG. 4).

According to the above-mentioned results, 17 cycles of PCR reactions were carried out on the same amount of cDNA using combinations of 6 types of 5' primers with 2 types of 3' primers (IgG2 LB1 or IgG3 LB2).

The PCR conditions were as follows:

| LA Taq (Takara) | 0.5 μL |
| 10× LA buffer (Takara; supplied with LA Taq) | 10 μL |
| 25 mM MgCl$_2$ (Takara; supplied with LA Taq) | 10 μL |
| dNTP (Takara; supplied with LA Taq) | 16 μL |
| sterilized MilliQ water | 61.5 μL |
| Template cDNA | 1 μL |
| 5' primer (100 pmol/μL) | 0.5 μL |
| 3' primer (100 pmol/μL) | 0.5 μL |

Any one of VH3a (SEQ ID NO: 1), VHH-germF1 (SEQ ID NO: 2), VHH-germF2 (SEQ ID NO: 3), VHH-germF4 (SEQ ID NO: 4), VHH-germF5 (SEQ ID NO: 5), and VHH-germF6 (SEQ ID NO: 6) was used as the 5' primer. Furthermore, either IgG2LB1 (SEQ ID NO: 10) or IgG3LB2 (SEQ ID NO: 11) was used as the 3' primer. PCR was performed on all combinations of these primers (6 types of 5' primers×2 types of 3' primers=12 combinations).

50 μL of mineral oil (SIGMA) was layered on the above-mentioned reaction solution in 110 of 0.5-mL tubes when VHH-germF1 was used as the 5' primer, and in 55 tubes in other cases. After incubating the solution at 94° C. for 3 min, 17 cycles of amplification at 94° C. for 1 min, 61° C. for 2 min (59° C. when using IgG3LB2), and 72° C. for 1 min were performed. PCR amplification fragments of 6 types of IgG2, or 6 types of IgG3 were mixed respectively and electrophoresed. The bands comprising the fragment of interest were cut out and collected using QIAEXII (QIAGEN). For IgG3 and IgG2, 48 μg and 25 μg of PCR fragments were collected, respectively.

1-4-3. Insertion of PCR-amplified Gene Fragments into Library Vector

Enzyme fragmentation and ligation conditions are shown below.

(1) SfiI (NEB) cleavage and TsAP (Gibco BRL) treatment of library vector pFCA-10

| vector | 100 μg |
| NEB No. 2 | 200 μL |
| 10× BSA (Takara) | 200 μL |
| SfiI 10 U/μL | 100 μL |
| TsAP 1 U/μL | 20 μL | adjusted to 2000 μL using sterilized MilliQ water

Reaction solution with the above-mentioned composition was layered with mineral oil and was reacted at 50° C. for 5 hr. Successively, following components were further added for TsAP treatment.

| NEB No. 2 | 10 μL |
| 10× BSA (Takara) | 10 μL |
| DW | 40 μL |
| TsAP 1 U/μL | 40 μL |

After reacting at 65° C. for 30 min, stop solution was added to the reaction solution and was heated at 65° C. for 20 min to inactivate the enzymes. The mixture was treated twice with phenol-chloroform and then once with chloroform. The resulting solution was concentrated to 1 mL by butanol, 210 μg of glycogen was added, and then ethanol precipitated to collect 105 μg of vector.

Subsequently, by the following operation, PCR amplification products of IgG2 or IgG3 were cleaved with SfiI.

| PCR fragment | 25.0 μg |
| NEB No. 2 | 50 μL |
| 10× BSA (Takara) | 50 μL |
| SfiI 10 U/μL | 25 μL | adjusted to 200 μL with sterilized MilliQ water

The reaction solution was layered with mineral oil and reacted at 50° C. for 3 hr. Phenol-chloroform treatment was performed followed by chloroform treatment and ethanol precipitation. Twenty-two μg of IgG2 and 23.8 μg of IgG3 were collected.

(2) Ligation of the SfiI Portions

| SfiI cleaved fragments of IgG2 or IgG3 PCR amplification product | 8 μg |
| SfiI-cleaved library vector pFCA-10 | 40 μg |
| 10 mM DTT | 40 μL |
| 10 mM ATP | 40 μL |
| 10× ligase buffer (Takara, supplied with T4 DNA Ligase) | 40 μL |
| T4 DNA Ligase (Takara) 350 U/μL | 40 μL | adjusted to 400 μL with sterilized MilliQ water

The reaction solution was incubated at 16° C. for 13 hr, and at this point, following factors were supplemented.

| DW | 120 μL |
| 10 mM DTT | 20 μL |
| 10 mM ATP | 20 μL |
| 10× Ligase buffer | 20 μL |
| T4 DNA Ligase (Takara) 350 U/μL | 20 μL |

This solution was further reacted at 16° C. for 6.5 hr, subjected to phenol-chloroform treatment, and concentrated to 230 μL with butanol. 70 μg of glycogen was added thereto, and subjected to ethanol precipitation to obtain 34.1 μg of IgG2 ligation DNA or 29.7 μg of IgG3 ligation DNA.

(3) AscI Cleavage

The collected IgG2 ligation DNA (34.1 μg), or IgG3 ligation DNA (29.7 μg) was treated with a reaction solution with following composition at 37° C. for 3 hr.

| NEB No. 4 | 61 μL |
| AscI (NEB) 10 U/μL | 50 μL | adjusted to 610 μL with sterilized MilliQ water

After the reaction, the solution was subjected to phenol-chloroform treatment, and concentrated to 200 μL with butanol. 70 μg of glycogen was added thereto, and subjected to ethanol precipitation to obtain 25 μg of IgG2 ligation product or 29 μg of IgG3 ligation product.

(4) Ligation of the AscI Portions

25 μg of collected DNA of the IgG2 ligation product, or 29 μg DNA of the IgG3 ligation product was treated with a reaction solution with following composition.

| | |
|---|---|
| 10 mM DTT | 750 μL |
| 10 mM ATP | 750 μL |
| 10× ligase buffer | 750 μL |
| T4 DNA Ligase (Takara) 350 U/μL | 375 μL |
| adjusted to 7500 μL with sterilized MilliQ water | |

After 16 hr of treatment at 16° C., the solution was concentrated to 600 μL using CENTRICON YM-10 (10,000 molecular weight cut-off, AmiCon), and subjected to phenol-chloroform treatment. 70 μg of glycogen was then added thereto and subjected to ethanol precipitation to obtain 23.7 μg of IgG2 ligation product or 27.8 μg of IgG3 ligation product.

Figure 5:
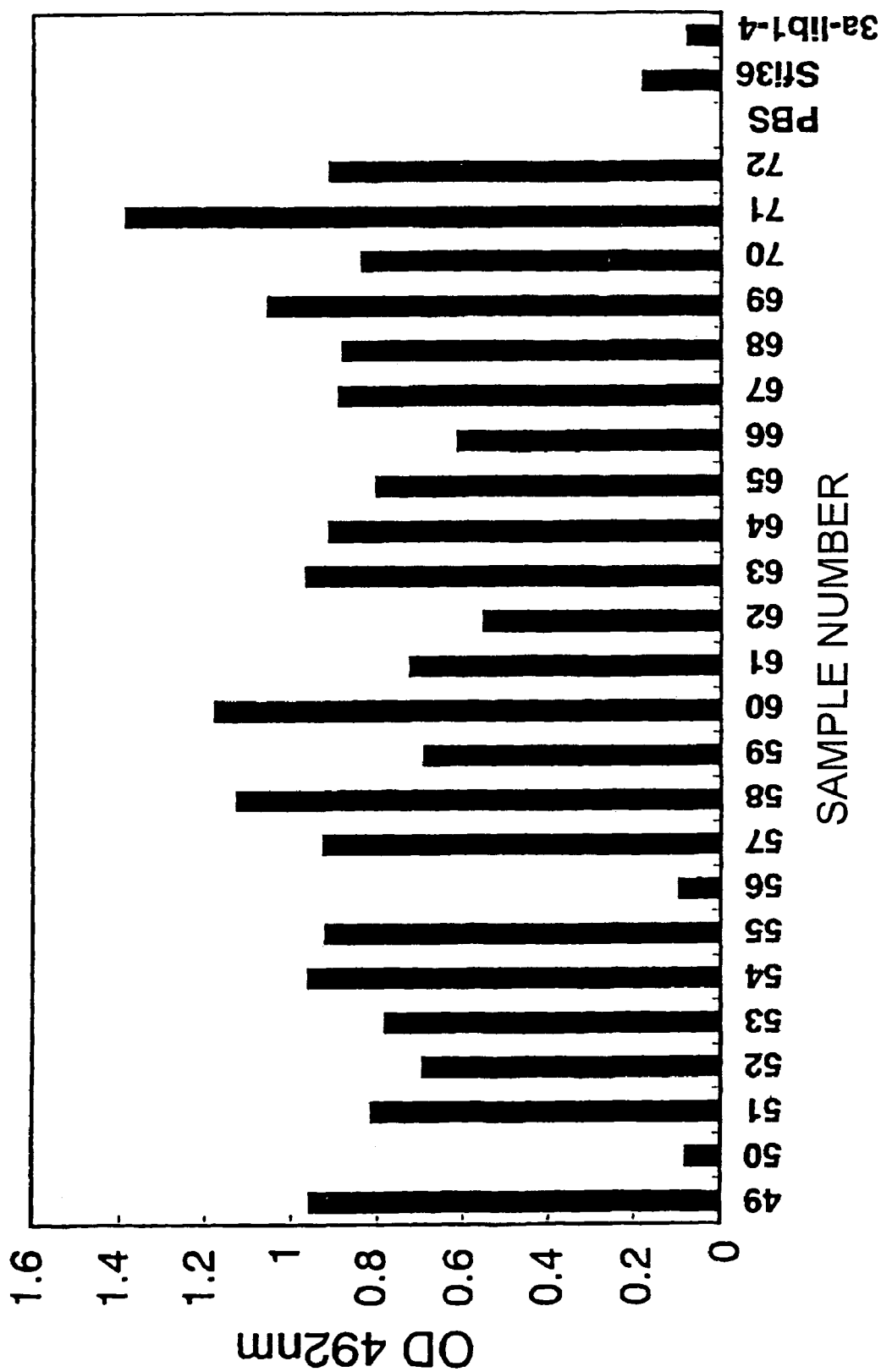
FIG. 5 shows the result of confirming VHH-cp3 expression in ElectroMAX™ DH12S (Invitrogen) transfected with camel VHH gene (IgG2)-integrated expression vectors. The vertical axis shows the absorbance (OD 492 nm), and the horizontal axis shows the sample number.

1-4-4. Confirmation of Library Expression 0.2 μg of the expression vector incorporating camel VHH genes constructed as described above was transformed into 20 μL of ElectroMAX™ DH12S (Invitrogen). The culture supernatant of the transformants was sampled to confirm the expression of VHH-cp3. Since pFCA-10 comprises pelB secretion signal sequence, a small amount of VHH-cp3 protein of the phage is produced into the culture supernatant of E. coli transformed with this vector. Therefore, by monitoring the culture supernatant by ELISA, the expression of VHH-cp3 can be confirmed. As a result of monitoring the expression of VHH-cp3 in the culture supernatant by ELISA, 90% expressed VHH-cp3. The results of monitoring by ELISA are indicated in FIG. 5 (IgG2) and FIG. 6 (IgG3). Specific protocols for ELISA were as described below.

Figure 6:
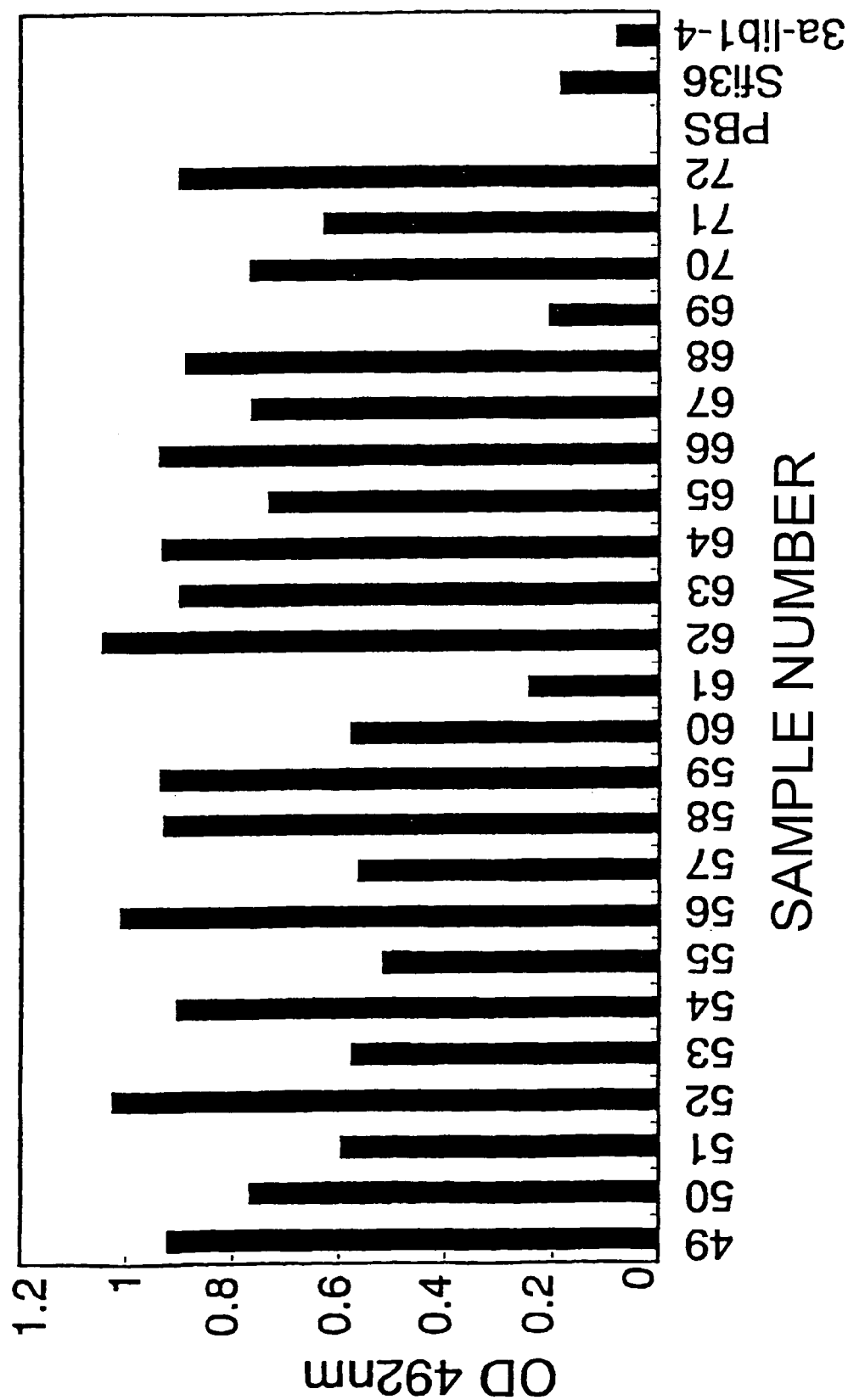
FIG. 6 shows the result of confirming VHH-cp3 expression in ElectroMAX™ DH12S (Invitrogen) transfected with camel VHH gene (IgG3)-integrated expression vectors. The vertical axis shows the absorbance (OD 492 nm), and the horizontal axis shows the sample number.

The expression was induced by the addition of 1 mM IPTG in the early stage of exponential growth phase. After 21 hr, the culture was centrifuged and the collected culture supernatant was used to sensitize MaxiSorp™. 500-fold-diluted rabbit anti-cp3 antibody was used as the primary antibody and 10,000-fold-diluted HRP-conjugated anti-rabbit IgG (H+L chain) goat Fab' was used as the secondary antibody. For measurement of HRP activity, 100 μL of ortho-phenylenediamine and hydrogen peroxide solution were added and reacted for 10 min. The reaction was quenched by adding 100 μL of 2N sulfuric acid, and the absorbance at a wavelength of 492 nm was measured. 3a-lib1-4 and Sfi36 on the right ends in FIGS. 5 and 6 show the results of frame shift mutation (negative control).

1-4-5. Transformation of Heavy Chain Variable Region Antibody Libraries (IqG2 and IqG3 Libraries) for VHH-Type Selection E. coli was transformed via electroporation under following conditions to introduce phage genes.

Electroporator

| Electroporator BRL Cell-Porator (Cat. series 1600) | | |
|---|---|---|
| setup conditions; | voltage booster | 4 kΩ |
| | capacitance | 330 μF |
| | DC volts | Low Ω |
| | charge rate | Fast |

For IgG2, 23.7 μg of DNA obtained by ligation was used to transform 2 mL of DH12S cells (0.2 μg each of DNA was electroporated into 20 μL of ElectroMAX™ DH12S (Invitrogen)). A portion of these cells was sampled to estimate the overall number of transformed bacteria as $1.7 \times 10^{10}$. These cells were stored as glycerol stock, and 20-L scale of phage preparation was carried out.

Specifically, 100 μg/mL of ampicillin was added to 4.8 L of sterilized 2×TY (DIFCO) medium, and the glycerol stock was added to adjust the absorbance at wavelength 600 nm to the vicinity of 0.3. This solution was divided into 16 portions of 300 mL, cultured with shaking in a sterilized 5 L flask at 37° C. until the absorbance at 600 nm reached 1.0. Three mL of helper phage (M13K07) per flask was added to the culture, and cultured at 37° C. for 1 hr. 900 mL of sterilized 2×TY medium, 0.9 mL of 100 μg/mL ampicillin, and 1.2 mL of 50 μg/mL of kanamycin were added to each flask and cultured with shaking at 37° C. for 17 hr.

During the culture, the number of bacteria at the time of helper phage infection was $5.66 \times 10^{11}$ and infectivity of the helper phage was 75% (there were $4.06 \times 10^8$ cfu/ml of ampicillin-resistant bacteria and $3.05 \times 10^8$ cfu/mL of ampicillin- and kanamycin-resistant bacteria during helper phage infection). The goal to obtain $10^{10}$ or more independent clones was achieved.

To collect the phages, the bacterial solution was centrifuged at 10,000 rpm for 10 min at 4° C. to collect the supernatant. 4 L of 20% polyethylene glycol/2.5 M NaCl was added to the supernatant and was gently stirred for approximately 20 min.

This solution was centrifuged at 10,000 rpm for 10 min at 4° C. and the precipitate was dissolved in 1 L of PBS. 200 mL of 20% polyethylene glycol/2.5M NaCl was added thereto, and gently stirred for approximately 20 min. After centrifugation at 10,000 rpm for 5 min at 4° C., the supernatant was discarded. The residue was further centrifuged at 10,000 rpm for 1 min at 4° C., and the precipitate was collected. The precipitate was dissolved in 20 mL of PBS containing 0.05% $NaN_3$ to form a library phage solution.

Next, the titer of the collected phage was checked as follows. Specifically, $10^6 /10^7$, and $10^8$-fold dilution of the phage solution was prepared with PBS, 10 μL each was used to infect 990 μL of DH12S cells, and the cells were cultured at 37° C. for 1 hr. 100 μL of the culture was seeded on LBGA plate, cultured at 30° C. for 18 hr, and the stock solution titer was estimated from the colony count. As a result, 20 mL of library phage having a titer of $3.73 \times 10^{13}$ CFU/mL was obtained.

For IgG3, 27.8 μg of DNA obtained by ligation was used to transform 2 mL of ElectroMAX™ DH12S (Invitrogen) by electroporation (0.2 μg each was introduced into 20 μL of ElectroMAX™ DH12S (Invitrogen)). A portion of the cells was sampled to estimate the overall number of transformed bacteria as $1.1 \times 10^{10}$. The preparation was carried out similarly to IgG2.

During culturing, the number of bacteria at the time of helper phage infection was $8.64 \times 10^{11}$ and infectivity of the helper phage was 78% ($4.64 \times 10^8$ cfu/mL of ampicillin-resistant bacteria and $3.63 \times 10^8$ cfu/ml of ampicillin- and kanamycin-resistant bacteria during helper phage infection). $10^{10}$ or more independent clones, which were the target amount, were obtained.

These cells were stored as glycerol stock, and a 20-L scale phage preparation was prepared from the glycerol stock. As a result, 20 mL of library phage having a titer of 4.26×10$_{13}$ cfu/mL was obtained.

1-4-6. Genetic Sequence Confirmation of the Libraries

VHH clones constituting the libraries were randomly selected to determine their nucleotide sequences. The nucleotide sequences were determined according to the method mentioned in 2-6-2. The amino acid sequences encoded by the determined nucleotide sequences were analyzed. When the analyzed amino acid sequence was in frame and its framework region showed significant homology to that of a known VHH gene, the amino acid sequence was determined to be normal. Actually, no sequence with considerably low framework homology could be found. Thus, those with frame shifts or insertion of stop codon were determined to be abnormal. As a result, for IgG2, the genetic sequences of 87% of the clones were normal. Among those with normal sequences, 92.3% had hydrophilic amino acids as the 44th and 45th amino acids that interact with the L chain, i.e., encoded VHHs.

For IgG3, the sequences of 95.8% of the clones were normal. 96% of the normal clones had hydrophilic amino acids as the 44th and 45th amino acids that interact with L chains, i.e., encoded VHHs. Considering that the ratio of VHs and VHHs in germline genes is 1:1, VHHs were included in the libraries with very high selectivity.

Thus, libraries having excellent expression rate and high VHH ratio were constructed.

EXAMPLE 2

Analysis of VHH Genes

In Example 1, oligonucleotides comprising the nucleotide sequences of following SEQ ID NOs were used as primers. The origin of VHH amplified by each of the combinations of primers is summarized below.

| 5'-side (N-terminal) | 3'-side (C-terminal) | origin of amplified VHH |
|---|---|---|
| SEQ ID NOs: 1-6 | SEQ ID NO: 10 | IgG2 |
| SEQ ID NOs: 1-6 | SEQ ID NO: 11 | IgG3 |

Fifty or more clones were randomly selected from each library to analyze their nucleotide sequences. Examples of analyzed results are shown in Table 1. Each cell of the Table corresponds to a single class. In Table 1, subfamilies are classified based on the position of cysteine residues, and furthermore, within the subfamilies, classes are grouped based on the length of CDR2 and CDR1. The determination of CDR was performed according to a known method (Kabat et al., Sequence of Proteins of Immunological Interest, 5th edit., US Public Health Service, NIH Bethesda, Md., Publication (1991) No. 91-3242). Structural characteristics used as indices for classification were specified according to following criteria:

Length of CDR1:

The number of amino acids from the 31st amino acid from the N-terminus to one amino acid before the 36th W (tryptophan) that is defined by Kabat.

Length of CDR2:

The number of amino acids from the 50th amino acid as defined by Kabat to one amino acid before the 66th R (arginine).

Cys position number:

When Cys was located in the N-terminal side of the 36th W (tryptophan), the number indicating its position counted from the N-terminus was defined as the Cys position number. When Cys was located in the C-terminal side of the 36th W (tryptophan), the position of W36 was defined as 36, and the number count up to the Cys position was defined as the Cys position number.

TABLE 1

| Subfamily | Cysteine residue position | Length of CDR2 (aa) | Length of CDR1 (aa) | Number of germlines according to existing report* | Library from primer (SEQ ID NO: 10) (mainly IgG2-derived) | Library from primer (SEQ ID NO: 11) (mainly IgG3-derived) |
|---|---|---|---|---|---|---|
| 1 | — | 21 | 5 | | 1 | |
| | | 20 | 2 | | 1 | |
| | | 18 | 5 | | 1 | |
| | | 17 | 4 | | 1 | |
| | | | 5 | 1 | 4 | 7 |
| | | | 6 | | | 1 |
| | | | 7 | | 1 | |
| | | 16 | 2 | | 1 | |
| | | | 5 | | 1 | 2 |
| 2 | 33 | 21 | 5 | | 1 | |
| | | 20 | 5 | | 1 | 1 |
| | | 19 | 7 | | 1 | |
| | | 18 | 5 | | 3 | 3 |
| | | 17 | 2 | | 1 | 1 |
| | | | 4 | | 2 | 1 |
| | | | 5 | 5 | 23 | 19 |
| | | | 6 | | 3 | 2 |
| | | | 7 | | | 1 |
| | | | 8 | | | 1 |
| | | | 10 | | | 1 |
| | | 16 | 5 | 1 | 8 | |
| | | | 6 | | | |
| | | 15 | 5 | | 1 | 1 |
| | | 14 | 5 | | 1 | |
| 3 | 30 | 22 | 3 | | 1 | |
| | | 17 | 2 | | 3 | |
| | | | 5 | | | |

TABLE 1-continued

| Subfamily | Cysteine residue position | Length of CDR2 (aa) | Length of CDR1 (aa) | Number of germlines according to existing report* | Library from primer (SEQ ID NO: 10) (mainly IgG2-derived) | Library from primer (SEQ ID NO: 11) (mainly IgG3-derived) |
|---|---|---|---|---|---|---|
| | | | 6 | | | |
| | | 16 | 5 | 2 | 9 | 3 |
| | | | 6 | | | |
| 4 | 45 | 17 | 5 | | | |
| | | | 6 | | | |
| | | 16 | 2 | | 1 | |
| | | | 5 | 3 | 7 | 9 |
| | | | 6 | | 1 | |
| | | | 7 | | 1 | |
| | | | 8 | | | 1 |
| 5 | 32 | 17 | 4 | | 1 | |
| | | | 5 | 2 | 2 | |
| | | | 6 | | | |
| | | 16 | 5 | 19 | 5 | 1 |
| | | | 6 | | | 1 |
| 6 | 50 | 17 | 5 | | | 2 |
| | | | 6 | | | |
| | | | 7 | | 1 | |
| | | 16 | 5 | | | |
| | | | 6 | | | |
| 7 | 32,33 | 17 | 5 | | | 1 |
| | | | 6 | | | |
| | | 16 | 5 | | | |
| | | | 6 | | | |
| 8 | 30,32 | 17 | 4 | | 1 | |
| Total | | | | 33 | 89 | 59 |

*(EMBO J. 19 (5) 921, 2000)

According to the literature (Nguyen et al., EMBO J. 19(5), 921 (2000)), classification of VHH genes into 7 subfamilies had been attempted based on:

1) position of the cysteine residue, and 2) length of CDR2 sequence.

Specifically, the reference proposes to classify the genes based on the cysteine residue position (30, 32, 33, or 45) and the length of CDR2 sequence (16 or 17 amino acids) as shown in Table 2.

TABLE 2

| Length of CDR2 (aa) | Cysteine residue position | | | | |
|---|---|---|---|---|---|
| | none | 33 | 30 | 45 | 32 |
| 17 | 1a | 2a | | | 5a |
| 16 | | 2b | 3b | 4b | 5b |

The blanks in the Table mean that the authors of the above-mentioned reference could not find clones corresponding to them. In contrast, as shown in Table 1, diversity greater than that of the subfamily classifications shown in Table 2 was found as a result of analysis by the present inventors. For example, many of the clones had CDR2 lengths other than 16 or 17 amino acids, and some showed a cysteine residue position of 50 or a combination of the above-mentioned cysteine residue positions.

Furthermore, in the above-mentioned literature, CDR1 of 5 amino acids in length are the only ones reported. However, as apparent from Table 1 showing the analysis results by the present inventors, great variety was also found in the length of CDR1. Different from CDR3, CDR1 and CDR2 are located at positions that are not changed during rearrangement of antibody genes. Therefore, basically, the lengths of CDR1 and CDR2 are considered not to change in-germlines as well as in mRNA.

Considering the above, as shown in Table 1, the present inventors classified VHH into 8 subfamilies base on 1) cysteine positions. Furthermore, a new class division was aimed with additional indices of: 2) length of CDR2 sequence, and 3) length of CDR1 sequence. The division into each class as in Table 1 shows that there is far greater diversity of germlines than that reported in the literature. Therefore, VHH genes amplified by the primers newly designed by the present inventors can be regarded as more faithfully reproducing the in vivo diversity of camels.

The subfamilies of VHHs newly discovered by the present inventors are useful as indices of VHH gene diversity of libraries. Specifically, a library can be determined to maintain the in vivo diversity, when 33 clones arbitrary selected from clones constituting the library, and analyzed for their VHH structure are classified into at least 8 or more classes based on the classification method of the present inventors. A preferred library of the present invention that maintains the in vivo diversity comprises clones of 6 or more VHH subfamilies as well as 15 or more classes when sufficient amount of clones are randomly sampled from clones constituting the library and then investigated.

EXAMPLE 3

Production of VHHs Against GST Using VHH-Type Antibody Libraries 3-1. Determination of Screening Conditions Based on the screening method of WO 01/62907, VHHs having binding affinity for glutathione S-transferase (GST) were selected.

GST was prepared to a final concentration of 0.1 mg/mL using PBS, 3.8 mL of this solution was placed into each of 1 (first time) or 2 (second and third time) test tubes (Nunc, MaxiSorp™), and incubated at 4° C. for 18 hr to adsorb GST on the inner wall of the test tubes. After adsorption, the solution was discarded, 3.8 mL of PBS containing 2% skim milk was added to each tube, and reacted at 25° C. for 1 hr for blocking.

IgG2 and IgG3 libraries were screened independently without mixing. The amount of phage used is shown under the column of "Input phage (cfu)" in Table 3. 3.8 ml of phage solution suspended in PBS containing 2% skim milk was added to each test tube, and after reacting at room temperature for 2 hr, the test tubes were washed 8 times with PBS-0.05% Tween 20.

Next, 3.5 mL of 0.1 M triethylamine (pH 12.3) was added to each test tube, and reacted in a rotator at room temperature for 20 min for dissociation. Then, neutralization by adding 0.875 mL of 1 M Tris-HCl buffer (pH 6.8) to each test tube allowed collection of phages bound to the antigen-bound MaxiSorp™ tubes.

3-2. Amplification of Collected Phages

The collected solution was treated as follows: infection of the phage into *E. coli*, infection of helper phage, and collection of the phage, to purify and amplify the contained phage.

1) Infection of Phage into *E. coli*

*E. coli* (DH12S) was cultured in 50 mL of 2×YT medium, and when the absorbance at a wavelength of 600 nm reached 0.5, the phage dissociated in 3-1 was added thereto. This was cultured with shaking at 37° C. for 1 hr.

2) Infection of Helper Phage

To 54 mL of the above-mentioned culture of 1), 433 mL of 2×YT medium, 12.5 mL of 40% glucose, and 0.5 mL of 100 mg/mL ampicillin were added. After culturing at 37° C. to reach an absorbance of 0.5 at the wavelength of 600 nm, the bacteria were precipitated and collected by centrifugation at 5,000 rpm for 10 min at 4° C., and then suspended in 150 mL of 2×YT medium added with 0.15 mL of 100 mg/mL ampicillin. To this suspension, 1/100 amount (1.5 mL) of helperphage M13K07 was added and cultured with shaking at 37° C. for 1 hr.

The culture was added to 450 mL of medium (2×YT medium containing 100 μg/mL of amipicillin and 70 μg/mL of kanamycin) pre-warmed to 37° C. and cultured at 37° C. overnight.

3) Collection of Phage

The culture mentioned above in 2) was centrifuged at 8,000 rpm for 10 min at 4° C., and 1/5 volume of 20% polyethylene glycol containing 2.5 M sodium chloride was added to the supernatant. This solution was left standing at room temperature for 20 min, centrifuged at 8,000 rpm for 15 min at 4° C., and then the precipitate was collected. Sterilized PBS was added at 1/10 volume of the culture to dissolve the precipitate. 20% polyethylene glycol containing 2.5 M sodium chloride was added again at 1/5 volume of the culture, and this was centrifuged at 10,000 rpm for 20 min at 4° C. The supernatant was discarded, and the residue was further spun down and then centrifuged at 10,000 rpm for 2 min at 4° C. PBS containing 0.05% $NaN_3$ was added at 1/100 volume of the culture to dissolve the precipitate, and thus, VHH phage was collected.

3-3. Rescreening using Amplified Phage

Using the amplified phage, similar screening was repeated using antigen-bound test tubes. Since washing during screening is an important step in dissociating non-specifically adsorbed phages to select phages with high binding ability, the washing conditions were set at 30 times for the second screening, and 35 times for the third screening.

3-4. Method for Evaluating Phage Screening

When the value (total number of phages placed into an antigen-adsorbed test tube)÷(total number of phages collected from the antigen-adsorbed test tube) becomes obviously smaller compared to that for the previous screening during repeated screening by the method mentioned above, a phage displaying the VHH of interest can be supposed to being more concentrated. The number of phage contained in the solution was calculated as follows:

1) Dilution series of phage were produced as follows:

[1] $1\times10^{-2}$ dilution: 10 μL of phage solution ÷990 μL of PBS

[2] $1\times10^{-4}$ dilution: 10 μL of the dilution [1]+990 μL of PBS

[3] $1\times10^{-6}$ dilution: 10 μL of the dilution [2]+990 μL of PBS

[4] $1\times10^{-8}$ dilution: 10 μL of the dilution [3]+990 μL of PBS

[5] $1\times10^{-9}$ dilution: 100 μL of the dilution [4]+900 μL of PBS

[6] $1\times10^{-10}$ dilution: 100 μL of the dilution [5] +900 μL of PBS

990 μL of DH12S was added to 10 μL of [4], [5], and [6] of the dilution series and incubated for infection at 37° C. for 1 hr. 100 μL of these solutions were spread onto LBGA plates, cultured at 30° C. for 18 to 24 hr, and the numbers of colonies were counted. Among the above-mentioned dilution series, usually the plate treated with [4] produced 50 or more plaques. The number of phages per mL was calculated as shown below based on the number of plaques on the plate treated with [4]. Number of phages in the stock solution= (number of colonies/plate)×$(1\times10^8)\times10^3$ cfu/mL.

3-5. Results of GST Screening

The number of collected phage was calculated similarly, and the number of phage displaying VHH against the antigen was determined for per screening. The results are shown in Table 3. Since the ratio of collected phage (input/output) increased in the third screening, specific VHH was expected to be concentrated at this stage.

TABLE 3

|  | Wash | Input phage (cfu) | Output phage (cfu) | Input/output |
|---|---|---|---|---|
| IgG2 library |  |  |  |  |
| 1st | 8 | $1.00 \times 10^{14}$ | $1.30 \times 10^9$ | $7.69 \times 10^4$ |
| 2nd | 30 | $3.60 \times 10^{14}$ | $2.20 \times 10^6$ | $1.64 \times 10^8$ |
| 3rd | 35 | $2.00 \times 10^{13}$ | $4.70 \times 10^7$ | $4.26 \times 10^5$ |
| IgG3 library |  |  |  |  |
| 1st | 8 | $1.00 \times 10^{14}$ | $1.40 \times 10^9$ | $7.14 \times 10^4$ |
| 2nd | 30 | $3.90 \times 10^{14}$ | $2.60 \times 10^6$ | $1.50 \times 10^8$ |
| 3rd | 35 | $2.00 \times 10^{13}$ | $1.20 \times 10^7$ | $1.67 \times 10^6$ |

3-6 Measuring Antigen Binding Activity of VHH Obtained by Screening 3-6-1. Confirming Activity of Obtained Phage VHH by ELISA The antigen binding activity (affinity) of VHH selected by the above-mentioned screening was measured by ELISA using 96-well microtiter plate. As the samples, not phage-type VHH but VHH-cp3-type VHH was used.

First, to express VHH-cp3, phage-infected *E. coli* was cultured in 2×YT containing 1% glucose and 100 μg/mL ampicillin at 30° C. for 18 hr, then 5 μL of the above-mentioned culture was added to 1.5 mL of 2×YT containing 0.1% glucose and 100 μg/mL ampicillin, and was cultured at 30° C. for 4 hr. At this time, the concentration of *E. coli* was measured as the absorbance at a wavelength of 600 nm and was approximately 0.5.

To this culture, isopropyl-1-thio-β-D-galactoside (IPTG) was added to a concentration of 1 mM and cultured at 30° C. for 18 hr. 1.5 mL of the culture was sampled into an Eppendorph tube, and centrifuged at 10,000 rpm for 5 min at 4° C. The supernatant was collected and sodium azide was added at 0.1% to prepare a sample.

Next, GST-bound ELISA plates were prepared. Specifically, GST was diluted to a final concentration of 100 μg/mL. 100 μL of the diluted GST solution was added to each well of a 96-well microtiter plate (Nunc, MaxiSorp™), and after binding at 4° C. for 18 hr, 200 μL of 5% BSA (blocking solution) was added to each well and blocking was performed at 37° C. for 1 hr. After discarding the blocking solution, the plate was washed once with PBS and used for affinity measurements.

Figure 7:
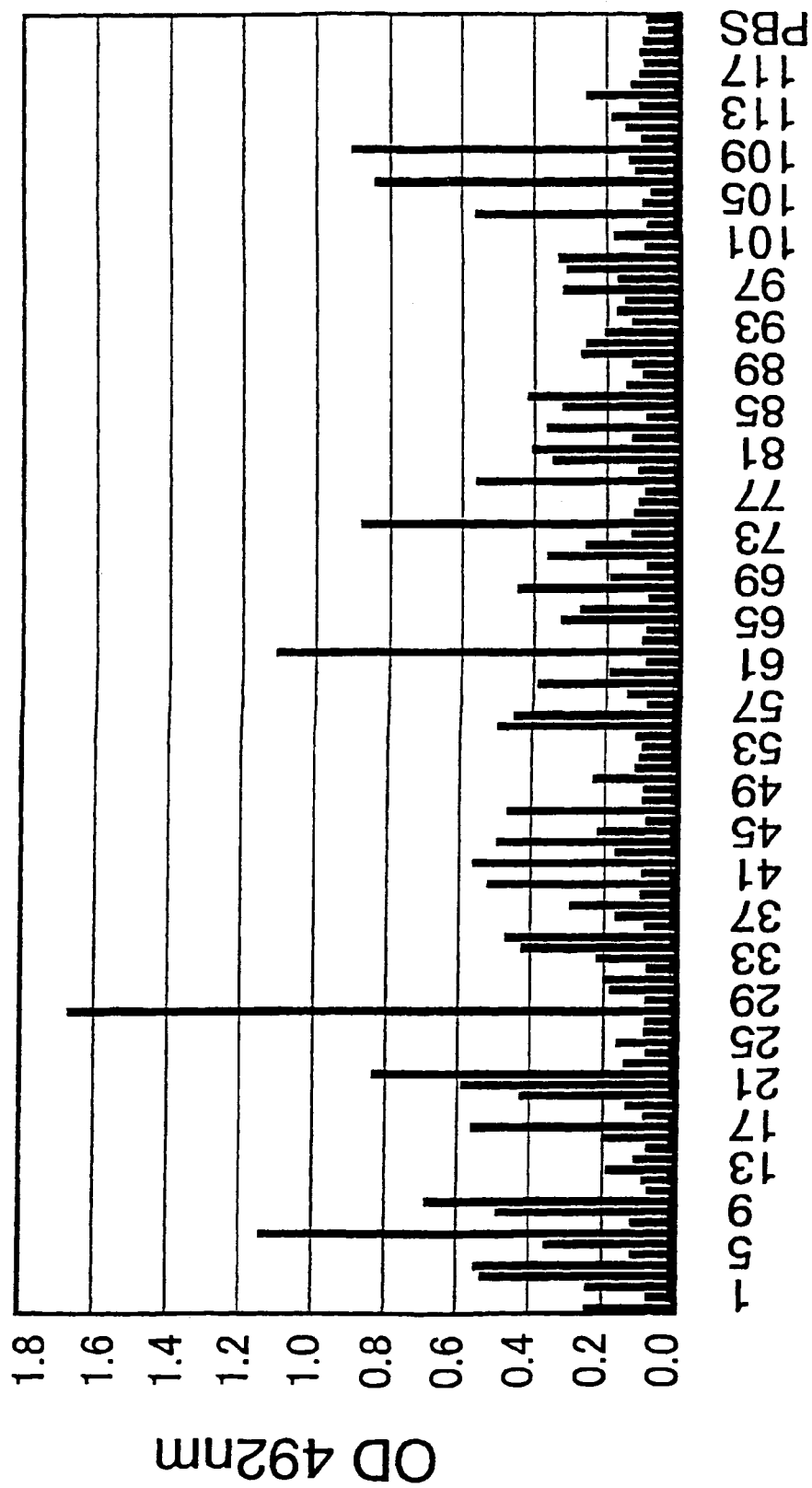
FIG. 7 shows the results of ELISA confirming the responsiveness of VHH (IgG2) clones to GST. The vertical axis shows the absorbance (OD 492 nm), and the horizontal axis shows the sample number.
Figure 8:
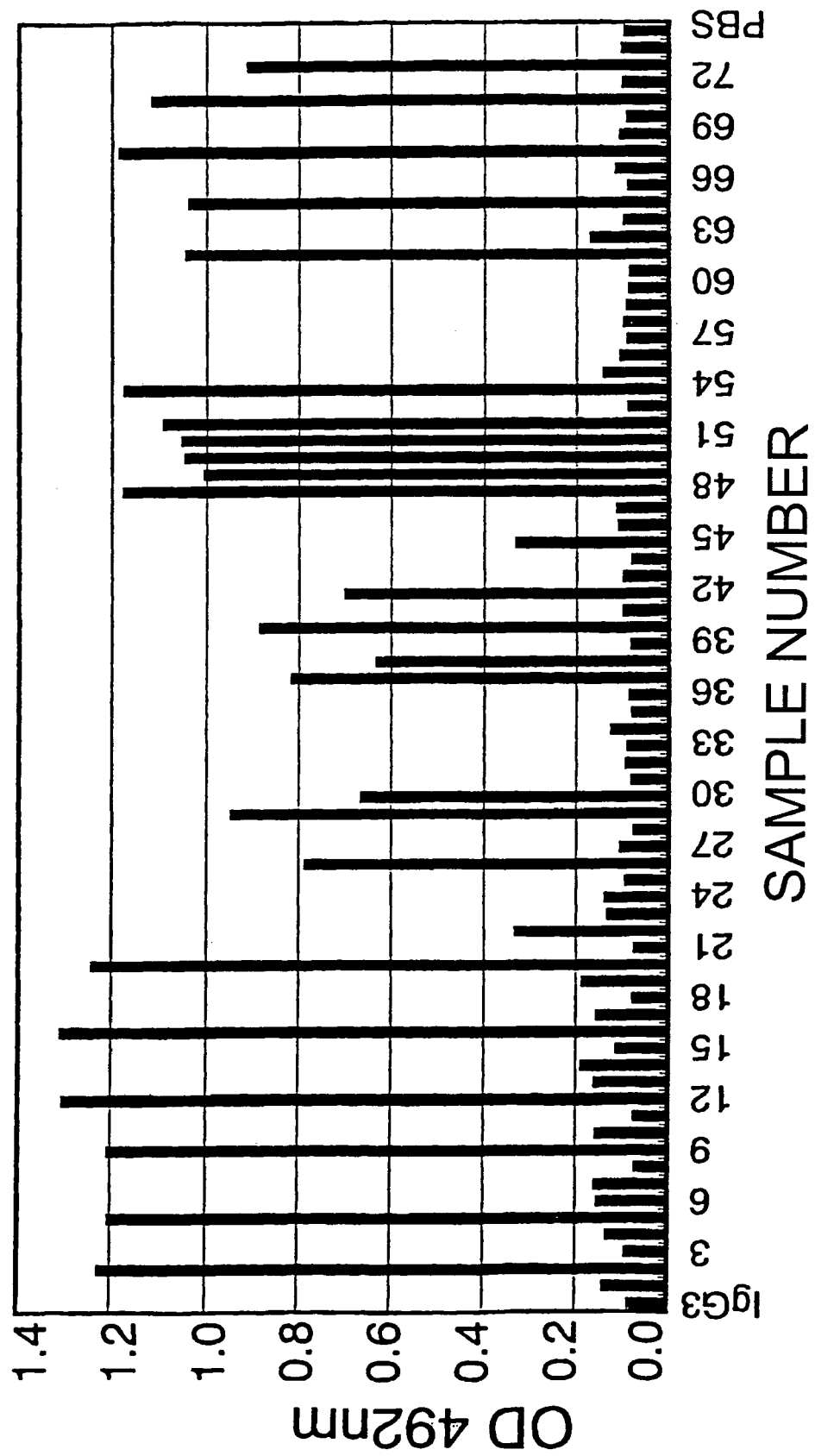
FIG. 8 shows the results of ELISA confirming the responsiveness of VHH (IgG3) clones to GST. The vertical axis shows the absorbance (OD 492 nm), and the horizontal axis shows the sample number.

100 μL of the sample was added to each well and reacted at 25° C. for 1 hr. After the reaction, the plate was washed 4 times with PBS, 100 μL of 250-fold diluted peroxidase-labeled anti-cp3 antibody (MBL) was added and reacted at 25° C. for 1 hr. Again, the plate was washed 4 times with PBS, 100 μL of a solution of orthophenylenediamine and hydrogen peroxide was added and reacted for a while, then 100 μL of 2 N sulfuric acid was added to stop the reaction, and the absorbance at a wavelength of 492 nm was measured. As a result, binding activity was confirmed in 71 clones out of 192 clones. 46 clones of IgG2 (FIG. 7) and 25 clones of IgG3 (FIG. 8) having binding activity were selected.

3-6-2. Sequence Analysis of Obtained Anti-GST VHHs

Seventy-one clones showing antigen binding activity were selected, cultured in LBGA at 30° C. for 18 hr, and phagemids were then purified using KURABO DNA Isolation System PI-50. These phagemids were used to confirm the nucleotide sequences of their genes. Using fluorescence primer T7 (ALOKA), the nucleotide sequences were determined by the dideoxy method using Thermosequence kit (Amersham Pharmacia), and ALOKA L1-COR4200L(S)-2.

Based on their CDR3 sequences, one type of IgG3 and six types of IgG2 were confirmed. The CDR3 amino acid sequences of the clones obtained by the screening are summarized in Table 4. One type of CDR3 in IgG3 is also found in IgG2, and suggests the existence of a mechanism of subclass switching.

TABLE 4

| Origin | Amino acid sequence | SEQ ID NO: | Number of clones |
|---|---|---|---|
| IgG2 CDR3 | VFKSWCSDGLGTTLPNY | 19 (98-114) | 13 |
| IgG2 CDR3 | DFKPWCSDGLGTTLPNY | 49 | 26 |
| IgG2 CDR3 | VSGRAYCSGMSIYGDSD | 15 (99-115) | 2 |
| IgG2 CDR3 | TDESPLRRRFSLLDRRRYD | 16 (98-116) | 1 |

TABLE 4-continued

| Origin | Amino acid sequence | SEQ ID NO: | Number of clones |
|---|---|---|---|
| IgG2 CDR3 | DGGYYSCGVGEE | 50 | 1 |
| IgG2 CDR3 | KSYMCGSTLWRRIDQYND | 51 | 1 |
| IgG2 CDR3 | DISAPPGIGGTCAFLGDY | 52 | 1 |
| IgG3 CDR3 | VFKSWCSDGLGTTLPNY | 19 (68-114) | 25 |

3-7. Purification of Anti-GST VHH (Conversion to Protein A-fused Type, Expression-confirming ELISA, Large-scale Purification)

Three types of anti-GST VHH were converted to protein A-fused proteins from cp3-fused proteins. Following 3 clones were used as anti-GST VHHs.

No. 21: a clone where 2 clones were isolated

No. 29: a clone with the highest ELISA value

NO. 75: a clone comprising the most common CDR3 (38 clones)

The amino acid sequence and nucleotide sequence of each clone are shown in following SEQ ID NOs.

| Clone No. | Nucleotide sequence | Amino acid sequence |
|---|---|---|
| No. 21 | SEQ ID NO: 14 | SEQ ID NO: 15 |
| No. 29 | SEQ ID NO: 16 | SEQ ID NO: 17 |
| No. 75 | SEQ ID NO: 18 | SEQ ID NO: 19 |

The procedures were as shown below. First, the cp3 region was removed by self ligation using SalI to obtain a transformant. Specifically, each of the No. 21, No. 29, and No. 75 clone DNA was SalI-cleaved by following method.

1 μg of DNA (each of the cp3 expression-type VHH expression vectors)/33 μL sterilized MILLIQ water 4 μL of 10× High Buffer (Takara, supplied with SalI)

3 μL SalI (Takara)

A reaction solution of the above-mentioned composition was incubated at 37° C. for 2 hr. This was electrophoresed on 0.8% agarose gel at 100 mA for approximately 1 hr, and the band found near 4 kB was cut out using a razor blade. DNA was extracted with QIAEXII (QIAGEN) and subjected to ethanol precipitation. Thus obtained DNA was self ligated under following conditions.

Collected DNA dissolved in 62 μL of sterilized MILLIQ water

| | |
|---|---|
| 10 mM DTT | 10 μL |
| 10 mM ATP | 10 μL |
| 10× Ligase buffer | 10 μL |
| T4 DNA Ligase (Takara) 350 U/μL | 8 μL |

After incubating the reaction solution at 16° C. for 15 hr, DNA was collected by ethanol precipitation. This DNA was dissolved in 3 μL of 10-fold sterilized MILLIQ water-diluted TE (10 mM Tris, 1 mM EDTA pH 8.0). 1.5 μL thereof was used to transform 20 μL of DH12S by electroporation. The conditions for the transformation were as described above in 1-4-5 under the item of "Transformation of heavy chain variable region antibody libraries (IgG2 and IgG3 libraries) for VHH-type selection". The obtained bacterial strain was cultured in 500 mL of 2×TY containing 0.1% glucose and 100 μg/mL ampicillin, and expression was induced with 1 mM IPTG in the early stage of logarithmic growth (OD 660 nm=0.5). Twenty hours after the expression induction, bacteria were collected to obtain the supernatant as the culture supernatant comprising protein A-type VHH.

Next, the protein A-type VHH was purified as follows. First, 36 g of ammonium sulfate was added to per 100 mL of the obtained culture supernatant (60% ammonium sulfate) to precipitate protein by stirring at 4° C. for 1 hr. This was then centrifuged at 8,000 rpm for 10 min and the supernatant was discarded.

One tablet of protease inhibitor (Complete™, Roche) dissolved in 30 mL of PBS was added per 500 mL of the culture supernatant, and the precipitate was removed by centrifugation at 10,000 rpm for 15 min. 0.05% $NaN_3$ and 1.5 mL of IgG Sepharose™ 6 Fast Flow (Amersham Biosciences) resin were added to 30 mL of the supernatant and stirred for 1 hr. The resin solution was charged into a column (10 mL poly-prep, Bio-Rad) by gravity and flushed twice, each time with 10 mL of 0.1% Tween-PBS. Next, 10 mL of PBS each time was flowed twice. Furthermore, 50 mL of PBS was flowed similarly. After finally passing 5 mL of 10-fold diluted PBS through, protein A-type VHH was eluted under following conditions.

Three mL of 50 mM citric acid (pH 2.4) was passed through and the eluate was collected.

Next, 4 mL of 0.1 M glycine (pH 3.0) was passed through and the eluate was collected.

Finally, 5 mL of 50 mM citric acid (pH 2.4) was passed through and the eluate was collected.

The collected eluate was neutralized with 350 μL of 3 M Tris, and the neutrality of the solution was confirmed with pH paper. Each of the eluate was dialyzed overnight at 4° C. against 3 L of PBS using a 3500 MWCO dialysis membrane (PIERCE). After the dialysis, $NaN_3$ was added to 0.05%. The concentration of the obtained purified protein was determined by measuring the absorbance at 280 nm. The value obtained by dividing the OD 280 nm by 1.4 gave the protein concentration as μg/mL. Furthermore, the molecular weight (MW) of the collected protein was confirmed by SDS-PAGE. The results are as shown below.

|  | Protein concentration | Molecular weight |
|---|---|---|
| No. 21 | 445 μg/15 mL | MW. 30 KD |
| No. 29 | 494 μg/15 mL | MW. 30 KD |
| No. 75 | 649 μg/15 mL | MW. 28 KD |

The theoretical molecular weight of a protein A-type VHH is 28 KD. Therefore, the results of SDS-PAGE support the finding that these proteins have the structure of interest.

Next, using the supernatant of the transformant, the binding activity of the protein A-type VHH for GST was confirmed. First, 16 transformant clones were each induced to express the protein in small quantity, and their culture supernatant containing protein A-type VHH was dispensed into GST-coated microwells (MaxiSorp™) as a primary antibody. Then, rabbit anti-mouse Fab antibody (4000-fold dilution) having affinity for Protein A was used as the secondary antibody, and 4000-fold diluted goat anti-rabbit IgG-HRP (MBL) as the tertiary antibody to confirm the expression of protein A-type VHH and its binding ability.

As a result, in all of the culture supernatants of the transformants, protein A-type VHH having binding activity towards GST was detected.

3-8. Binding Constant Measurement on Purified Anti-GST VHHs

The interaction with GST of VHHs selected from the library of this invention was analyzed. Specifically, ka (binding rate constant), kd (dissociation rate constant), and KD (dissociation constant; kd/ka) of the interaction with GST of clones No. 75 and No. 29 were determined by affinity measurement and kinetic analysis. BIAcore11000 biosensor device was used for the analysis.

Carboxymethyldextran (Sensor Chip CM5, Research grade, BIAcore) sensor chip was used. Antigen (GST) was immobilized on the chip by electrostatic attachment to the CM5 matrix and by covalent bonding between the lysyl group of CM5 and activated carboxyl group of the antigen. The carboxyl group was activated by EDC/NHS coupling reaction (Johnson K et al. Methods., A companion to methods in enzymology 6, 199-205 (1994)).

At a flow rate of 5 μL/min using HBS-EP (BIAcore), lysyl groups on CM5 were activated (2.4 min of contact time) with EDC/NHS (equal amounts of EDC and NHS of Amine Coupling Kit (BIAcore) were mixed), and then the chip was washed with HBS-EP (BIAcore). Next, 20 μg/mL of GST (Sigma, 0.6 mg protein/mL diluted in 10 mM acetic acid (pH 4.0)) was added to the chip. After HBS-EP wash of the chip, 1 Methanol amine (pH 8.5) was added, and the remaining activated carboxyl group was inactivated. After the inactivation, the chip was washed with 50 mM NaOH, and all GST that did not form covalent bounds were removed. The amount of immobilized antigen was calculated to be 2252 RU. The binding was evaluated as near 300 RU by adding saturating amount of clone No. 75 to the sensor.

All analysis experiments were performed at an HBS-EP flow rate of 35 μL/min of HBS-EP (BIAcore) at 25° C., and regeneration in 50 mM NaOH for 1 min.

The binding was traced by altering the concentration of clone No. 75 ($5\times10^{-8}$ M to $4.0\times10^{-7}$ M). Using (Langmuir) binding (BIAevaluation Ver. 3), the curve showed a satisfactory fit. Base line correction was also considered. When ka (1/Ms) was determined by Global fitting (BIAevaluation Ver. 3), a value of $3.81\times10^4$ $M^{-1}S^{-1}$ was obtained. When kd (1/S) was determined, the value was $9.15\times10^{-4}S^{-1}$. Due to the occurrence of mass transport limitation, this value is used as the lower limit. The KD value calculated based on kinetic analysis was 24 nM.

When the binding of clone No. 29 was evaluated, the amount of immobilized antigen was 1750 RU, and saturating amount of clone No. 29 was added to the sensor to give a value of near 460 RU. Similar conditions were used for other parameters of the evaluation. The ka (1/Ms) was $2.54\times10^4 M^1 S^1$, kd (1/S) was $2.55\times10^{-3}S^{-1}$, and the KD value calculated based on kinetic analysis was 100 nM. The kd of clone No. 75 was low, and therefore had a high binding constant. Accordingly, clone No. 75 was considered to be a VHH that does not readily dissociate.

EXAMPLE 4

4. Enzyme Activity Inhibition Experiment using Purified Anti-GST VHH 4-1. Parameter Setting for Enzyme Activity Measurement GST is a bisubstrate enzyme that uses both glutathione and CDNB as substrates. The influence of VHH selected from the VHH libraries of the present invention on the enzyme activity was evaluated based on the conditions reported in the literature (Habig WH et al., J. Biol. Chem.

Nov. 25, 249(22), 7130 (1974)): 1 mM CDNB, 1 mM glutathione, and 1.5 µM GST. Since the curve was linear up to 3 min from the start of the enzyme reaction and decreased somewhat thereafter, the slope was calculated from the value per min up to 3 min to determine the enzyme reaction rate.

Using this method of measurement, the binding constant by Edie plot was determined wherein CDNB was fixed at 1 mM and glutathione concentration was varied in the range of 2-0.0625 mM. The binding constant was the same as previously reported (Measured value of Km =0.48 mM). Furthermore, the appropriate glutathione concentration was determined so that it falls within a measurable range (approximately up to 1.5 with respect to a blank sample of water) on a spectrophotometer when CDNB is varied and the enzyme concentration is kept constant.

4-2. Confirming Enzyme Inhibition by VHH

To measure under enzyme reaction measurement condition of 1 mM CDNB, 1 mM glutathione, and 1.42 µM enzyme, VHH was concentrated with Centricon® YM-10 (Millipore). As a result, coexistence of 3.8 to 5 µM VHH (clone: No. 21, No. 29, or No. 75) became possible. Thus, the enzyme reaction rate was measured similarly to 4-1.

| | |
|---|---|
| MILLIQ water | 220 µL |
| 1 M potassium phosphate (pH 6.5) | 25 µL |
| 100 mM CDNB | 2.5 µL |
| 100 mM glutathione | 2.5 µL |

A mixed solution of 1.0 µg GST/25 µL PBS and each of the VHHs (0 to 5 µM) was incubated at room temperature for 1 hr, and the above-mentioned composition was added thereto. After addition, the absorbance at 340 nm was measured at 25° C.

Figure 9:
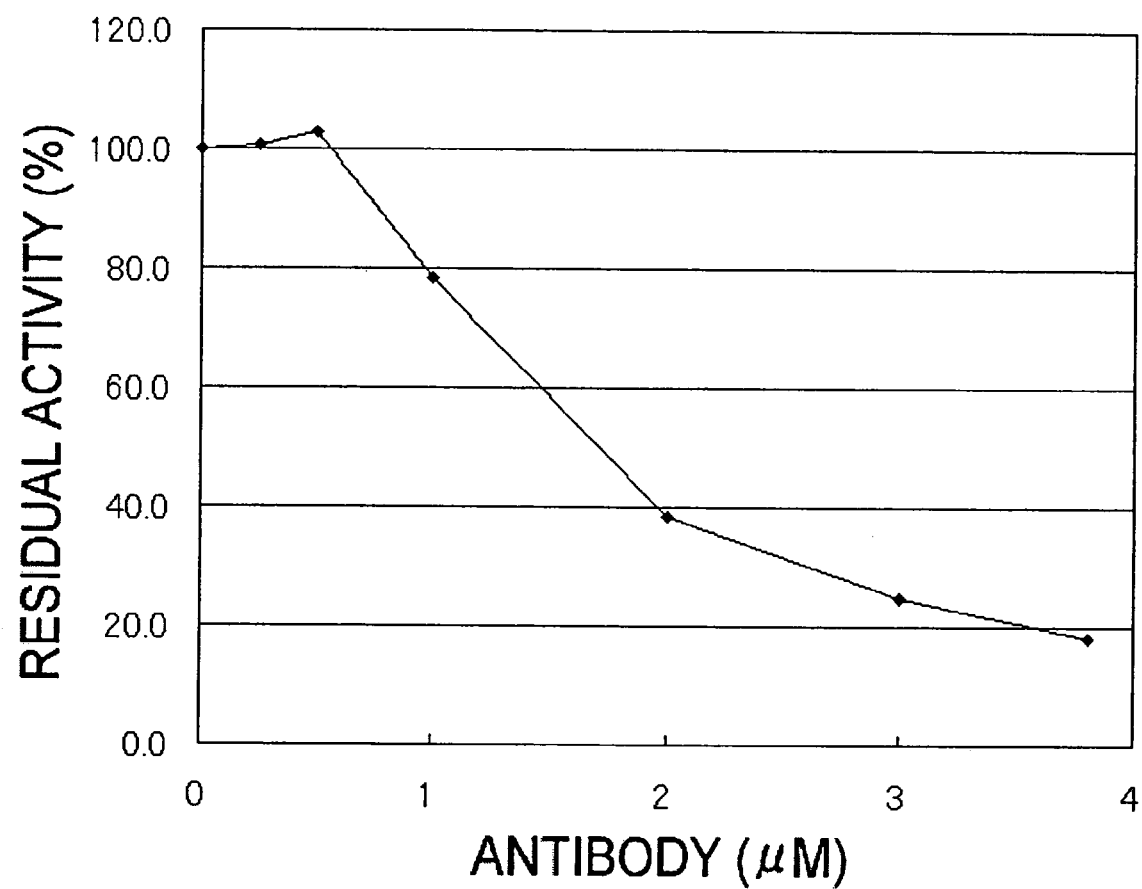
FIG. 9 shows the result of measuring the inhibitory effect of anti-GST VHHs on GST activity. The vertical axis shows the residual activity (%) of GST, taking the enzyme activity in the absence of VHH action as 100, and the horizontal axis shows the concentration (µM) of added VHH.

As a result, no enzyme inhibitory activity of No. 21 and No. 29 could be observed even at the highest VHH concentration. For No. 75, VHH concentration-dependent enzyme inhibitory activity seemed to exist. This inhibition was significant at 1.5 µM or more. The measurement result of No. 75 is shown in FIG. 9.

Furthermore, to confirm whether the apparent Km is changing, CDNB was kept constant at 1 mM, and the glutathione concentration was varied between 2 to 0.0625 mM. The reaction was performed under following conditions:

| | |
|---|---|
| MILLIQ water | 220 µL |
| 1 M potassium phosphate (pH 6.5) | 25 µL |
| 100 mM CDNB | 2.5 µL |
| 200 mM to 6.25 mM glutathione | 2.5 µL |

A mixed solution of 1.0 µg GST/25 µL PBS and each of the VHHs (2 µM) was incubated at room temperature for 1 hr, and the above-mentioned composition was added thereto. After addition, the absorbance at 340 nm was measured at 25° C.

Figure 10:
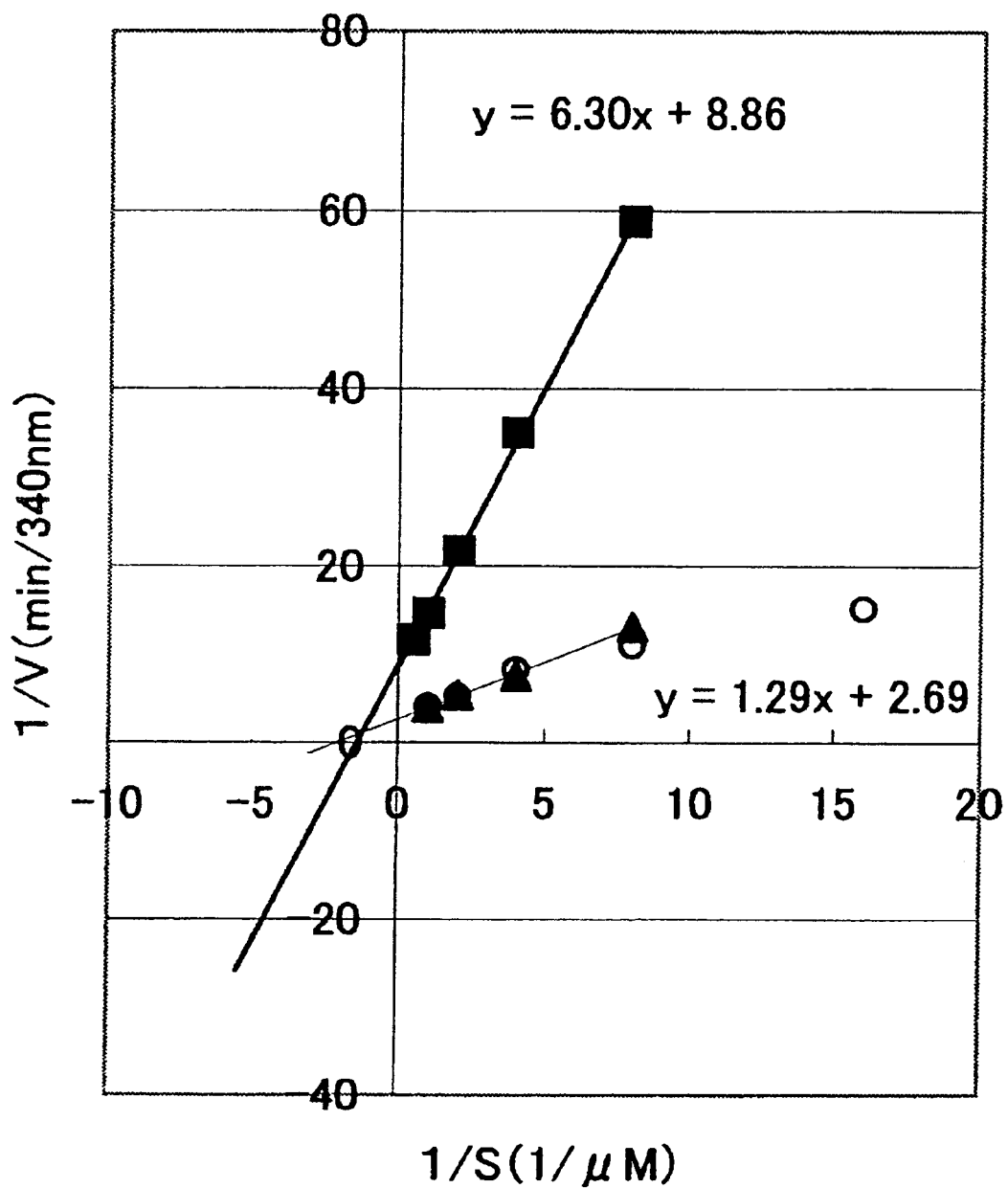
FIG. 10 shows the result of examining the competitive effect of anti-GST VHHs on glutathione. The vertical axis shows the reciprocal of the amount of change in absorbance per minute, and the horizontal axis shows the reciprocal of CDNB concentration.

FIG. 10 summarizes a part of the results. In the interest of No. 29, even the result at the highest VHH concentration was nearly the same as that in the absence of VHH. On the other hand, for No. 75, the slope significantly differs with a VHH concentration of 2 µM, where the apparent Vmax was small and the apparent Km was unchanged. This result shows that the VHH of No. 75 inhibits GST noncompetitive with glutathione.

Next, the Lineweaver-Burk plot obtained with 0.25 mM glutathione and changing CDNG from 4 to 0.25 mM was confirmed to become linear. The measurement was carried out under following conditions:

| | |
|---|---|
| 1 M potassium phosphate (pH 6.5) | 25 µL |
| 100 mM CDNB | 10 to 1.25 µL |
| 25 mM glutathione | 2.5 µL |
| adjusted to 250 µL with MILLIQ water. | |

A mixed solution of 1.0 µg GST/25 µL PBS, and each of the VHHs (2 µM) was incubated at room temperature for 1 hr, and the above-mentioned composition was added thereto. After addition, the absorbance at 340 nm was measured at 25° C.

Figure 11:
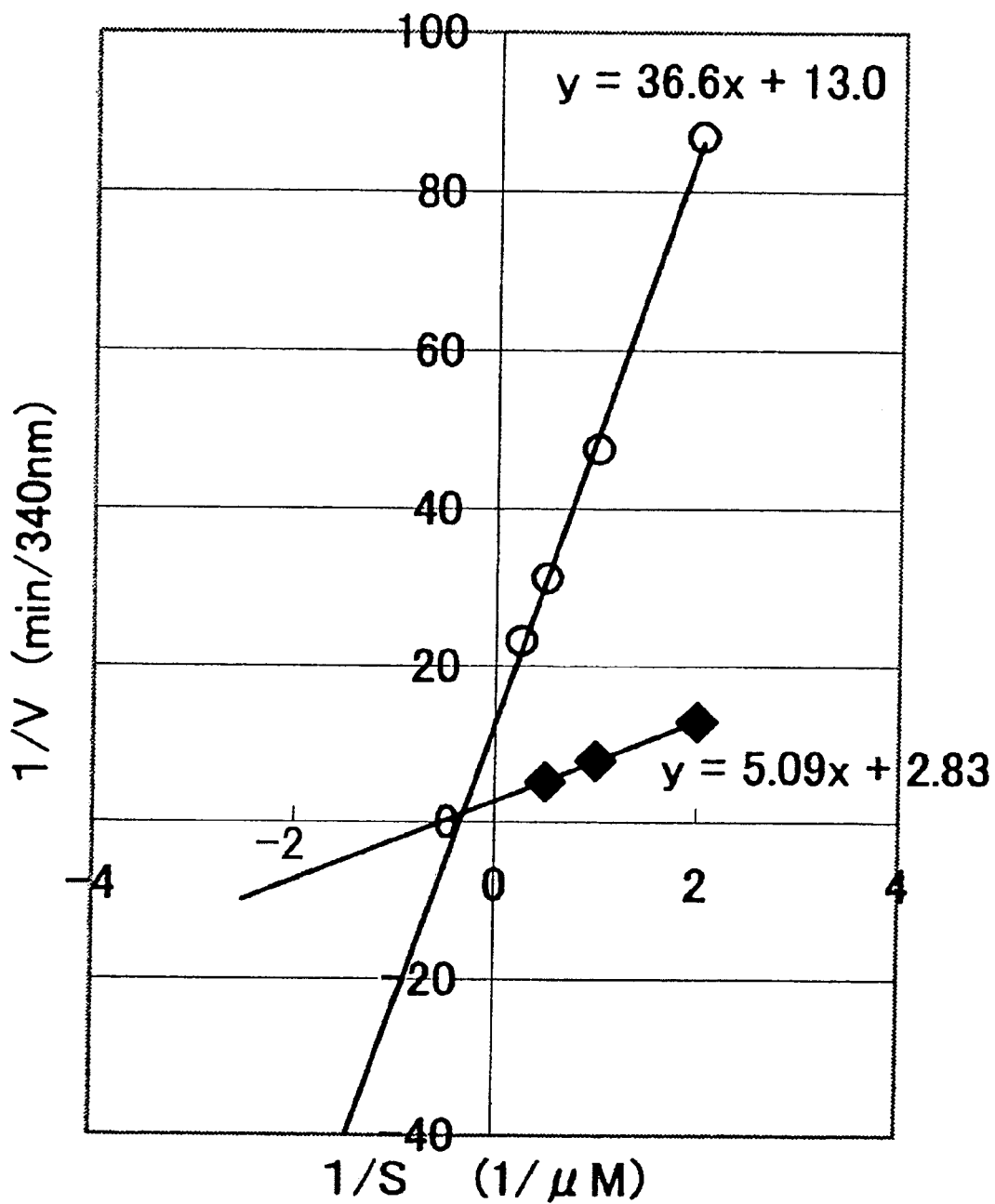
FIG. 11 shows the result of examining the competitive effect of anti-GST VHHs on CDNB. The vertical axis shows the reciprocal of the amount of change in absorbance per minute, and the horizontal axis shows the reciprocal of glutathione concentration.

A part of the results is summarized in FIG. 11. When No. 75 VHH was used in this system, the slope changed significantly and the apparent Vmax became small, but the apparent Km did not change. This indicates that the VHH inhibited GST noncompetitive with CDNB.

Accordingly, No. 75 VHH acts noncompetitive on both of the substrates. Therefore, theVHHseems to recognize, asepitope, asite of GST that is different from the binding sites of these substrates. Thus, no products may be generated from the enzyme substrate complex (ESC), an intermediate, due to its changes in the conformation by the binding of the VHH.

EXAMPLE 5

Lactic Acid Dehydrogenase VHH Screening using VHH-type Antibody Library 5-1. LDH Screening VHH having binding affinity for lactic acid dehydrogenase was screened. *Bacillus stearothemophillus*-derived lactic acid dehydrogenase (L-LACTIC DEHYDROGENASE; LDH, SIGMA, 250 units) expressed in *E. coli* was used as an antigen for the screening.

The active unit of commercially available LDH was described as 123 units/mg solid and 586 units/mg protein. The purity of this commercially available product was confirmed by SDS-PAGE. As a result, the purity was considered to be approximately 80%. (Dimers of two 35-KD monomers and tetramers of 4 of the monomers are formed.)

The procedure for screening was as follows. LDH concentration was adjusted with PBS to 0.2 mg/mL, and dispensed at 25 µL/well into MaxiSorp™ loose (Nunc-Immuno™ Module). Four wells were used for the first screening, and 1 well each for the 2nd to 4th screenings. LDH was adsorbed on the inner walls of the wells by incubation at 4° C. for 18 hr. After adsorption, the solution was discarded, 150 µL/well of PBS containing 1% BSA was added, and reacted at 37° C. for 1 hr for blocking.

Fifty µL of the library was added at the amount of input phage (cfu) (PBS containing 1% BSA was used as the buffer) shown in Table 5, and after reacting for 2 hr at 37° C., the wells were washed with PBS by the number of times shown in Table 5. Then, phages bound to the antigen were collected as follows. Specifically, 50 µL/well of 0.1 M HCl-glycine (pH 2.2) was added, and reacted at room temperature for 10 min for dissociation. Three µL/well of 2 M Tris was added thereto for neutralization, and the solution was collected.

5-2. Amplification of Collected Phase

The collected solution was treated as follows: infection of the phage into *E. coli*, infection of helper phage, and collection of the phages to purify and amplify the comprised phage.

1) Infection of phage into *E. coli*

*E. coli* (DH12S) was cultured in 2 mL of 2×YT media to proliferate to an absorbance of 0.5 at a wavelength of 600 nm. Then, the solution of phage dissociated in 5-2 was added thereto and cultured with shaking at 37° C. for 1 hr.

2) Infection of helper phage

To the culture of 1), 6 mL of Super Broth medium (30 g of Triptone (DIFCO), 20 g of yeast extract (DIFCO), and 10 g of MOPS (Nakalai Tesque) were filled up to 1 L using distilled water, pH was adjusted to 7.0, and was steam-sterilized at 121° C. for 20 minutes) and 100 mg/mL of ampicillin to a final volume of 1/1000 were added, and cultured with shaking at 160 rpm for 2 hr at 37° C. Subsequently, $10_{12}$ CFU (1.0 mL) of helper phage M13K07, 92 mL of Super Broth medium, and 100 mg/mL of ampicillin to a final volume of 1/1000 were added thereto, and cultured with shaking at 160 rpm for 2 hr at 37° C. Kanamycin was then added to a concentration of 70 μg/mL, and cultured overnight at 37° C.

Collection of phages, re-screening of amplified phages, and method of evaluating phage screening followed the method described for anti-GST VHH, except that PBS was used for washing and washing was performed 15 times for the 2nd and 3rd screening and 20 times for the 4th screening.

5-3. Result of LDH Screening

The course of screening is shown in Table 5. As apparent from Table 5, the collection rate (output/input) increased in the 4th screening and VHH against LDH was considered to be isolated.

TABLE 5

| screening cycle number | input phage (cfu) | number of times of washing | output phage (cfu) | output/input |
|---|---|---|---|---|
| 1 | $4 \times 10^{12}$ | 7 | $1.2 \times 10^7$ | $1/(3.3 \times 10^5)$ |
| 2 | $1.1 \times 10^{12}$ | 15 | $2.1 \times 10^6$ | $1/(5.2 \times 10^5)$ |
| 3 | $2.3 \times 10^{12}$ | 15 | $1.6 \times 10^6$ | $1/(1.4 \times 10^6)$ |
| 4 | $2.3 \times 10^{11}$ | 20 | $4.5 \times 10^6$ | $1/(5.1 \times 10^4)$ |

Similarly to anti-GST VHH, 60 clones and 36 clones were prepared as monoclones from the 3rd and 4th screenings, respectively. Next, ELISA was performed similarly as for anti-GST VHH.

LDH dissolved in PBS at 200 μg/mL was used to sensitize MaxiSorp™. Culture supernatant, 10-fold diluted mouse anti-cp3 monoclonal 3G3A8H1, and 1000-fold diluted goat anti-mouse IgG (H+L)-POD were added as primary, secondary, and tertiary antibodies, respectively, to this antigen-sensitized plate. As negative control, PBS was added instead of performing antigen sensitization.

Figure 12:
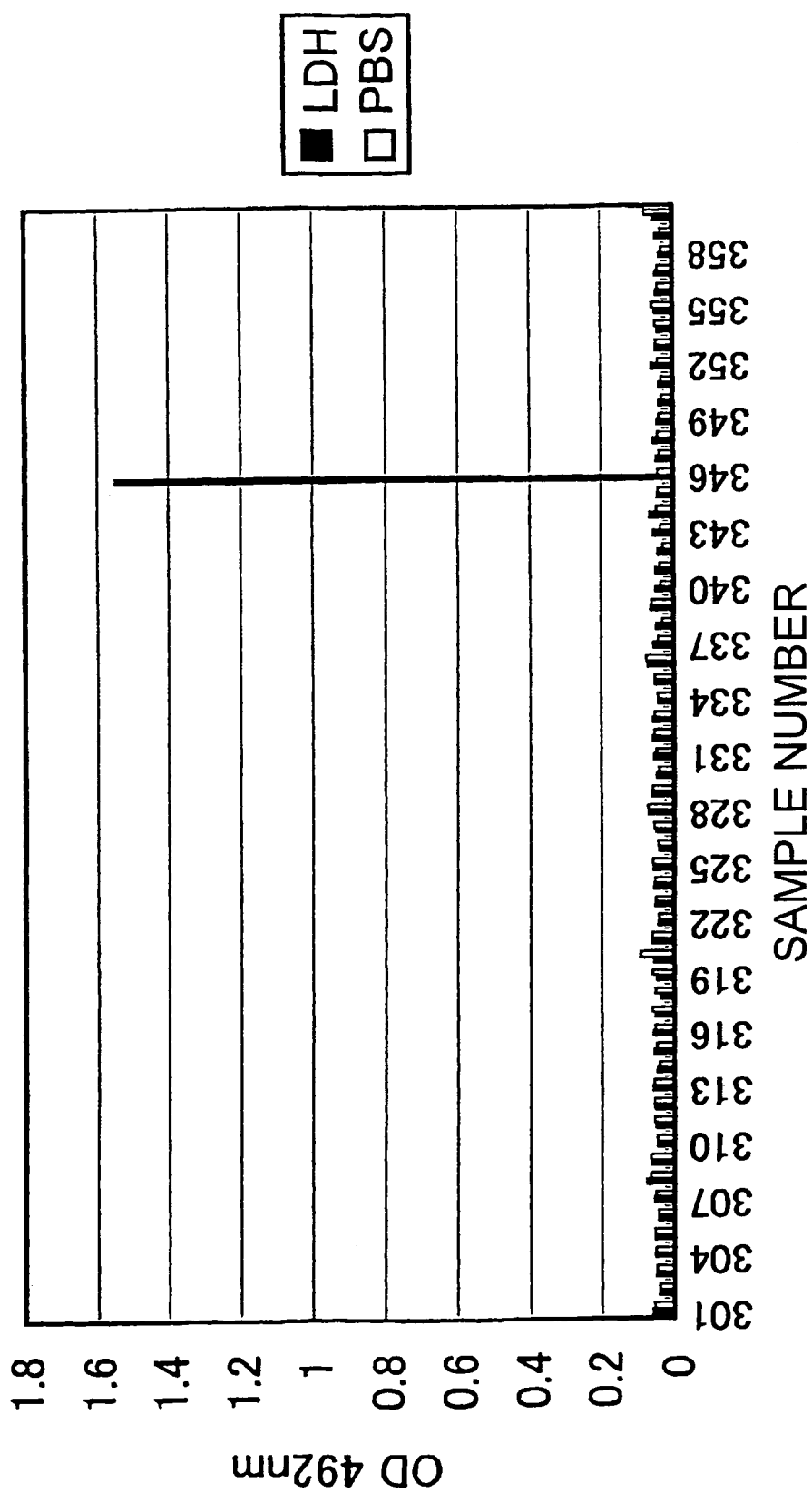
FIG. 12 shows the result of ELISA confirming the responsiveness of VHH clones to LDH in the third screening cycle. The vertical axis shows the measured value at OD 492 nm in ELISA, and the horizontal axis shows the sample number.
Figure 13:
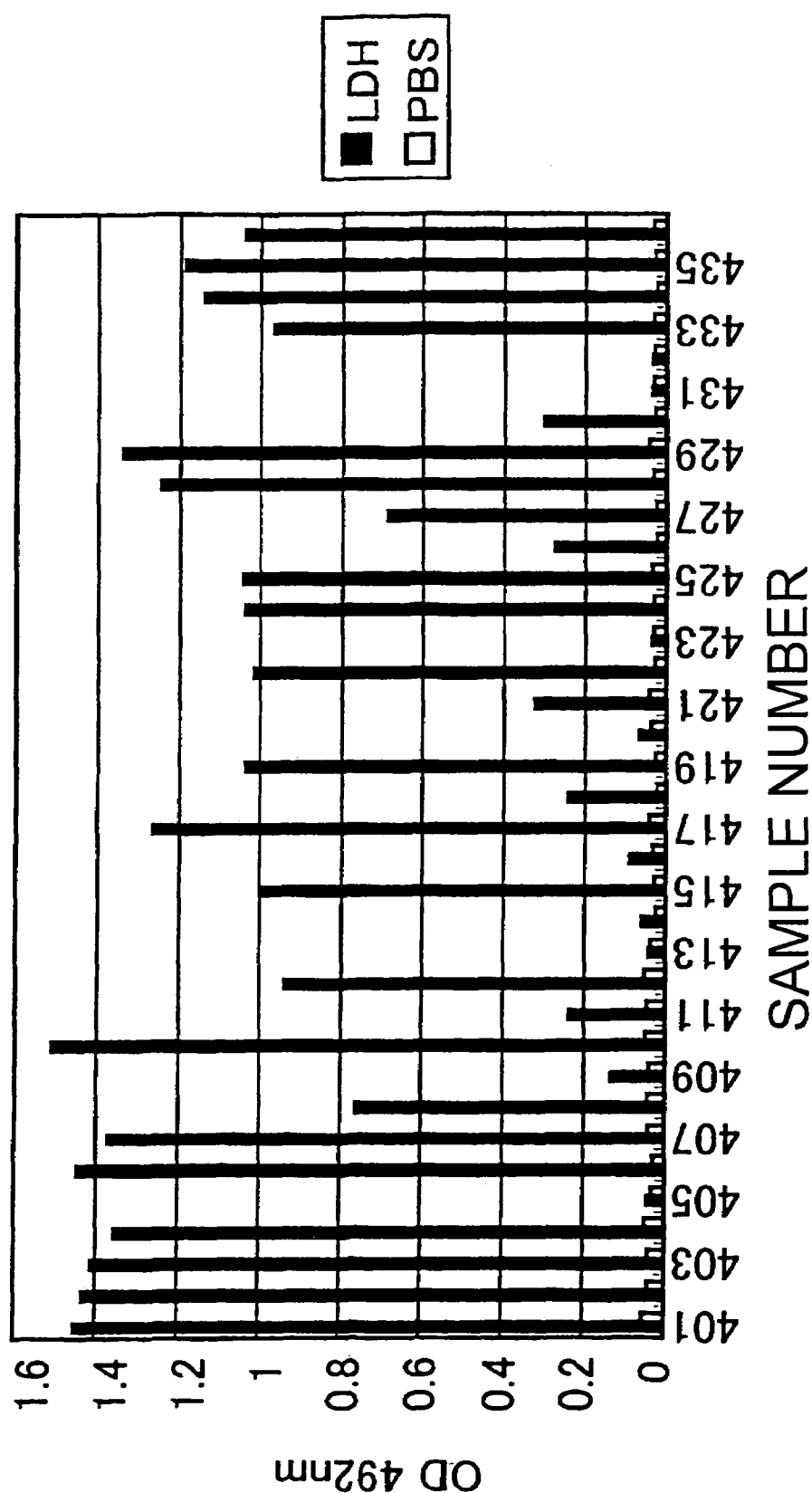
FIG. 13 shows the result of ELISA confirming the responsiveness of VHH clones to LDH in the fourth screening cycle. The vertical axis shows the measured value at OD 492 nm in ELISA, and the horizontal axis shows the sample number.

The results of ELISA are shown in FIG. 12 (the 3rd screening) and FIG. 13 (the 4th screening). In the 4th screening, 29 clones were ELISA positive.

Next, the nucleotide sequences of the genes were analyzed by a similar method to anti-GST VHH. As a result, 11 types of VHHs, judged from their CDR3 sequences, were isolated (2 kinds of VH types existed)

5-4. Conversion of Anti-LDH VHH to Protein A-fused Type

According to the method described in Example 3 (GST), 8 of the clones were converted to protein A types by SalI digestion and self-ligation.

Transformants transfected with each of the VHH clones were cultured at 800 mL scale, and purified with IgG Sepharose to yield 200 to 800 μg of purified VHH for every clone. The nucleotide sequences of the 8 clones used in the experiment and the amino acids encoded by those nucleotide sequences are shown in the following SEQ ID NOs.

| Clone No. | Nucleotide Sequence | Amino acid sequence |
|---|---|---|
| No. 407 | SEQ ID NO: 20 | SEQ ID NO: 21 |
| No. 415 | SEQ ID NO: 22 | SEQ ID NO: 23 |
| No. 418 | SEQ ID NO: 24 | SEQ ID NO: 25 |
| No. 421 | SEQ ID NO: 26 | SEQ ID NO: 27 |
| No. 426 | SEQ ID NO: 28 | SEQ ID NO: 29 |
| No. 428 | SEQ ID NO: 30 | SEQ ID NO: 31 |
| No. 430 | SEQ ID NO: 32 | SEQ ID NO: 33 |
| No. 434 | SEQ ID NO: 34 | SEQ ID NO: 35 |

5-5. Inhibitory Activity of Lactic Acid Dehydrogenase VHH

The activity to inhibit the reaction to produce lactic acid from pyruvic acid was detected for clones No. 407, 415, 421, 426, 428, 430, 434, and control. Anti-GST VHH (clone No. 29) obtained in the above Example was used as the control.

First, VHH concentration was estimated by SDS-PAGE. Then, 8 μM of VHH was incubated for 1 hr with LDH (1.4 μM), and the residual enzyme activity was measured. The conditions for activity detection were as follows:

66 mM sodium phosphate buffer (pH 7.0)
1 mM pyruvic acid
120 μM NADH
280 nM LDH, 1.6 μM VHH (final), 26° C. (room temperature)

The reaction catalyzed by LDH is as follows:

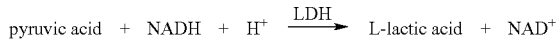

$$\text{pyruvic acid} + \text{NADH} + \text{H}^+ \xrightarrow{\text{LDH}} \text{L-lactic acid} + \text{NAD}^+$$

Figure 14:
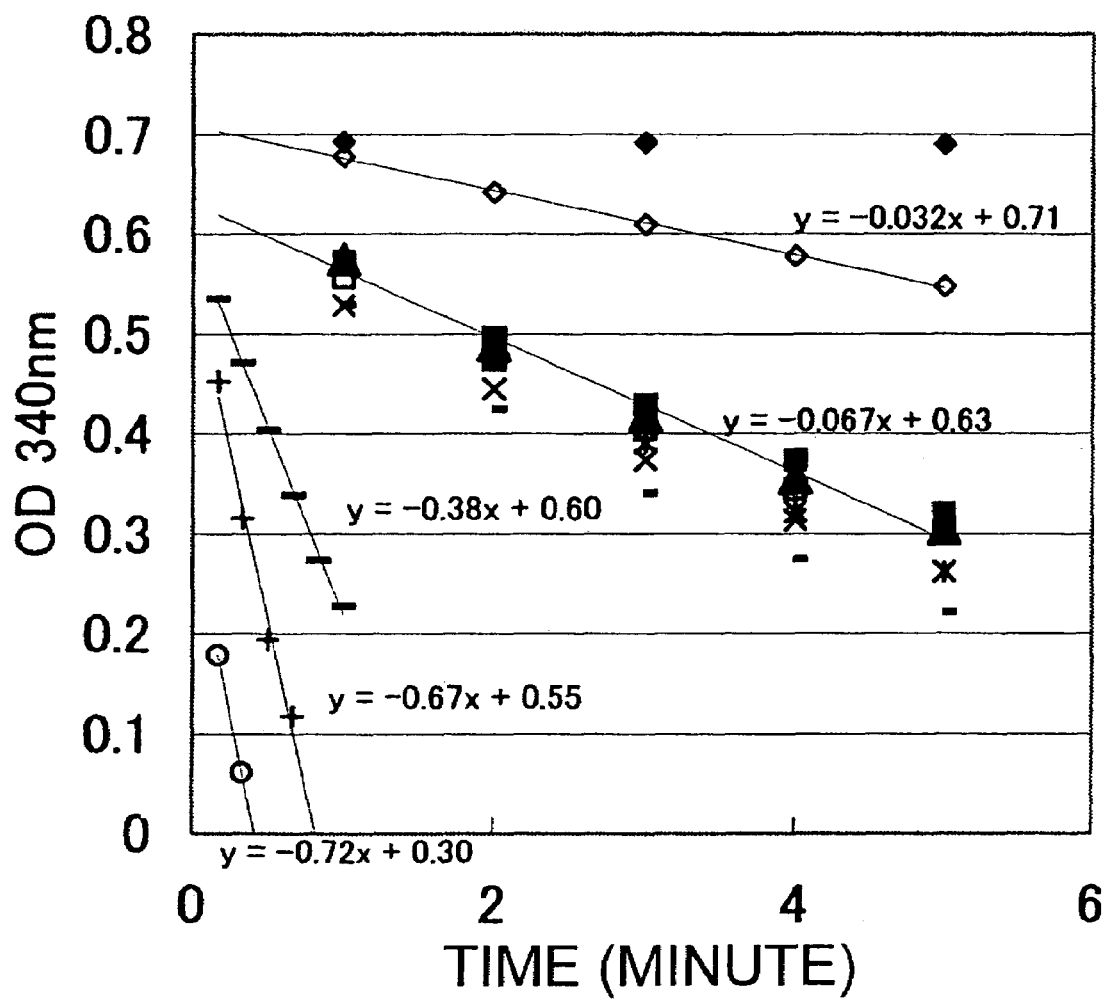
FIG. 14 shows the results of measuring the effect of anti-LDH VHHs on LDH activity. The vertical axis shows the measured value at OD 492 nm in ELISA, and the horizontal axis shows the elapsed time (minutes) from the start of the enzyme reaction.

The enzyme activity was detected by measuring the absorbance at 340 nm. The measurement results are shown in FIG. 14. As a result, the enzyme reaction was rather enhanced by clones No. 418, No. 421, and No. 428. No. 430 showed inhibitory activity. No. 407, No. 415, No. 426, and No. 434 showed same reaction rate with anti-GST VHH (clone No. 29) addition that was used as a control, and were considered not to affect the LDH enzyme activity.

Next, considering the possibility of contamination by substrates and presence of low-molecular-weight reaction-promoting substances, the VHH solution was filtered through an ultrafiltration membrane with 3000 MW cut-off (Microcon YM-3) and the results were confirmed with this filtrate alone. As a result, neither promoting effect nor inhibitory effect could be confirmed in the filtrate. Therefore, the action of regulating enzyme activity confirmed in FIG. 14 was considered to be due to the activity-regulating effect by a high-molecular-weight protein, i.e., VHH. Under the reaction conditions used herein, VHHs that increase the reaction rate in the direction of lactic acid production by 10 fold (No. 418 and No. 421), and by 5 fold (No. 428), and a VHH that inhibits the reaction rate in the direction of lactic acid production (No. 430) were obtained.

Preliminary experiments with modified pyruvic acid concentration to raise sensitivity were performed to detect enzyme activity using decreased amounts of enzyme and VHH. These experiments revealed that the enzyme activity can be measured using the enzyme at 22.4 nM. Accordingly, VHH concentration dependence was investigated for clone No. 430. (56 nM of enzyme and the VHH were incubated)

Conditions for measuring the enzyme activity were as below:

66 mM sodium phosphate buffer (pH 7.0)

10 mM pyruvic acid

120 µM NADH 22.4 nM LDH (final), 26° C.

Figure 15:
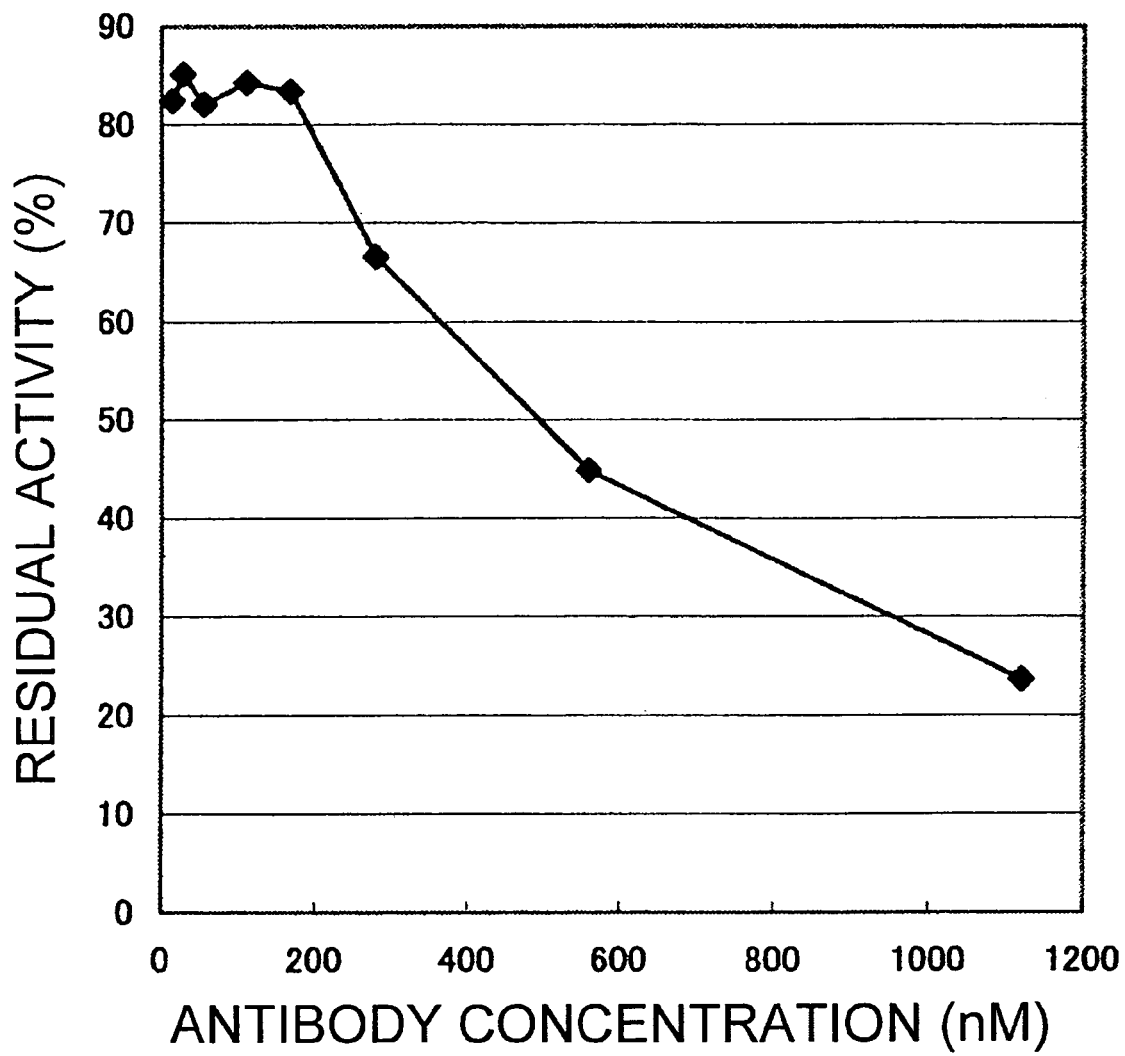
FIG. 15 shows the result of measuring the VHH concentration dependence of the LDH activity inhibitory action by anti-LDH VHHs. The vertical axis shows the residual activity (%) of LDH taking the enzyme activity in the absence of VHH action as 100, and the horizontal axis shows the concentration of added VHH (µM).

The measurement results are shown in FIG. 15. The inhibitory effect of VHH could be observed starting from 5 fold (278 nM) of VHH, and with 20 fold VHH, the residual activity decreased to 20%.

5-6. Binding Constant Measurement of Lactic Acid Dehydrogenase VHH using BIAcore Procedure similar to that with GST was used to immobilize LDH on CM-sensor chip (Sensor Chip CM5, Research grade, BIAcore) using the amino coupling method.

Lysyl groups on CM5 were activated using EDC/NHS (equal amounts of EDC and NHS of Amine Coupling Kit (BIAcore) were mixed) (8-minute contact time), and the chip was washed with HBS-EP (BIAcore). Twenty µg/mL of LDH (Sigma, 0.2 µg protein/mL diluted in 10 mM acetic acid (pH5.0)) was then added to the chip. After washing the chip with HBS-EP, 1 M ethanol amine (pH 8.5) was added to inactivate the remaining activated carboxyl groups. Following the inactivation, the chip was washed with HBS-EP to remove all LDHs that had not been covalently bound. The amount of immobilized antigens was calculated 5653 RU. When binding was evaluated by adding saturating amounts of clone No. 430 to the sensor, the value was near 800 RU. The value was near 500 RU for clone No. 428, and near 1400 RU for clone No. 421.

All experiments were performed in HBS-EP at 25° C., and regeneration was performed under optimum conditions. Washing was performed for 1 min using 50 mM citric acid (pH2.5).

The binding was monitored by changing the LDH concentration ($5 \times 10^{-8}$ M to $4.0 \times 10^{-7}$ M). The curve showed a satisfactory fit when (Langmuir) binding or 1:1 binding with mass transfer (BIAevaluation Ver.3) was used. Base-line correction was also taken into consideration. Values of ka (1/Ms), kd (1/S), and KD calculated based on kinetic analysis using global fitting (BIAevaluation Ver. 3) were as shown in Table 6.

In enzyme inhibition experiments, IC50 of No. 430 was approximately 400 nM, close to the measured value of approximately 250 nM for KD. This result was suggested to prove the occurrence of inhibition due to the binding.

TABLE 6

| Clone No. | ka ($M^{-1}S^{-1}$) | kd ($S^{-1}$) | KD × $10^{-7}$ (M) | KA × $10^6$ (1/M) |
|---|---|---|---|---|
| (Langmuir) binding model | | | | |
| 421 | $2.39 \times 10^4$ | $4.09 \times 10^{-3}$ | 1.72 | 5.83 |
| 428 | $1.44 \times 10^4$ | $5.13 \times 10^{-3}$ | 3.56 | 2.81 |
| 430 | $9.82 \times 10^3$ | $2.58 \times 10^{-3}$ | 2.63 | 3.80 |
| 1:1 binding with mass transfer model | | | | |
| 421 | $2.39 \times 10^4$ | $4.09 \times 10^{-3}$ | 1.71 | 5.83 |
| 428 | $1.48 \times 10^4$ | $5.16 \times 10^{-3}$ | 3.50 | 2.86 |
| 430 | $1.15 \times 10^4$ | $2.85 \times 10^{-3}$ | 2.48 | 4.04 |

EXAMPLE 6

6. Construction of IgM Heavy Chain Variable Region Library 6-1. Cloning of IgM Constant Region, Cµ (constant µ)

Similar to Example 1, cDNA was prepared from mRNA of 22 camels using random primers.

The following primer was constructed based on the sequence of the C-terminal portion of IgM constant region, Cµ (constant µ), which is conserved among humans and mice. PCR was performed using the N-terminal primer of the heavy chain variable region and camel cDNA to clone camel Cµ.

AACGTA<u>GGCGCGCC</u>GGACTTGTCCACGGTCCTCTC/ SEQ ID NO: 38

The underlined indicates the AscI cleavage site.

PCR fragments were cleaved with SfiI and AscI restriction enzymes, cloned into pFCA-10 vector cleaved with SfiI and AscI, and then used for transformation by the aforementioned method. DNA was prepared as described above from the transformants, and the nucleotide sequence of the N-terminal region of Cµ was determined. The nucleotide sequence and amino acid sequence of the N terminus of camel Cµ are shown below.

```
E   S   S   S   A   P   T   L   Y   P   L  /  SEQ ID NO: 40
GAG AGC TCA TCT GCC CCG ACA CTC TTC CCC CTC/  SEQ ID NO: 39
```

6-2. Construction of IgM Heavy Chain Variable Region

An oligonucleotide comprising the following nucleotide sequence was designed as a primer that can selectively yield the IgM heavy chain variable region from the newly cloned camel Cµ sequence.

SEQ ID NO: 41
ACATTAATCTGGCGCGCCGAGAGTGTCGGGGCAGATGAGCTCTC/

By a method similar to that previously described in the section of IgG VHH library construction, cDNA was obtained using random primers with 20 μg of the obtained mRNA from 22 camels as a template.

Using 1/40 amount of the obtained cDNA as a template, each of the 6 types of primers (SEQ ID NOs: 1 to 6) of the N-terminal region of the V domain was combined with the above-mentioned primer, and PCR was performed using 6 types of primer sets.

PCR conditions were 95° C. for 3 min, followed by 19 cycles of 94° C. for 1 min, 72° C. for 2 min, and 72° C. for 1 min. All PCR products obtained from each combination of primers were combined, electrophoresed on 0.8% agarose gel, and a band at approximately 0.5 kbp was cut out using a razor blade. QIAEX II (QIAGEN) was used for DNA extraction. The amount of collected DNA estimated using DAPI was 178 μg.

6-3. Cloning of IgM Heavy Chain Variable Region Into Vector

According to the method described in Example 1, the mixed collected PCR fragments were cleaved with SfiI restriction enzyme, ligated to SfiI-cleaved pFCA-10 vector, and DNA fragments were collected by performing phenol treatment and ethanol precipitation. The fragments were further cleaved with AscI restriction enzyme, collected by phenol treatment and ethanol precipitation, and ligation was performed. The amount of the collected DNA measured by DAPI staining was 66 μg.

6-4. Transformation

According to the method described in Example 1, the DNA obtained above was used to transform 7.5 mL of DHS12S. (The process of transforming 20 μL of ElectroMAX™ DH12S with 0.17 μg of the DNA by electroporation was repeated.) The overall number of transformed bacteria estimated by sampling a part of this material was $6.6 \times 10^{10}$.

6-5. Construction of IgM Heavy Chain Variable Region Library Phage

Overnight culture of a part of the transformed *E. coli* resulted in $2.5 \times 10^{11}$ DH12S/87.5 mL. Two liter of sterilized 2×TY media, glucose at a final concentration of 1%, and ampicillin at a final concentration of 100 μg/mL were added thereto, and cultured at 37° C. until OD 600 nm reached 0.8. The culture was centrifuged at 8,000 rpm for 10 min at 4° C., and bacterial cells in the precipitate were dissolved in 2 L of sterilized 2×TY media containing ampicillin at a final concentration of 100 μg/mL. Twenty milliliter of helper phage KO7 was then added thereto and cultured at 37° C. for 1 hr.

Four liter of sterilized 2×TY media, ampicillin at a final concentration of 100 μg/mL, and kanamycin at a final concentration of 50 μg/mL were added thereto and cultured overnight. According to the method described in Example 1, phages were collected from the overnight culture, yielding 50 mL of $2.4 \times 10_{14}$ cfu/mL phage library.

EXAMPLE 7

7. Screening of Antibodies Against β-gal using IgM Heavy Chain Variable Region Library 7-1. Conditions for Screening Antibodies Against β-gal The method for screening was performed similarly to that of GST according to WO 01/62907 and Example 3. However, β-gal concentration was adjusted to 0.1 mg/mL using PBS, 3.8 mL of the β-gal solution was added to each of the 2 test tubes (Nunc, MaxiSorp™) (1st screening) or 1 test tube (2nd and 3rd screenings), and incubated at 4° C. for 18 hr to adsorb β-gal on the inner walls of the tubes. After adsorption, the solution was discarded, 3.8 mL of PBS containing 2% skim milk was added to each tube, and reacted at 25° C. for 1 hr for blocking.

The IgM heavy chain variable region library was screened using the amount of input phage (cfu) shown in following Table, and adding 3.8 mL of PBS containing 2% skim milk to each test tube. (Table 7)

7-2. Results of Screening for Antibodies Against β-gal

The collection rate (output/input) increased in the 3rd screening, and antibodies against β-gal were considered to be concentrated.

TABLE 7

| Screening cycle number | Input phage (cfu) | Number of times of washing | Output phage (cfu) | Output/Input |
|---|---|---|---|---|
| 1 | $1.0 \times 10^{13}$ | 8 | $4.0 \times 10^9$ | $1/(3.0 \times 10^4)$ |
| 2 | $3.5 \times 10^{12}$ | 31 | $4.7 \times 10^5$ | $1/(7.4 \times 10^6)$ |
| 3 | $1.4 \times 10^{12}$ | 31 | $7.8 \times 10^9$ | $1/(180)$ |

7-3. Anti-β-gal Antibody Monoclone ELISA

Figure 18:
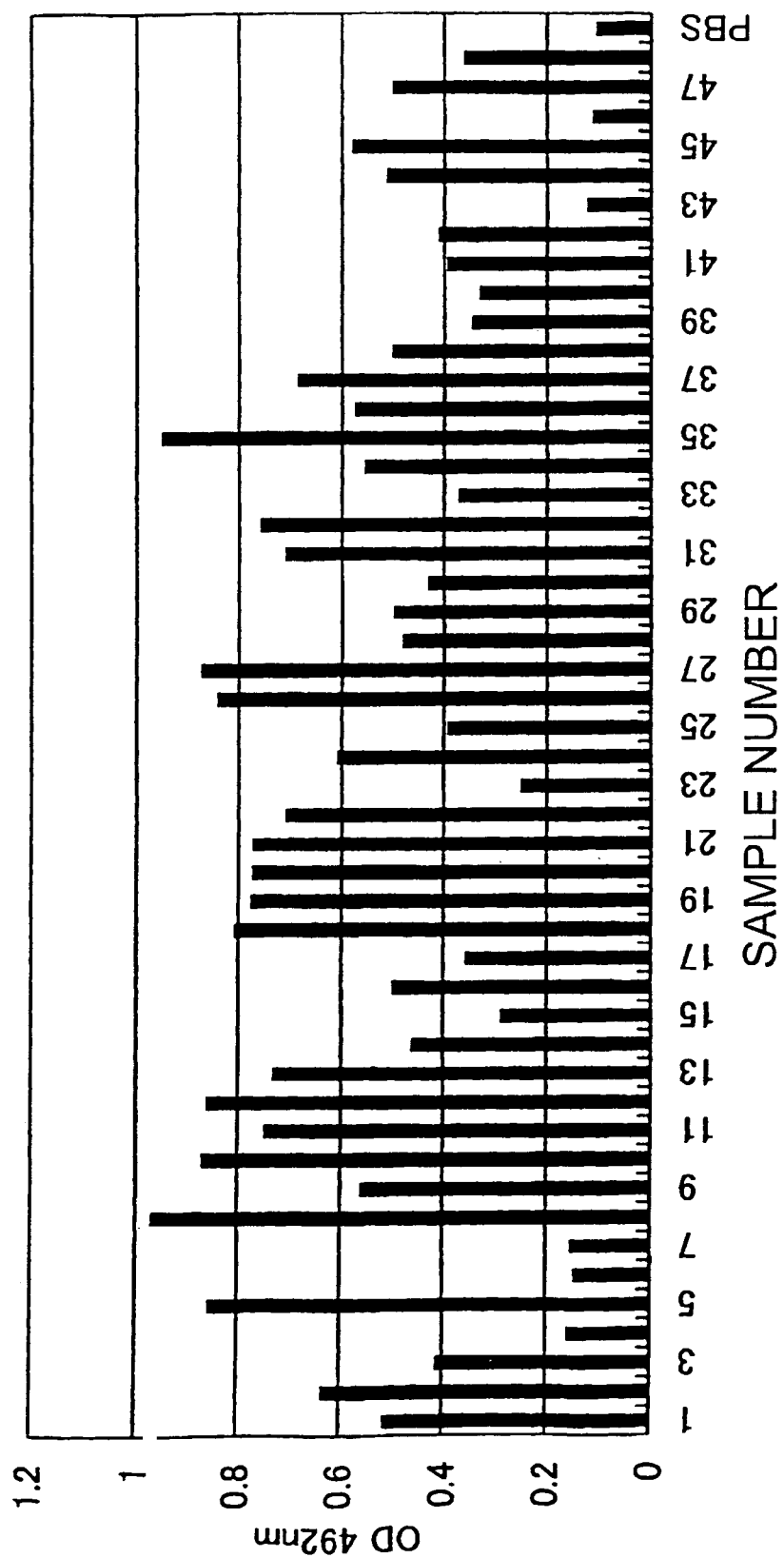
FIG. 18 shows the result of ELISA confirming the responsiveness of VHH (IgM) clones to β-Gal. The vertical axis shows the absorbance (OD 492 nm) and the horizontal axis shows the sample number.

Monoclones were prepared from phage clones obtained from the third screening by a method similar to that for GST antibodies of Example 3. When ELISA was performed by a method similar to that for GST antibodies of Example 3, 43 clones out of 48 clones were ELISA positive. (FIG. 18)

INDUSTRIAL APPLICABILITY

The present invention provides VHH libraries that maintain the in vivo diversity of the VHH region. Furthermore, VHHs constituting the libraries of the present invention comprise many normal nucleotide sequences, and they have a high expression rate. Thus, it can be stated that the VHH libraries of this invention are composed of active VHHs. Therefore, using a VHH library of the present invention, a VHH having binding affinity for any arbitrary antigen can be freely obtained.

In general, camelids that have not been immunologically sensitized had been considered to provide only VHHs having binding affinity for antigens with strong immunogenicity. However, the present inventors realized a VHH library that freely provides VHHs having a wide variety of functions by enlarging the repertoire size of the library. The present invention greatly contributes to the industrial use of VHHs by providing libraries that require no immunological sensitization and having richer diversity compared to known libraries.

On the other hand, conventional methods for constructing libraries did take no account of limitations or bias of in vivo VHH repertoire size in an individual. As a result, the diversity of VHH libraries constructed by conventional methods did not reflect the in vivo diversity of the VHH region. This is also obvious from the fact that many of the VHH classes classified in Table 1 have structural characteristics newly found in the libraries of the present invention. Methods to increase the diversity of libraries by artificially introducing mutations are well known in the art. However, the methods of artificially introducing mutations accompany inefficiency of producing far too many inactive antibodies along with the production of active antibodies. As a result, VHH libraries constructed based on conventional methods did not fulfill the requirement of a VHH library, i.e., composed of active VHHs with rich diversity.

A VHH has excellent characteristics in solubility and stability compared to that of a generally used VH constituting IgG. Furthermore, a binding activity difficult to obtain for IgG composed of VHs can be expected from VHHs. However, according to the findings of the present inventors, the in vivo repertoire size of VHHs in an individual is restricted. Therefore, as long as libraries are constructed based on conventional library production methods, the repertoire size of a VHH library cannot exceed the in vivo repertoire size of an individual. Thus, although various utilities are expected from VHHs, the possibility to obtain a VHH having the desired function is extremely low when known VHH libraries are utilized.

The present invention enables to freely obtain industrially useful VHHs by providing VHH libraries having a diversity exceeding the in vivo repertoire size of an individual. In other words, VHHs having the desired function were made accessible for the first time due to the libraries of the present invention.

This is also apparent from the result of the Examples wherein VHHs having the function of regulating enzyme activity are easily selected. Furthermore, in the Examples, a plurality of VHHs having various effects on a plurality of enzymes was selected. The great diversity of the libraries of the present invention as well as the activity of VHH different from that of VH enables to readily select such VHHs having various functions.

In addition, a library consisting of IgM-derived VHs provided by the present invention is useful as a library that additionally supplements the above-mentioned VHH libraries having diversity. Therefore, the use of an IgM-derived VH library of the present invention enables selection of antibody variable regions that cannot be selected from VHHs or those having functions that are difficult to select due to small population size.

SEQUENCE LISTING

```
<160> NUMBER OF SEQ ID NOS: 42

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 1
gtcctcgcaa ctgcggccca gccggccatg gccgaggtgc agctggtgga gtctgg         56

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 2
gtcctcgcaa ctgcggccca gccggccatg gcccaggtrc agctggtgga gtctgg         56

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
```

```
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 3
gtcctcgcaa ctgcggccca gccggccatg gcccaggtaa agctggagga gtctgg          56

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 4
gtcctcgcaa ctgcggccca gccggccatg gccgatgtgc agctggtgga gtctgg          56

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 5
gtcctcgcaa ctgcggccca gccggccatg gccgccgtgc agctggtgga ttctgg          56

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (15)..(18)
<223> OTHER INFORMATION: SfiI site
<220> FEATURE:
<221> NAME/KEY: misc_feature
<222> LOCATION: (24)..(27)
<223> OTHER INFORMATION: SfiI site

<400> SEQUENCE: 6
gtcctcgcaa ctgcggccca gccggccatg gccgcggtgc agctggtgga gtctgg          56

<210> SEQ ID NO 7
<211> LENGTH: 12
```

```
<212> TYPE: PRT
<213> ORGANISM: Camelus dromedarius

<400> SEQUENCE: 7

Glu Pro His Gly Gly Cys Pro Cys Pro Lys Cys Pro
 1               5                  10

<210> SEQ ID NO 8
<211> LENGTH: 35
<212> TYPE: PRT
<213> ORGANISM: Camelus dromedarius

<400> SEQUENCE: 8

Glu Pro Lys Ile Pro Gln Pro Gln Pro Lys Pro Gln Pro Gln Pro Gln
 1               5                  10                  15

Pro Gln Pro Lys Pro Gln Pro Lys Pro Glu Pro Glu Cys Thr Cys Pro
                20                  25                  30

Lys Cys Pro
        35

<210> SEQ ID NO 9
<211> LENGTH: 12
<212> TYPE: PRT
<213> ORGANISM: Camelus dromedarius

<400> SEQUENCE: 9

Gly Thr Asn Glu Val Cys Lys Cys Pro Lys Cys Pro
 1               5                  10

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
aaggcgcgcc ccttggggta tcttgggttc tg                              32

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
aaggcgcgcc cctgatactt cattcgttcc tgavgag                         37

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12
aacagctatg accatg                                                16

<210> SEQ ID NO 13
<211> LENGTH: 42
<212> TYPE: DNA
```

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 13

```
cgactgaagg cgcgcccctc tcgagaccct gaccgtggtg cc                               42
```

<210> SEQ ID NO 14
<211> LENGTH: 378
<212> TYPE: DNA
<213> ORGANISM: Camelus dromedarius

<400> SEQUENCE: 14

```
gcggtgcagt tggtggagtc tgggggaggc tcggtgcaga cgggagggtc tctgagactc           60
tcctgtgcag cctctggaga cacctccagt accaactgca tggcctggtt cgccagcgt            120
ccagggaagg agcgcgaggg ggtcgcacat atttatactc gtgacggtag aatatactat          180
gccgactccg tgaagggccg attcaccatc tcccgagaca aggccaagaa tgaggtgtat          240
ttgcaaatga acggcctgaa acctgaggac actgccatgt actactgtgc agcagttagt          300
ggtcgtgcat attgtagtgg aatgtcaata tatggggata gcgatttggg ccaggggacc          360
caggtcaccg tctcctca                                                       378
```

<210> SEQ ID NO 15
<211> LENGTH: 126
<212> TYPE: PRT
<213> ORGANISM: Camelus dromedarius

<400> SEQUENCE: 15

```
Ala Val Gln Leu Val Glu Ser Gly Gly Gly Ser Val Gln Thr Gly Gly
  1               5                  10                  15

Ser Leu Arg Leu Ser Cys Ala Ala Ser Gly Asp Thr Ser Ser Thr Asn
             20                  25                  30

Cys Met Ala Trp Leu Arg Gln Arg Pro Gly Lys Glu Arg Glu Gly Val
         35                  40                  45

Ala His Ile Tyr Thr Arg Asp Gly Arg Ile Tyr Tyr Ala Asp Ser Val
     50                  55                  60

Lys Gly Arg Phe Thr Ile Ser Arg Asp Lys Ala Lys Asn Glu Val Tyr
 65                  70                  75                  80

Leu Gln Met Asn Gly Leu Lys Pro Glu Asp Thr Ala Met Tyr Tyr Cys
                 85                  90                  95

Ala Ala Val Ser Gly Arg Ala Tyr Cys Ser Gly Met Ser Ile Tyr Gly
            100                 105                 110

Asp Ser Asp Leu Gly Gln Gly Thr Gln Val Thr Val Ser Ser
        115                 120                 125
```

<210> SEQ ID NO 16
<211> LENGTH: 384
<212> TYPE: DNA
<213> ORGANISM: Camelus dromedarius

<400> SEQUENCE: 16

```
gaggtgcagc tggtggagtc tgggggaggc tcggtgcagg ccggagggtc tctgaaactc           60
tcctgtggac tctctggata caccagcagt atgaacgcca tgggctggtt ccgccaggct          120
ccagggaagg agcgtgaggg ggtcgccgct gttagtcgtg gttaaggc atactacgcc           180
gactccgtga agggccggtt caccgtctcc cgcgacaatg tcaagaatac agtggatcta          240
```

```
caaatgaagg gcctgaaagc tgaggacacg gccacctatt actgcgcggc aactgacgag      300
tctcctttac gacgaagatt cagcctcttg gatcggaggc gctatgactg gtggggccgg      360
gggacccagg tcttcgtctc ttca                                             384
```

<210> SEQ ID NO 17
<211> LENGTH: 128
<212> TYPE: PRT
<213> ORGANISM: Camelus dromedarius

<400> SEQUENCE: 17

```
Glu Val Gln Leu Val Glu Ser Gly Gly Gly Ser Val Gln Ala Gly Gly
 1               5                  10                  15

Ser Leu Lys Leu Ser Cys Gly Leu Ser Gly Tyr Thr Ser Ser Met Asn
                20                  25                  30

Ala Met Gly Trp Phe Arg Gln Ala Pro Gly Lys Glu Arg Glu Gly Val
            35                  40                  45

Ala Ala Val Ser Arg Gly Gly Lys Ala Tyr Tyr Ala Asp Ser Val Lys
        50                  55                  60

Gly Arg Phe Thr Val Ser Arg Asp Asn Val Lys Asn Thr Val Asp Leu
    65                  70                  75                  80

Gln Met Lys Gly Leu Lys Ala Glu Asp Thr Ala Thr Tyr Tyr Cys Ala
                85                  90                  95

Ala Thr Asp Glu Ser Pro Leu Arg Arg Arg Phe Ser Leu Leu Asp Arg
           100                 105                 110

Arg Arg Tyr Asp Trp Trp Gly Arg Gly Thr Gln Val Phe Val Ser Ser
           115                 120                 125
```

<210> SEQ ID NO 18
<211> LENGTH: 375
<212> TYPE: DNA
<213> ORGANISM: Camelus dromedarius

<400> SEQUENCE: 18

```
gccgtgcagc tggtggattc tggggggaggc tcggtgcagg ctggagggtc tctgagactc      60
tcctgtgcag cctctgggac cacatattgt acgtacgaca tagcctggta ccgccaggct     120
ccagagaagg actacgagtt cgtctcagtt attgatagtg atggtagtac aaggtacgca     180
gactccgtga agggccgatt taccatctcc cgagacaacg ccaagaacac ggtgtatctg     240
caaatgaaca gtttgaaacc tgaggacacg gcgatgtatt actgtaaaac agttttaag      300 tcttggtgta gtgacggctt gggtacgacg ttgcctaact actggggcca ggggacccag     360
gtcaccgtct cctca                                                      375
```

<210> SEQ ID NO 19
<211> LENGTH: 125
<212> TYPE: PRT
<213> ORGANISM: Camelus dromedarius

<400> SEQUENCE: 19

```
Ala Val Gln Leu Val Asp Ser Gly Gly Gly Ser Val Gln Ala Gly Gly
 1               5                  10                  15

Ser Leu Arg Leu Ser Cys Ala Ala Ser Gly Thr Thr Tyr Cys Thr Tyr
                20                  25                  30

Asp Ile Ala Trp Tyr Arg Gln Ala Pro Glu Lys Asp Tyr Glu Phe Val
            35                  40                  45

Ser Val Ile Asp Ser Asp Gly Ser Thr Arg Tyr Ala Asp Ser Val Lys
        50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Met Tyr Tyr Cys Lys
                 85                  90                  95

Thr Val Phe Lys Ser Trp Cys Ser Asp Gly Leu Gly Thr Thr Leu Pro
            100                 105                 110

Asn Tyr Trp Gly Gln Gly Thr Gln Val Thr Val Ser Ser
        115                 120                 125

<210> SEQ ID NO 20
<211> LENGTH: 378
<212> TYPE: DNA
<213> ORGANISM: Camelus dromedarius

<400> SEQUENCE: 20
gcggtgcagc tggtggagtc tgggggaggc tcggtgcaga ctggagggtc tctgagactc      60
tcctgtgtag cctctggata cacctacagt agcgcgcgca tcggctggtt ccgccaggct    120
ccagggaagg agcgcgaggg ggtcgcagct atcttgactg atggtgtaac cacatactat    180
gccgacgccg tgaagggccg attcaccatc tccagagaca cgccaagaa cacggtgtat     240 ctgcagatga acagcctgaa acctgaggac actgccatgt actactgtgc aatccggact    300
tccccctaca gtggtgggtg gtttcgcgtt agtcagtata cggctgggg ccaggggacc     360 caggtcaccg tctcctca                                                  378

<210> SEQ ID NO 21
<211> LENGTH: 126
<212> TYPE: PRT
<213> ORGANISM: Camelus dromedarius

<400> SEQUENCE: 21

Ala Val Gln Leu Val Glu Ser Gly Gly Gly Ser Val Gln Thr Gly Gly
  1               5                  10                  15

Ser Leu Arg Leu Ser Cys Val Ala Ser Gly Tyr Thr Tyr Ser Ser Ala
             20                  25                  30

Arg Ile Gly Trp Phe Arg Gln Ala Pro Gly Lys Glu Arg Glu Gly Val
         35                  40                  45

Ala Ala Ile Leu Thr Asp Gly Val Thr Thr Tyr Tyr Ala Asp Ala Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ile Arg Thr Ser Pro Tyr Ser Gly Gly Trp Phe Arg Val Ser Gln
            100                 105                 110

Tyr Asn Gly Trp Gly Gln Gly Thr Gln Val Thr Val Ser Ser
        115                 120                 125

<210> SEQ ID NO 22
<211> LENGTH: 372
<212> TYPE: DNA
<213> ORGANISM: Camelus dromedarius

<400> SEQUENCE: 22
gatgtgcagc tggtggagtc tgggggaggc tcggagcagg ctggaggttc tctgagactc      60
tcctgtgcag cccctaatat aacctactgt accggcgaca ggagctggta ccgccaggct    120
```

```
ccagggaagg agcgcgagtt cgtctcatcg attaataatg atggtacagc aagctacgca    180
gactccgtga agggccgatt caccatctcc aagacattg ttaagaaatc ggtctatctg      240
cggatgaaca gcctgaaacc tgaggacacg gcgatgtatt actgtaaaac agacttcgtc    300
gatggtacct ggtgcgcgat aaagttcggg cgtactcact ggggccaggg gacccaggtc    360
accgtctcct ca                                                         372
```

```
<210> SEQ ID NO 23
<211> LENGTH: 124
<212> TYPE: PRT
<213> ORGANISM: Camelus dromedarius

<400> SEQUENCE: 23
```

Asp Val Gln Leu Val Glu Ser Gly Gly Gly Ser Glu Gln Ala Gly Gly
 1               5                   10                  15

Ser Leu Arg Leu Ser Cys Ala Ala Pro Asn Ile Thr Tyr Cys Thr Gly
            20                  25                  30

Asp Arg Ser Trp Tyr Arg Gln Ala Pro Gly Lys Glu Arg Glu Phe Val
        35                  40                  45

Ser Ser Ile Asn Asn Asp Gly Thr Ala Ser Tyr Ala Asp Ser Val Lys
    50                  55                  60

Gly Arg Phe Thr Ile Ser Gln Asp Ile Val Lys Ser Val Tyr Leu
65                  70                  75                  80

Arg Met Asn Ser Leu Lys Pro Glu Asp Thr Ala Met Tyr Tyr Cys Lys
                85                  90                  95

Thr Asp Phe Val Asp Gly Thr Trp Cys Ala Ile Lys Phe Gly Arg Thr
            100                 105                 110

His Trp Gly Gln Gly Thr Gln Val Thr Val Ser Ser
        115                 120

```
<210> SEQ ID NO 24
<211> LENGTH: 375
<212> TYPE: DNA
<213> ORGANISM: Camelus dromedarius

<400> SEQUENCE: 24
```

```
gaggtgcagc tggtggagtc tgggggaggc tcggtgcagg ctggagattc tctgagactc     60
tcttgtacaa cctctggatt cactttttgcg aactctgtca tggtctggta ccgccagggt   120
tcaggaaacg agtgtaaatt ggtctcaagt ataagtactg acggtactac atactattca   180
acttccgtga agggccgatt caccatctcc agagacaacc caagaacac ggtctatttg     240 caaatgaaca atctgaaagc cgaggacacg gccatgtatt actgtgcggc agatttccag   300
gcttctacgg tggggcgttg cgacggatat ggatatgcta atggggcca ggggacccag    360 gtcaccgtct cctca                                                     375
```

```
<210> SEQ ID NO 25
<211> LENGTH: 125
<212> TYPE: PRT
<213> ORGANISM: Camelus dromedarius

<400> SEQUENCE: 25
```

Glu Val Gln Leu Val Glu Ser Gly Gly Gly Ser Val Gln Ala Gly Asp
 1               5                   10                  15

Ser Leu Arg Leu Ser Cys Thr Thr Ser Gly Phe Thr Phe Ala Asn Ser
            20                  25                  30

Val Met Val Trp Tyr Arg Gln Gly Ser Gly Asn Glu Cys Lys Leu Val

```
                35                  40                  45
Ser Ser Ile Ser Thr Asp Gly Thr Thr Tyr Tyr Ser Thr Ser Val Lys
 50                  55                  60

Gly Arg Phe Thr Ile Ser Arg Asp Asn Ala Lys Asn Thr Val Tyr Leu
 65                  70                  75                  80

Gln Met Asn Asn Leu Lys Ala Glu Asp Thr Ala Met Tyr Tyr Cys Ala
                 85                  90                  95

Ala Asp Phe Gln Ala Ser Thr Val Gly Arg Cys Asp Gly Tyr Gly Tyr
            100                 105                 110

Ala Lys Trp Gly Gln Gly Thr Gln Val Thr Val Ser Ser
        115                 120                 125

<210> SEQ ID NO 26
<211> LENGTH: 369
<212> TYPE: DNA
<213> ORGANISM: Camelus dromedarius

<400> SEQUENCE: 26
gcggtgcagc tggtggagtc tgggggaggc tcggtgcagg caggaggatt tctgagactc      60
tcctgtgtag cctctgttaa ttactgcatg gcctggttcc gccaggctcc agggaaggag     120
cgtgaggggg tcgcagcaat taatagagac ggtcgtacta ctgcctacgc cgactccgtg     180
aagggccgat tcaccatctc ccgaggcaac gagaagaaca cggtgtatct actaatgaac     240
aacctgaaag ccgaggacac ggccacctat tactgtgcgg cctacgtcgg tggtagttac     300
tcctgcggta ctttggagaa cgatggatat aagtactggg gccaggggac ccaggtcacc     360
gtctcctca                                                             369

<210> SEQ ID NO 27
<211> LENGTH: 123
<212> TYPE: PRT
<213> ORGANISM: Camelus dromedarius

<400> SEQUENCE: 27

Ala Val Gln Leu Val Glu Ser Gly Gly Gly Ser Val Gln Ala Gly Gly
  1               5                  10                  15

Phe Leu Arg Leu Ser Cys Val Ala Ser Val Asn Tyr Cys Met Ala Trp
             20                  25                  30

Phe Arg Gln Ala Pro Gly Lys Glu Arg Glu Gly Val Ala Ala Ile Asn
         35                  40                  45

Arg Asp Gly Arg Thr Thr Ala Tyr Ala Asp Ser Val Lys Gly Arg Phe
 50                  55                  60

Thr Ile Ser Arg Gly Asn Glu Lys Asn Thr Val Tyr Leu Leu Met Asn
 65                  70                  75                  80

Asn Leu Lys Ala Glu Asp Thr Ala Thr Tyr Tyr Cys Ala Ala Tyr Val
                 85                  90                  95

Gly Gly Ser Tyr Ser Cys Gly Thr Leu Glu Asn Asp Gly Tyr Lys Tyr
            100                 105                 110

Trp Gly Gln Gly Thr Gln Val Thr Val Ser Ser
        115                 120

<210> SEQ ID NO 28
<211> LENGTH: 372
<212> TYPE: DNA
<213> ORGANISM: Camelus dromedarius

<400> SEQUENCE: 28
```

-continued

```
gaggtgcagc tggtggagtc tggggggaggc tcggtgcagg ctggagggtc tctaagactc    60
tcctgtgcag cgcctggaaa tacctatagt accaacttga tgggctggtt ccgccaggct   120
ccagggaagg agcgcgaggg ggtcgcagct atttgctgtg gtcgtggtac cacattctac   180
gccgactccg tgaagggccg attcaccatc tcccaagaca cgccaagaa  gatggtgtat   240 ctgcaaatgg agctcctgag gcctgaggac actggcatct actactgtgc aagtgggtca   300
gtccgcggaa tttggtcggg cacaagtcag tataagtact ggggccaggg gacccaggtc   360
accgtctcct ca                                                       372
```

<210> SEQ ID NO 29
<211> LENGTH: 124
<212> TYPE: PRT
<213> ORGANISM: Camelus dromedarius

<400> SEQUENCE: 29

```
Glu Val Gln Leu Val Glu Ser Gly Gly Gly Ser Val Gln Ala Gly Gly
 1               5                  10                  15

Ser Leu Arg Leu Ser Cys Ala Ala Pro Gly Asn Thr Tyr Ser Thr Asn
            20                  25                  30

Leu Met Gly Trp Phe Arg Gln Ala Pro Gly Lys Glu Arg Glu Gly Val
        35                  40                  45

Ala Ala Ile Cys Cys Gly Arg Gly Thr Thr Phe Tyr Ala Asp Ser Val
    50                  55                  60

Lys Gly Arg Phe Thr Ile Ser Gln Asp Asn Ala Lys Lys Met Val Tyr
65                  70                  75                  80

Leu Gln Met Glu Leu Leu Arg Pro Glu Asp Thr Gly Ile Tyr Tyr Cys
                85                  90                  95

Ala Ser Gly Ser Val Arg Gly Ile Trp Ser Gly Thr Ser Gln Tyr Lys
            100                 105                 110

Tyr Trp Gly Gln Gly Thr Gln Val Thr Val Ser Ser
        115                 120
```

<210> SEQ ID NO 30
<211> LENGTH: 348
<212> TYPE: DNA
<213> ORGANISM: Camelus dromedarius

<400> SEQUENCE: 30

```
caggtgcagc tggtggagtc tgggggaggc ttggtgcagc ccggggggtc tctgagactc    60
tcctgtgcag cctctggatt cagcttcagt agaagtggca tgagctgggg ccgccaggct   120
ccagggaagg ggttcgagtg gtctcgcgt  atcagtagtg gtggagccac atggtacgca   180
gattccgtga agggccgatt cagcatttcc agagacaacg ccaagaatac tgtgtatttg   240
caattggaca gcctgaaaac tgaggacacg gcatgtatt  actgtgcagc aagcgatcgg   300
tctggctcga cttaccgggg ccaggggacc caggtcaccg tctcctca              348
```

<210> SEQ ID NO 31
<211> LENGTH: 116
<212> TYPE: PRT
<213> ORGANISM: Camelus dromedarius

<400> SEQUENCE: 31

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ser Arg Ser
            20                  25                  30
```

```
Gly Met Ser Trp Gly Arg Gln Ala Pro Gly Lys Gly Phe Glu Trp Val
         35                  40                  45

Ser Arg Ile Ser Ser Gly Gly Ala Thr Trp Tyr Ala Asp Ser Val Lys
     50                  55                  60

Gly Arg Phe Ser Ile Ser Arg Asp Asn Ala Lys Asn Thr Val Tyr Leu
 65                  70                  75                  80

Gln Leu Asp Ser Leu Lys Thr Glu Asp Thr Gly Met Tyr Tyr Cys Ala
                 85                  90                  95

Ala Ser Asp Arg Ser Gly Ser Thr Tyr Arg Gly Gln Gly Thr Gln Val
             100                 105                 110

Thr Val Ser Ser
         115
```

<210> SEQ ID NO 32
<211> LENGTH: 381
<212> TYPE: DNA
<213> ORGANISM: Camelus dromedarius

<400> SEQUENCE: 32

```
gaggtgcagc tggtggagtc tgggggagac tcggtgcagg ctggagggtc tctgagactc     60
tcctgtgtag cctcgtcaag cacctacagt ggcaactgca tggcctggtt ccgccaggct    120
ccagggaagg agcgcgaggg ggtcgcagtt gtttatactg acgatgatac acatactat    180
gccgactccg tgaagggccg attcaccatc tcccaagaca ccgccaagaa cacgctatat    240
ctgcaaatga atagcctgaa acctgaggac actgccatgt actactgtgc aacaagggac    300
gcctggcgac ggattgggtc ctggagagac gttgcgattt atgactactg gggccagggg    360
acccaggtca ccgtctcctc a                                              381
```

<210> SEQ ID NO 33
<211> LENGTH: 127
<212> TYPE: PRT
<213> ORGANISM: Camelus dromedarius

<400> SEQUENCE: 33

```
Glu Val Gln Leu Val Glu Ser Gly Gly Asp Ser Val Gln Ala Gly Gly
  1               5                  10                  15

Ser Leu Arg Leu Ser Cys Val Ala Ser Ser Ser Thr Tyr Ser Gly Asn
             20                  25                  30

Cys Met Ala Trp Phe Arg Gln Ala Pro Gly Lys Glu Arg Glu Gly Val
         35                  40                  45

Ala Val Val Tyr Thr Asp Asp Thr Thr Tyr Tyr Ala Asp Ser Val
     50                  55                  60

Lys Gly Arg Phe Thr Ile Ser Gln Asp Thr Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Arg Asp Ala Trp Arg Arg Ile Gly Ser Trp Arg Asp Val Ala
             100                 105                 110

Ile Tyr Asp Tyr Trp Gly Gln Gly Thr Gln Val Thr Val Ser Ser
         115                 120                 125
```

<210> SEQ ID NO 34
<211> LENGTH: 372
<212> TYPE: DNA
<213> ORGANISM: Camelus dromedarius

```
<400> SEQUENCE: 34
gaggtgcagc tggtggagtc tgggggaggc tcggtgcagg ctggagggtc tctgagactc        60
tcctgtgcag cctctggata caccagcggt cgcaactaca tggcctggtt ccgccaggct       120
ccagggaagg agcgcgaggg ggtcggacgt atttattcta ccggtggtag cgcgcgctat       180
gccgactccg tgaagggccg attcaccatc tcccaagacc tgtccaacga cacgatgtat       240
ctgcaaatga caacctgaa acctgaggac actggcatgt actactgtgc agccgggaaa       300
ccctacggtg atatgcttga tgcacgcggg tataagtact ggggccacgg gacccaggtc       360
accgtctcct ca                                                          372

<210> SEQ ID NO 35
<211> LENGTH: 124
<212> TYPE: PRT
<213> ORGANISM: Camelus dromedarius

<400> SEQUENCE: 35

Glu Val Gln Leu Val Glu Ser Gly Gly Gly Ser Val Gln Ala Gly Gly
  1               5                  10                  15

Ser Leu Arg Leu Ser Cys Ala Ala Ser Gly Tyr Thr Ser Gly Arg Asn
             20                  25                  30

Tyr Met Ala Trp Phe Arg Gln Ala Pro Gly Lys Glu Arg Glu Gly Val
         35                  40                  45

Gly Arg Ile Tyr Ser Thr Gly Gly Ser Ala Arg Tyr Ala Asp Ser Val
     50                  55                  60

Lys Gly Arg Phe Thr Ile Ser Gln Asp Leu Ser Asn Asp Thr Met Tyr
 65                  70                  75                  80

Leu Gln Met Asn Asn Leu Lys Pro Glu Asp Thr Gly Met Tyr Tyr Cys
                 85                  90                  95

Ala Ala Gly Lys Pro Tyr Gly Asp Met Leu Asp Ala Arg Gly Tyr Lys
            100                 105                 110

Tyr Trp Gly His Gly Thr Gln Val Thr Val Ser Ser
        115                 120

<210> SEQ ID NO 36
<211> LENGTH: 77
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 36
gtcaccgtct cgagaggcgg tggcggatca ggtggcggtg aagtggcgg tggtgggtcc        60 atggccgaca tcgagct                                                      77

<210> SEQ ID NO 37
<211> LENGTH: 68
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 37
cgatgtcggc catggaccca ccaccgccac ttcaccgcc acctgatccg ccaccgcctc        60
tcgagacg                                                                68
```

```
<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 38
aacgtaggcg cgccggactt gtccacggtc ctctc                              35

<210> SEQ ID NO 39
<211> LENGTH: 33
<212> TYPE: DNA
<213> ORGANISM: Camelus dromedarius

<400> SEQUENCE: 39
gagagctcat ctgccccgac actcttcccc ctc                                33

<210> SEQ ID NO 40
<211> LENGTH: 11
<212> TYPE: PRT
<213> ORGANISM: Camelus dromedarius

<400> SEQUENCE: 40

Glu Ser Ser Ser Ala Pro Thr Leu Tyr Pro Leu
 1               5                  10

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 41
acattaatct ggcgcgccga gagtgtcggg gcagatgagc tctc                    44

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 42
aaggcgcgcc cctgavgagr yggtgacyhg                                    30
```

The invention claimed is:

1. A method of constructing a VHH library, comprising the steps of:
   (1) amplifying by polymerase chain reaction (PCR) a VHH gene from a non-immunized *Camelus dromedarius* by contacting the VHH gene with at least one oligonucleotide having the nucleotide sequence selected from the group consisting of SEQ ID NO: 10 and SEQ ID NO: 11, and (2) preparing a library by mixing the VHH genes obtained in step (1), thereby constructing a VHH library.

2. The method of claim 1, wherein the VHH library comprises at least $10^5$ VHHs identical to naturally occurring VHHs derived from non-immunized *Camelus dromedarius*.

3. The method of claim 1, wherein the VHH library comprises VHHs belonging to at least 8 or more VHH classes.

4. The method of claim 3, wherein the VHH library comprises VHHs of at least 6 VHH subfamilies, wherein said VHHs belong to 15 or more classes.

5. The method of claim 1, wherein the VHH library comprises VHH immunoglobulins selected from the group consisting of IgG2, IgG3, and mixtures thereof.

6. The method of claim 1, wherein the VHH library comprises 60% or more VHHs.

7. The method of claim 1, further comprising contacting the VHH gene with at least one oligonucleotide having the nucleotide sequence selected from the group consisting of SEQ ID NO:1, SEQ ID NO:2, SEQ ID NO:3, SEQ ID NO:4, SEQ ID NO:5 and SEQ ID NO:6.

8. The method of claim 1, comprising a step of collecting amplification products of the PCR during the exponential phase.

9. The method of claim 1, wherein the PCR is performed using a primer set consisting of a 5' primer selected from any one of the oligonucleotides having the nucleotide sequence selected from the group consisting of SEQ ID NO:1, SEQ ID NO:2, SEQ ID NO:3, SEQ ID NO:4, SEQ ID NO:5 and SEQ ID NO:6 and a 3' primer having the nucleotide sequence of SEQ ID NO:10, and which comprises the step of mixing amplification products from the primer set.

10. The method of claim 1, wherein the PCR is performed using a primer set consisting of a 5' primer selected from any one of the oligonucleotides having the nucleotide sequence selected from the group consisting of SEQ ID NO:1, SEQ ID NO:2, SEQ ID NO:3, SEQ ID NO:4, SEQ ID NO:5 and SEQ ID NO:6 and a 3' primer having the nucleotide sequence of SEQ ID NO:11, and which comprises the step of mixing amplification products from the primer set.

11. The method of claim 9 or 10, comprising a step of digesting the amplification products with restriction enzymes SfiI and AscI and ligating the digested products into a vector having features (i) and (ii) as follows:

(i) comprising a SfiI site and an AscI site; and (ii) upon transformation of the vector into an appropriate host, expressing a protein encoded by an exogenous gene inserted into the site of (i) as a fusion protein with a protein constituting a phage.

12. An isolated oligonucleotide having the nucleotide sequence of SEQ ID NO:10 or SEQ ID NO:11.

13. A reaction mixture comprising at least one oligonucleotide having the nucleotide sequence of SEQ ID NO:10 or SEQ ID NO:11.

14. The reaction mixture of claim 13, further comprising at least one oligonucleotide selected from the group consisting of SEQ ID NO:1, SEQ ID NO:2, SEQ ID NO:3, SEQ ID NO:4, SEQ ID NO:5 and SEQ ID NO:6.

15. The reaction mixture of claim 13, further comprising a target nucleic acid identical to a cDNA or complement thereof from a non-immunized *Camelus dromedarius*.

16. A primer set comprising a 5' primer having the nucleotide sequence selected from the group consisting of SEQ ID NO:1, SEQ ID NO:2, SEQ ID NO:3, SEQ ID NO:4, SEQ ID NO:5 and SEQ ID NO:6, and a 3' primer having the nucleotide sequence selected from the group consisting of SEQ ID NO:10 and SEQ ID NO:11.

17. The reaction mixture of claim 13, further comprising a sample from a non-immunized *Camelus dromedarius*.

* * * * *

UNITED STATES PATENT AND TRADEMARK OFFICE
CERTIFICATE OF CORRECTION

PATENT NO.       : 7,371,849 B2
APPLICATION NO.  : 10/489477
DATED            : May 13, 2008
INVENTOR(S)      : Honda et al.

It is certified that error appears in the above-identified patent and that said Letters Patent is hereby corrected as shown below:

In the SEQUENCE LISTING, beginning below columns 47 and 48, the first line of text under "SEQUENCE LISTING" should read as follows:

--<160> NUMBER OF SEQ ID NOS: 52--

In the SEQUENCE LISTING at columns 69 and 70, immediately following the text of SEQUENCE 42, the following SEQ ID NOS: 43 through 52 should be inserted prior to "The invention claimed is:":

```
-- <210>  43
<211>  1420
<212>  DNA
<213>  Artificial

<220>
<223>  An artificially synthesized vector sequence

<400>  43
aagcttgcat gcaaattcta tttcaaggag acagtcataa tgaaatacct attgcctacg     60
gcagccgctg gattgttatt actcgcggcc cagccggcca tggccgaggt tcagctgcag    120
cagtctgggg cagagcttgt gaagccaggg gcctcagtca agttgtcctg cacagcttct    180
ggcttcaaca ttaaagacac ctatatgcac tgggtgaagc agaggcctga aaagggtcta    240
gaattccctg acatctgagg acactgccgt ctattactgt gctggttatg attacggcaa    300
ctttgactac tggggccaag gcaccacggt cagggtctcg agagggcgc gccagtcgac    360
```

UNITED STATES PATENT AND TRADEMARK OFFICE
CERTIFICATE OF CORRECTION

PATENT NO.       : 7,371,849 B2
APPLICATION NO.  : 10/489477
DATED            : May 13, 2008
INVENTOR(S)      : Honda et al.

It is certified that error appears in the above-identified patent and that said Letters Patent is hereby corrected as shown below:

```
tccattcgtt tgtgaatatc aaggccaatc gtctgacctg cctcaacctc ctgtcaatgc    420
tggcggcggc tctggtggtg gttctggtgg cggctctgag ggtggtggct ctgagggtgg    480
cggttctgag ggtggcggct ctgagggagg cggttccggt ggtggctctg gttccggtga    540
ttttgattat gaaaagatgg caaacgctaa taaggggggct atgaccgaaa atgccgatga   600
aaacgcgcta cagtcagacg ctaaaggcaa acttgattct gtcgctactg attacggtgc    660
tgctatcgat ggtttcattg gtgacgtttc cggccttgct aatggtaatg gtgctactgg    720
tgattttgct ggctctaatt cccaaatggc tcaagtcggt gacggtgata attcaccttt    780
aatgaataat ttccgtcaat atttaccttc cctccctcaa tcggttgaat gtcgcccttt    840
tgtctttggc gctggtaaac catatgaatt ttctattgat tgtgacaaaa taaacttatt    900
ccgtggtgtc tttgcgtttc ttttatatgt tgccaccttt atgtatgtat tttctacgtt    960
tgctaacata ctgcgtaata aggagtctta atcatgccag ttcttttggg tgctagctgt    1020
cgactgcgca acacgatgaa gccgtagaca acaaattcaa caaagaacaa caaaacgcgt    1080
tctatgagat cttacattta cctaacttaa acgaagaaca acgaaacgcc ttcatccaaa    1140
gtttaaaaga tgacccaagc caaagcgcta acctttagc agaagctaaa aagctaaatg     1200
atgctcaggc gccgaaagta gacaacaaat tcaacaaaga acaacaaaac gcgttctatg    1260
agatcttaca tttacctaac ttaaacgaag aacaacgaaa cgccttcatc caaagtttaa    1320
aagatgaccc aagccaaagc gctaaccttt tagtagaagc taaaaagcta aatgatgctc    1380
aggcgccgaa agtagacgcg aattagctgg gaattaattc                         1420
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
<210>   44
<211>   441
<212>   PRT
<213>   Artificial

<220>
<223>   An artificially synthesized vector sequence

<400>   44

Met Lys Tyr Leu Leu Pro Thr Ala Ala Ala Gly Leu Leu Leu Leu Ala
1               5                   10                  15

Ala Gln Pro Ala Met Ala Glu Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Tyr Met His Trp Val Lys Gln Arg Pro Glu
    50                  55                  60

Lys Gly Leu Thr Ser Glu Asp Thr Ala Val Tyr Tyr Cys Ala Gly Tyr
65                  70                  75                  80

Asp Tyr Gly Asn Phe Asp Tyr Trp Gly Gln Gly Thr Thr Val Arg Val
                85                  90                  95

Ser Arg Gly Ala Arg Gln Ser Thr Pro Phe Val Cys Glu Tyr Gln Gly
            100                 105                 110

Gln Ser Ser Asp Leu Pro Gln Pro Pro Val Asn Ala Gly Gly Gly Ser
        115                 120                 125

Gly Gly Gly Ser Gly Gly Gly Ser Glu Gly Gly Gly Ser Glu Gly Gly
    130                 135                 140

Gly Ser Glu Gly Gly Gly Ser Glu Gly Gly Gly Ser Gly Gly Gly Ser
145                 150                 155                 160

Gly Ser Gly Asp Phe Asp Tyr Glu Lys Met Ala Asn Ala Asn Lys Gly
                165                 170                 175
```

UNITED STATES PATENT AND TRADEMARK OFFICE
CERTIFICATE OF CORRECTION

PATENT NO.        : 7,371,849 B2
APPLICATION NO. : 10/489477
DATED             : May 13, 2008
INVENTOR(S)       : Honda et al.

It is certified that error appears in the above-identified patent and that said Letters Patent is hereby corrected as shown below:

```
Ala Met Thr Glu Asn Ala Asp Glu Asn Ala Leu Gln Ser Asp Ala Lys
            180             185             190

Gly Lys Leu Asp Ser Val Ala Thr Asp Tyr Gly Ala Ala Ile Asp Gly
            195             200             205

Phe Ile Gly Asp Val Ser Gly Leu Ala Asn Gly Asn Gly Ala Thr Gly
            210             215             220

Asp Phe Ala Gly Ser Asn Ser Gln Met Ala Gln Val Gly Asp Gly Asp
225             230             235             240

Asn Ser Pro Leu Met Asn Asn Phe Arg Gln Tyr Leu Pro Ser Leu Pro
            245             250             255

Gln Ser Val Glu Cys Arg Pro Phe Val Phe Gly Ala Gly Lys Pro Tyr
            260             265             270

Glu Phe Ser Ile Asp Cys Asp Lys Ile Asn Leu Phe Arg Gly Val Phe
            275             280             285

Ala Phe Leu Leu Tyr Val Ala Thr Phe Met Tyr Val Phe Ser Thr Phe
            290             295             300

Ala Asn Ile Leu Arg Asn Lys Glu Ser Ser Thr Ala Gln His Asp Glu
305             310             315             320

Ala Val Asp Asn Lys Phe Asn Lys Glu Gln Gln Asn Ala Phe Tyr Glu
            325             330             335

Ile Leu His Leu Pro Asn Leu Asn Glu Glu Gln Arg Asn Ala Phe Ile
            340             345             350

Gln Ser Leu Lys Asp Asp Pro Ser Gln Ser Ala Asn Leu Leu Ala Glu
            355             360             365

Ala Lys Lys Leu Asn Asp Ala Gln Ala Pro Lys Val Asp Asn Lys Phe
            370             375             380
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
Asn Lys Glu Gln Gln Asn Ala Phe Tyr Glu Ile Leu His Leu Pro Asn
385                 390                 395                 400

Leu Asn Glu Glu Gln Arg Asn Ala Phe Ile Gln Ser Leu Lys Asp Asp
                405                 410                 415

Pro Ser Gln Ser Ala Asn Leu Leu Ala Glu Ala Lys Lys Leu Asn Asp
                420                 425                 430

Ala Gln Ala Pro Lys Val Asp Ala Asn
            435                 440
```

<210> 45
<211> 1890
<212> DNA
<213> Artificial

<220>
<223> An artificially synthesized vector sequence

<400> 45
```
aagcttgcat gcaaattcta tttcaaggag acagtcataa tgaaatacct attgcctacg      60
gcagccgctg gttgttatta ctcgctgccc aaccagcgat ggcccaggtg cagctgcagc     120
agtctggggc agagcttgtg aaccaggggc ctcagtcaag ttgtcctgca cagcttctgg     180
cttcaacatt aaagacacct atatgcactg ggtaagcaga ggcctgaaaa gggtctagaa     240
ttccctgaca tctgaggaca ctgccgtcta ttactgtgct ggtttgatta cggcaacttt     300
gactactggg gccaaggcac cacggtcacc gtctcgagag gcggtggcgg atcagtggcg     360
gtggaagtgg cggtggtggg tccatggccg acatcgagct cacccagtct ccagcctccc     420
tttctgcgtc tgtgggagaa actgtcacca tcaatgtcga gcaagtggga atattcacaa     480
ttatttagca tggtaccaag ctcgagatca aacgggctga tgctcaccaa ctgtatccat     540
cttcccacca tccagtgagc agttaacatc tggaggtgcc tcagtcgtgt gcttctgaac     600
```

Page 5 of 16

UNITED STATES PATENT AND TRADEMARK OFFICE
CERTIFICATE OF CORRECTION

PATENT NO.      : 7,371,849 B2
APPLICATION NO. : 10/489477
DATED           : May 13, 2008
INVENTOR(S)     : Honda et al.

Page 6 of 16

It is certified that error appears in the above-identified patent and that said Letters Patent is hereby corrected as shown below:

```
agcttctacc ccaaagacat caatgtcaag tggaagattg atggcagtga acgacaaaat    660
ggcgtctgaa cagttggact gatcaggaca gcaaagacag cacctacagc atgagcagca    720
ccctcacgtt gaccaagacg agtatgaacg acataacagc tatacctgtg aggccactca    780
caagacatca acttcaccca ttgtcaaggc ttcaacagga atgagtgttc ggcgcgccag    840
tcgactccat tcgtttgtga atatcaaggc caatcgtcta cctgcctcaa cctcctgtca    900
atgctggcgg cggctctggt ggtggttctg gtggcggctc tgagggtggt gctctgaggg    960
tggcggttct gagggtggcg gctctgaggg aggcggttcc ggtggtggct ctggttccgg   1020
tattttgatt atgaaaagat ggcaaacgct aataagggg ctatgaccga aaatgccgat    1080
gaaaacgcgc taagtcagac gctaaaggca aacttgattc tgtcgctact gattacggtg   1140
ctgctatcga tggtttcatt ggtacgtttc cggccttgct aatggtaatg gtgctactgg   1200
tgattttgct ggctctaatt cccaaatggc tcaatcggtg acggtgataa ttcacctttta 1260 atgaataatt tccgtcaata tttaccttcc ctccctcaat cggttaatgt cgccctttg    1320 tcttggcgc tggtaaacca tatgaatttt ctattgattg tgacaaaata aacttatccg   1380
tggtgtcttt gcgtttcttt tatatgttgc cacctttatg tatgtatttt ctacgtttgc   1440
taacatatgc gtaataagga gtcttaatca tgccagttct tttgggtgct agctgtcgac   1500
tgcgcaacac gatgaagcgt agacaacaaa ttcaacaaag aacaacaaaa cgcgttctat   1560
gagatcttac atttacctaa cttaaacgag aacaacgaaa cgccttcatc caaagtttaa   1620
aagatgaccc aagccaaagc gctaaccttt tagcagaagc aaaagctaa atgatgctca     1680 ggcgccgaaa gtagacaaca aattcaacaa agaacaacaa aacgcgttct agagatctta   1740
catttaccta acttaaacga agaacaacga aacgccttca tccaaagttt aaaagatgac   1800
ccagccaaag cgctaacctt ttagcagaag ctaaaaagct aaatgatgct caggcgccga   1860
aagtagacgc gaatagctgg gaattaattc                                    1890
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
<210>  46
<211>  590
<212>  PRT
<213>  Artificial

<220>
<223>  An artificially synthesized vector sequence

<400>  46

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30
Leu Val Lys Pro Gly Ala Ser Val Lys Leu Ser Cys Thr Ala Ser Gly
            35                  40                  45

Phe Asn Ile Lys Asp Thr Tyr Met His Trp Val Lys Gln Arg Pro Glu
            50                  55                  60

Lys Gly Leu Thr Ser Glu Asp Thr Ala Val Tyr Tyr Cys Ala Gly Tyr
65                  70                  75                  80

Asp Tyr Gly Asn Phe Asp Tyr Trp Gly Gln Gly Thr Thr Val Thr Val
                85                  90                  95

Ser Ser Gly Gly Gly Gly Ser Gly Gly Gly Gly Ser Gly Gly Gly Gly
                100                 105                 110

Ser Met Ala Asp Ile Glu Leu Thr Gln Ser Pro Ala Ser Leu Ser Ala
            115                 120                 125

Ser Val Gly Glu Thr Val Thr Ile Thr Cys Arg Ala Ser Gly Asn Ile
            130                 135                 140

His Asn Tyr Leu Ala Lys Leu Glu Ile Lys Arg Ala Asp Ala Pro Thr
145                 150                 155                 160
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
Val Ser Ile Phe Pro Pro Ser Ser Glu Gln Leu Thr Ser Gly Gly Ala
            165                 170                 175

Ser Val Val Cys Phe Asn Ser Phe Tyr Pro Lys Asp Ile Asn Val Lys
            180                 185                 190

Trp Lys Ile Asp Gly Ser Glu Arg Gln Asn Gly Val Asn Ser Trp Thr
            195                 200                 205

Asp Gln Asp Ser Lys Asp Ser Thr Tyr Ser Met Ser Ser Thr Leu Thr
            210                 215                 220

Leu Thr Lys Glu Tyr Glu Arg His Asn Ser Tyr Thr Cys Glu Ala Thr
225             230                 235                 240

His Lys Thr Ser Thr Ser Pro Ile Val Lys Phe Asn Arg Asn Glu Cys
            245                 250                 255

Ser Ala Arg Gln Ser Thr Pro Phe Val Cys Glu Tyr Gln Gly Gln Ser
            260                 265                 270

Ser Leu Pro Gln Pro Pro Val Asn Ala Gly Gly Gly Ser Gly Gly Gly
            275                 280                 285

Ser Gly Gly Gly Ser Glu Gly Gly Ser Glu Gly Gly Gly Ser Glu Gly
            290                 295                 300

Gly Gly Ser Glu Gly Gly Gly Ser Gly Gly Gly Ser Gly Ser Gly Phe
305             310                 315                 320

Asp Tyr Glu Lys Met Ala Asn Ala Asn Lys Gly Ala Met Thr Glu Asn
            325                 330                 335

Ala Asp Glu Asn Ala Leu Ser Asp Ala Lys Gly Lys Leu Asp Ser Val
            340                 345                 350

Ala Thr Asp Tyr Gly Ala Ala Ile Asp Gly Phe Ile Gly Val Ser Gly
            355                 360                 365
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
Leu Ala Asn Gly Asn Gly Ala Thr Gly Asp Phe Ala Gly Ser Asn Ser
    370             375             380
Gln Met Ala Gln Gly Asp Gly Asp Asn Ser Pro Leu Met Asn Asn Phe
385             390             395             400
Arg Gln Tyr Leu Pro Ser Leu Pro Gln Ser Val Cys Arg Pro Phe Val
            405             410             415
Phe Gly Ala Gly Lys Pro Tyr Glu Phe Ser Ile Asp Cys Asp Lys Ile
            420             425             430
Asn Leu Arg Gly Val Phe Ala Phe Leu Leu Tyr Val Ala Thr Phe Met
        435             440             445
Tyr Val Phe Ser Thr Phe Ala Asn Ile Arg Asn Lys Glu Ser Ser Thr
        450             455             460
Ala Gln His Asp Glu Ala Val Asp Asn Lys Phe Asn Lys Glu Gln Gln
465             470             475             480
Asn Ala Phe Tyr Glu Ile Leu His Leu Pro Asn Leu Asn Glu Glu Gln
            485             490             495
Arg Asn Ala Phe Ile Gln Ser Leu Lys Asp Asp Pro Ser Gln Ser Ala
            500             505             510
Asn Leu Leu Ala Glu Ala Lys Lys Leu Asn Asp Ala Gln Ala Pro Lys
        515             520             525
Val Asp Asn Lys Phe Asn Lys Glu Gln Gln Asn Ala Phe Tyr Glu Ile
        530             535             540
Leu His Leu Pro Asn Leu Asn Glu Glu Gln Arg Asn Ala Phe Ile Gln
545             550             555             560
Ser Leu Lys Asp Asp Pro Ser Gln Ser Ala Asn Leu Leu Ala Glu Ala
            565             570             575
Lys Lys Leu Asn Asp Ala Gln Ala Pro Lys Val Asp Ala Asn
            580             585             590
```

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
<210>  47
<211>  1773
<212>  DNA
<213>  Artificial

<220>
<223>  An artificially synthesized vector sequence

<400>  47
aagcttgcat gcaaattcta tttcaaggag acagtcataa tgaaatacct attgcctacg      60
gcagccgctg gattgttatt actcgcggcc cagccggcca tggcccaggt gcagctgcag     120
cagtctgggg cagagcttgt gaagccaggg gcctcagtca agttgtcctg cacagcttct     180
ggcttcaaca ttaaagacac ctatatgcac tgggtgaagc agaggcctga aagggtcta     240 gaattccctg acatctgagg acactgccgt ctattactgt gctggttatg attacggcaa     300
ctttgactac tggggccaag caccacggt caccgtctcc tcaggcggtg gcggatcagg     360
tggcggtgga agtggcggtg gtgggtctac tagtgacatc gagctcaccc agtctccagc     420
ctccctttct gcgtctgtgg gagaaactgt caccatcaca tgtcgagcaa gtgggaatat     480
tcacaattat ttagcatggt accagcagaa accagggaaa tctcctcagc tcctggtcta     540
taatgcaaaa accttagcag atggtgtgcc atcaaggttc agtggcagtg gatccggaac     600
acaatattct ctcaagatca acagcctgca gcctgaagat tttgggagtt attactgtca     660 acattttgg agtactccgt ggacgttcgg tggaggtacc aagctcgagt cgactccatt     720
cgtttgtgaa tatcaaggcc aatcgtctga cctgcctcaa cctcctgtca atgctggcgg     780
cggctctggt ggtggttctg gtggcggctc tgagggtggt ggctctgagg gtggcggttc     840
tgagggtggc ggctctgagg gaggcggttc cggtggtggc tctggttccg gtgattttga     900
ttatgaaaag atggcaaacg ctaataaggg ggctatgacc gaaaatgccg atgaaaacgc     960
```

Page 10 of 16

```
gctacagtca gacgctaaag gcaaacttga ttctgtcgct actgattacg gtgctgctat   1020
cgatggtttc attggtgacg tttccggcct tgctaatggt aatggtgcta ctggtgattt   1080
tgctggctct aattcccaaa tggctcaagt cggtgacggt gataattcac ctttaatgaa   1140
taatttccgt caatatttac cttccctccc tcaatcggtt gaatgtcgcc cttttgtctt   1200
tggcgctggt aaaccatatg aatttctat tgattgtgac aaaataaact tattccgtgg   1260
tgtctttgcg tttctttat atgttgccac ctttatgtat gtattttcta cgtttgctaa   1320
catactgcgt aataaggagt cttaatcatg ccagttcttt tgggtgctag ctgtcgactg   1380
cgcaacacga tgaagccgta gacaacaaat tcaacaaaga acaacaaaac gcgttctatg   1440
agatcttaca tttacctaac ttaaacgaag aacaacgaaa cgccttcatc caaagtttaa   1500
aagatgaccc aagccaaagc gctaacctt tagcagaagc taaaaagcta aatgatgctc   1560
aggcgccgaa agtagacaac aaatgagatc ttacatttac ctaacttaaa cgaagaacaa   1620
cgaaacgcct tcatccaaag tttaaaagat gacccatcaa caagaacaa caaaacgcgt   1680 tctatagcca aagcgctaac cttttagcag aagctaaaaa gctaaatgat gctcaggcgc   1740
cgaaagtaga cgcgaattag ctgggaatta att                                1773
```

<210> 48
<211> 559
<212> PRT
<213> Artificial

<220>
<223> An artificially synthesized vector sequence

<400> 48

Met Lys Tyr Leu Leu Pro Thr Ala Ala Ala Gly Leu Leu Leu Leu Ala
1               5                   10                  15

UNITED STATES PATENT AND TRADEMARK OFFICE
CERTIFICATE OF CORRECTION

PATENT NO. : 7,371,849 B2
APPLICATION NO. : 10/489477
DATED : May 13, 2008
INVENTOR(S) : Honda et al.

It is certified that error appears in the above-identified patent and that said Letters Patent is hereby corrected as shown below:

```
Ala Gln Pro Ala Met Ala Gln Val Gln Leu Gln Gln Ser Gly Ala Glu
            20              25              30

Leu Val Lys Pro Gly Ala Ser Val Lys Leu Ser Cys Thr Ala Ser Gly
            35              40              45

Phe Asn Ile Lys Asp Thr Tyr Met His Trp Val Lys Gln Arg Pro Glu
            50              55              60

Lys Gly Leu Thr Ser Glu Asp Thr Ala Val Tyr Tyr Cys Ala Gly Tyr
65              70              75              80

Asp Tyr Gly Asn Phe Asp Tyr Trp Gly Gln Gly Thr Thr Val Thr Val
            85              90              95

Ser Ser Gly Gly Gly Gly Ser Gly Gly Gly Gly Ser Gly Gly Gly Gly
            100             105             110

Ser Thr Ser Asp Ile Glu Leu Thr Gln Ser Pro Ala Ser Leu Ser Ala
            115             120             125

Ser Val Gly Glu Thr Val Thr Ile Thr Cys Arg Ala Ser Gly Asn Ile
            130             135             140

His Asn Tyr Leu Ala Trp Tyr Gln Gln Lys Pro Gly Lys Ser Pro Gln
145             150             155             160

Leu Leu Val Tyr Asn Ala Lys Thr Leu Ala Asp Gly Val Pro Ser Arg
            165             170             175

Phe Ser Gly Ser Gly Ser Gly Thr Gln Tyr Ser Leu Lys Ile Asn Ser
            180             185             190

Leu Gln Pro Glu Asp Phe Gly Ser Tyr Tyr Cys Gln His Phe Trp Ser
            195             200             205

Thr Pro Trp Thr Phe Gly Gly Gly Thr Lys Ile Glu Ser Thr Pro Phe
            210             215             220

Val Cys Glu Tyr Gln Gly Gln Ser Ser Asp Leu Pro Gln Pro Pro Val
225             230             235             240
```

UNITED STATES PATENT AND TRADEMARK OFFICE
CERTIFICATE OF CORRECTION

| | |
|---|---|
| PATENT NO. | : 7,371,849 B2 |
| APPLICATION NO. | : 10/489477 |
| DATED | : May 13, 2008 |
| INVENTOR(S) | : Honda et al. |

It is certified that error appears in the above-identified patent and that said Letters Patent is hereby corrected as shown below:

```
Asn Ala Gly Gly Gly Ser Gly Gly Gly Ser Gly Gly Gly Ser Glu Gly
                245                 250                 255

Gly Gly Ser Glu Gly Gly Gly Ser Glu Gly Gly Gly Ser Glu Gly Gly
            260                 265                 270

Gly Ser Gly Gly Gly Ser Gly Ser Gly Asp Phe Asp Tyr Glu Lys Met
        275                 280             285

Ala Asn Ala Asn Lys Gly Ala Met Thr Glu Asn Ala Asp Glu Asn Ala
        290             295                 300

Leu Gln Ser Asp Ala Lys Gly Lys Leu Asp Ser Val Ala Thr Asp Tyr
305                 310                 315                 320

Gly Ala Ala Ile Asp Gly Phe Ile Gly Asp Val Ser Gly Leu Ala Asn
                325                 330                 335

Gly Asn Gly Ala Thr Gly Asp Phe Ala Gly Ser Asn Ser Gln Met Ala
                340                 345                 350

Gln Val Gly Asp Gly Asp Asn Ser Pro Leu Met Asn Asn Phe Arg Gln
            355                 360                 365

Tyr Leu Pro Ser Leu Pro Gln Ser Val Glu Cys Arg Pro Phe Val Phe
            370                 375                 380

Gly Ala Gly Lys Pro Tyr Glu Phe Ser Ile Asp Cys Asp Lys Ile Asn
385                 390                 395                 400

Leu Phe Arg Gly Val Phe Ala Phe Leu Leu Tyr Val Ala Thr Phe Met
                405                 410                 415

Tyr Val Phe Ser Thr Phe Ala Asn Ile Leu Arg Asn Lys Glu Ser Ser
                420                 425                 430

Thr Ala Gln His Asp Glu Ala Val Asp Asn Lys Phe Asn Lys Glu Gln
            435                 440                 445

Gln Asn Ala Phe Tyr Glu Ile Leu His Leu Pro Asn Leu Asn Glu Glu
            450                 455                 460
```

UNITED STATES PATENT AND TRADEMARK OFFICE
CERTIFICATE OF CORRECTION

PATENT NO.         : 7,371,849 B2
APPLICATION NO. : 10/489477
DATED                  : May 13, 2008
INVENTOR(S)       : Honda et al.

It is certified that error appears in the above-identified patent and that said Letters Patent is hereby corrected as shown below:

```
Gln Arg Asn Ala Phe Ile Gln Ser Leu Lys Asp Asp Pro Ser Gln Ser
465             470             475             480

Ala Asn Leu Leu Ala Glu Ala Lys Lys Leu Asn Asp Ala Gln Ala Pro
        485             490             495

Lys Val Asp Asn Lys Phe Asn Lys Glu Gln Gln Asn Ala Phe Tyr Glu
        500             505             510

Ile Leu His Leu Pro Asn Leu Asn Glu Glu Gln Arg Asn Ala Phe Ile
        515             520             525

Gln Ser Leu Lys Asp Asp Pro Ser Gln Ser Ala Asn Leu Leu Ala Glu
        530             535             540

Ala Lys Lys Leu Asn Asp Ala Gln Ala Pro Lys Val Asp Ala Asn
545             550             555

<210>  49
<211>  17
<212>  PRT
<213>  Artificial

<220>
<223>  An artificially synthesized peptide sequence

<400>  49

Asp Phe Lys Pro Trp Cys Ser Asp Gly Leu Gly Thr Thr Leu Pro Asn
1               5               10              15

Tyr
```

UNITED STATES PATENT AND TRADEMARK OFFICE
CERTIFICATE OF CORRECTION

| | |
|---|---|
| PATENT NO. | : 7,371,849 B2 |
| APPLICATION NO. | : 10/489477 |
| DATED | : May 13, 2008 |
| INVENTOR(S) | : Honda et al. |

It is certified that error appears in the above-identified patent and that said Letters Patent is hereby corrected as shown below:

<210> 50
<211> 12
<212> PRT
<213> Artificial

<220>
<223> An artificially synthesized peptide sequence

<400> 50

Asp Gly Gly Tyr Tyr Ser Cys Gly Val Gly Glu Glu
1               5                   10

<210> 51
<211> 18
<212> PRT
<213> Artificial

<220>
<223> An artificially synthesized peptide sequence

<400> 51

Lys Ser Tyr Met Cys Gly Ser Thr Leu Trp Arg Arg Ile Asp Gln Tyr
1               5                   10                  15

Asn Asp

UNITED STATES PATENT AND TRADEMARK OFFICE
CERTIFICATE OF CORRECTION

PATENT NO.       : 7,371,849 B2
APPLICATION NO.  : 10/489477
DATED            : May 13, 2008
INVENTOR(S)      : Honda et al.

It is certified that error appears in the above-identified patent and that said Letters Patent is hereby corrected as shown below:

<210> 52
<211> 18
<212> PRT
<213> Artificial

<220>
<223> An artificially synthesized peptide sequence

<400> 52

Asp Ile Ser Ala Pro Pro Gly Ile Gly Gly Thr Cys Ala Phe Leu Gly
1               5               10              15

Asp Tyr

Signed and Sealed this

Sixteenth Day of September, 2008

JON W. DUDAS
*Director of the United States Patent and Trademark Office*